(12) United States Patent
Yang et al.

(10) Patent No.: US 7,485,431 B2
(45) Date of Patent: Feb. 3, 2009

(54) IDENTIFICATION OF A FAMILY OF SECRETED PROTEINS IN VASCULAR ENDOTHELIUM

(75) Inventors: Ruey-Bing Yang, San Mateo, CA (US); Chi Kin Domingos Ng, San Francisco, CA (US); James E. Tomlinson, Burlingame, CA (US); Laszlo G. Komuves, San Francisco, CA (US); James N. Topper, Los Altos, CA (US); Keith E. Robison, Wilmington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/726,543

(22) Filed: Mar. 22, 2007

(65) Prior Publication Data

US 2007/0172882 A1    Jul. 26, 2007

Related U.S. Application Data

(63) Continuation of application No. 10/406,073, filed on Apr. 3, 2003, now Pat. No. 7,258,988.

(60) Provisional application No. 60/369,876, filed on Apr. 5, 2002.

(51) Int. Cl.
*G01N 33/53* (2006.01)
*C07K 16/00* (2006.01)
*C07K 16/18* (2006.01)
*C07K 16/46* (2006.01)

(52) U.S. Cl. .................. 435/7.1; 530/387.1; 530/387.9; 530/388.15; 530/388.24

(58) Field of Classification Search .................. None
See application file for complete search history.

(56) References Cited

U.S. PATENT DOCUMENTS 6,750,013 B2 *  6/2004  Gish et al. ............ 435/6
2002/0006616 A1 *  1/2002  Gish et al. ............ 435/6

FOREIGN PATENT DOCUMENTS

| WO | WO03/000012 A2 | 1/2003 |
| WO | WO 03/002610 A1 | 1/2003 |
| WO | WO03/004989 A2 | 1/2003 |
| WO | WO 03/077875 A2 | 9/2003 |

OTHER PUBLICATIONS

Bahr, A., et al., "*Homo sapiens* CEGP1 protein (CEGP1), mRNA," Nov. 2, 2000 (sequence) GenBank [online] Bethesda, MD, USA: National Center for Biotechnology Information [retrieved on Mar. 26, 2002]. GenBank Accession No. NM_020974.

Yang, Ruey-Bing, et al., "Identification of a novel family of cell-surface proteins expressed in human vascular endothelium," *The Journal of Biological Chemistry*, vol. 277, No. 48 (Nov. 29, 2002) pp. 46364-46373.

* cited by examiner

*Primary Examiner*—James Martinell

(57) ABSTRACT

The invention relates to SCUBE molecules and generally to gene expression in vascular endothelial cells. The invention specifically relates to the discovery of a novel gene family containing the genes and proteins referred to herein as SCUBE1, SCUBE2 and SCUBE3 which can be expressed in endothelial cells. SCUBE proteins may be involved in the development of cardiovascular disease, hemostasis, thrombosis, inflammatory disease, bone metabolism disorders, urinary bladder disorders and breast disorders.

11 Claims, 15 Drawing Sheets

Figure 1

```
|--> signal peptide <---|                                    |-> EGF-like #1                              |->
MGAAAVRWHL CVLLALGTRG RLAGGSGLPG SVDVDECSEG TDDCHIDAIC QNAPKSYKCL CKPGYKGEGK QCQDIDECEN      80

EGF-like #2
DYYNGGCVHE CINIPGNYRC TCFDGFMLAH DGHNCLDVDE CQDNNGGCQQ ICVNAMGSYE CQCHSGFFLS DNQHTCIHRS     160
                                          |-> EGF-like #3
NEGMNCMNKD HGCAHICRET PKGGVACDCR PGFDLAQNQK DCTLTCNYGN GGCQHSCEDT DTGPTCGCHQ KYAPHSDGRT     240
        |-> EGF-like #4                                  |-> EGF-like #5
CIETCAVNNG GCDRTCKDTA TGVRCSCPVG FTLQPDGKTC KDINECLVNN GGCDHFCRNT VGSFECGCRK GYKLLTDERT     320
        |-> EGF-like #6                                  |-> EGF-like #7
CQDIDECSFE RTCDHICINS PGSFQCLCHR GYILYGTTHC GDVDECSMSN GSCDQGCVNT KGSYECVCPP GRRLHWNRKD     400
|--> D2 deletion <--|                                    |-> EGF-like #9
CVETGKCLSR AKTSPRAQLS CSKAGGVESC FLSCPAHTLF VPDSENSYVL SCGVPGPQGK ALQKRNGTSS GLGPSCSDAP     480

TTPIKQKARF KIRDAKCHLR PHSQARAKET ARQPLLDHCH VTFVTLKCDS SKKRRRGRKS PSKEVSHITA EFEIETKMEE     560

ASDTCEADCL RKRAEQSLQA AIKTLRKSIG RQQFYVQVSG TEYEVAQRPA KALEGQDACG AGQVLQDSKC VACGPGTHFG     640

GELGQCVPCM PGTYQDMEGQ LSCTPCPSSD GLGLPGARNV SECGGQCSPG FFSADGFKPC QACPVGTYQP EPGRTCFPC     720
                        |-> EGF-like #10                 |--> D1 deletion <--|
GGGLLTKHEG TTSFQDCEAK VHCSPGHHYN TTTHRCIRCP VGTYQPEEGQ NHCITCPGNT STDFDGSTNV THCKNQHCGG     800
CUB domain
ELGDYTGYIE SPNYPGDYPA NAECVWHIAP PPKRRILIVV PEIFLPIEDE CGDVLVMRKS ASPTSITYE TCQTYERPIA     880

FTSRSRKLWI QFKSNEGNSG KGFQVPYVTY DEDYQQLIED IVRDGRLYAS ENHQEILKDK KLIKALFDVL AHPQNYFKYT     960

AQESKEMFPR SFIKLLRSKV SRFLRPYK                                                             988
``` a
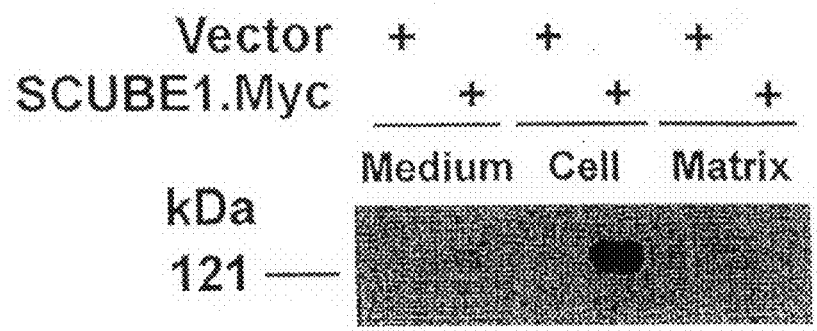
b
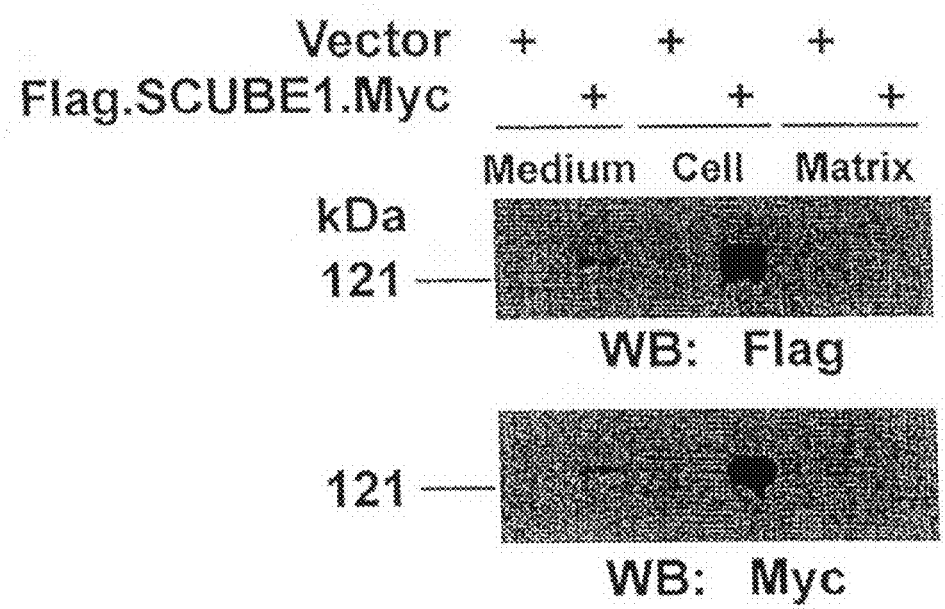
c
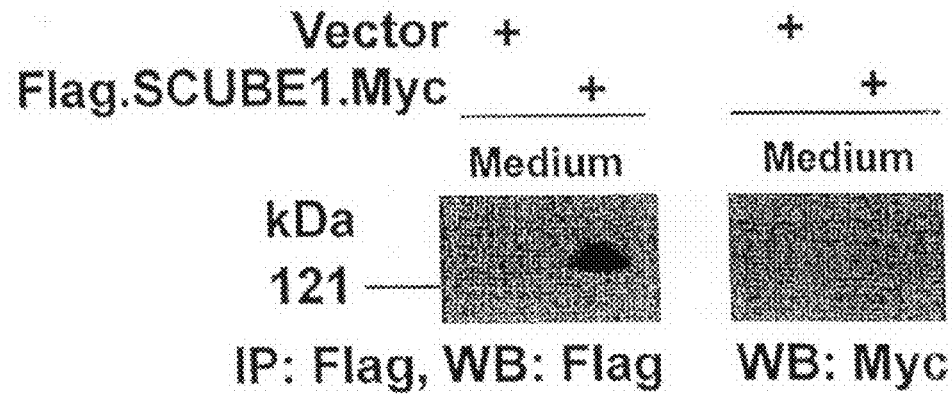
Figure 3

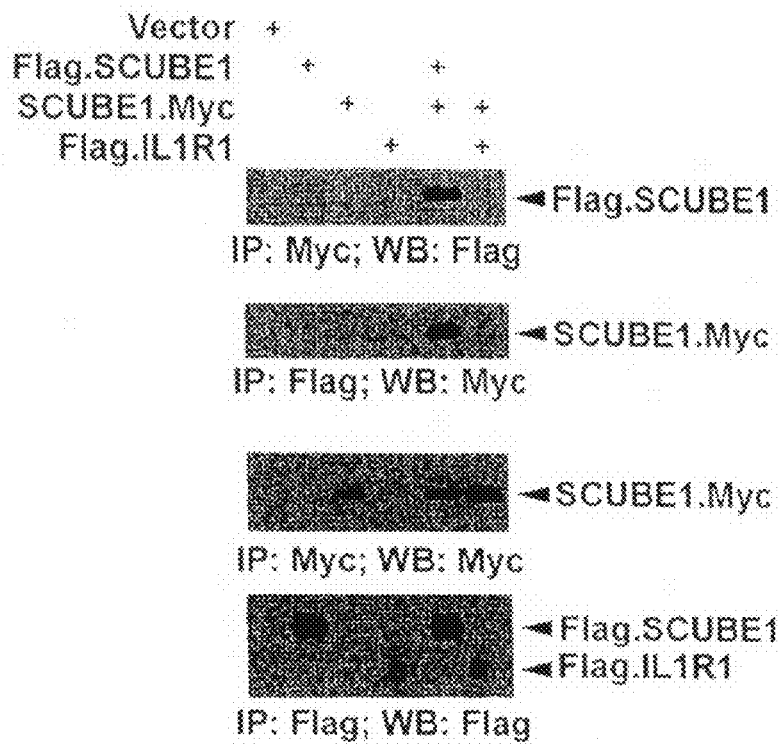
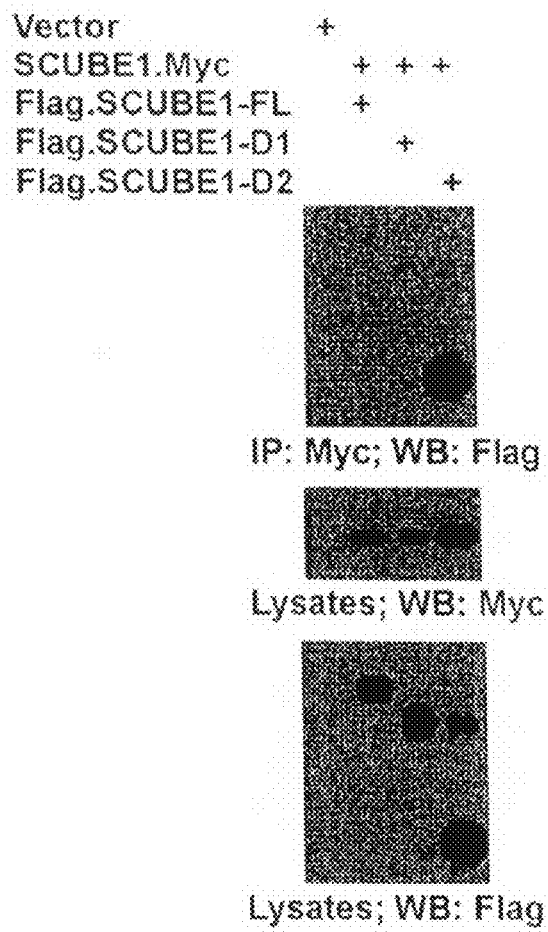
Figure 8 a = umbilical artery (insert: umbilical vein); b = Cynomolgus brain
c, d = Cynomolgus lung, e, f = Cynomolgus kidney a = E18 mouse embryo, heart; b = E18 mouse embryo, vena cava and aorta;
c = E18 mouse embryo, lung; d = E18 mouse embryo, thoracic wall
e = E18 mouse embryo, small intestine; f = E18 mouse embryo, cerebrum

SEQUENCE LISTING

```
<160> NUMBER OF SEQ ID NOS: 23

<210> SEQ ID NO 1
<211> LENGTH: 2992
<212> TYPE: DNA
<213> ORGANISM: Homo sapiens
<220> FEATURE:
<221> NAME/KEY: CDS
<222> LOCATION: (21)..(2987)
a<223> OTHER INFORMATION: SCUBE1

<400> SEQUENCE: 1
cagcggggcc cgcattgagc atg ggc gcg gcg gcc gtg cgc tgg cac ttg tgc      53
                     Met Gly Ala Ala Ala Val Arg Trp His Leu Cys
                     1               5                  10 gtg ctg ctg gcc ctg ggc aca cgc ggg cgg ctg gcc ggg ggc agc ggg        101
Val Leu Leu Ala Leu Gly Thr Arg Gly Arg Leu Ala Gly Gly Ser Gly
             15                  20                  25 ctc cca ggg tca gtc gac gtg gat gag tgc tca gag ggc aca gat gac        149
Leu Pro Gly Ser Val Asp Val Asp Glu Cys Ser Glu Gly Thr Asp Asp
         30                  35                  40 tgc cac atc gat gcc atc tgt cag aac gcg ccc aag tcc tac aaa tgc        197
Cys His Ile Asp Ala Ile Cys Gln Asn Ala Pro Lys Ser Tyr Lys Cys
     45                  50                  55 ctc tgc aag cca ggc tac aag ggg gaa ggc aag cag tgt gga gac att        245
Leu Cys Lys Pro Gly Tyr Lys Gly Glu Gly Lys Gln Cys Gly Asp Ile
60                  65                  70                  75
```

-continued

| | |
|---|---|
| gac gag tgt gag aat gac tac tac aat ggg ggc tgt gtc cac gag tgc<br>Asp Glu Cys Glu Asn Asp Tyr Tyr Asn Gly Gly Cys Val His Glu Cys<br>                  80                        85                    90 | 293 |
| atc aac atc ccg ggg aac tac agg tgt acc tgc ttt gat ggc ttc atg<br>Ile Asn Ile Pro Gly Asn Tyr Arg Cys Thr Cys Phe Asp Gly Phe Met<br>                95                      100                  105 | 341 |
| ctg gca cac gat gga cac aac tgc ctg gat gtg gac gag tgt cag gac<br>Leu Ala His Asp Gly His Asn Cys Leu Asp Val Asp Glu Cys Gln Asp<br>             110                      115                      120 | 389 |
| aat aat ggt ggc tgc cag cag atc tgc gtc aat gcc atg ggc agc tac<br>Asn Asn Gly Gly Cys Gln Gln Ile Cys Val Asn Ala Met Gly Ser Tyr<br>        125                      130                      135 | 437 |
| gag tgt cag tgc cac agt ggc ttc ttc ctt agt gac aac cag cat acc<br>Glu Cys Gln Cys His Ser Gly Phe Phe Leu Ser Asp Asn Gln His Thr<br>140                      145                      150                      155 | 485 |
| tgc atc cac cgc tcc aat gag ggt atg aac tgc atg aac aaa gac cat<br>Cys Ile His Arg Ser Asn Glu Gly Met Asn Cys Met Asn Lys Asp His<br>                    160                      165                      170 | 533 |
| ggc tgt gcc cac atc tgc cgg gag acg ccc aaa ggt ggg gtg gcc tgc<br>Gly Cys Ala His Ile Cys Arg Glu Thr Pro Lys Gly Gly Val Ala Cys<br>             175                      180                      185 | 581 |
| gac tgc agg ccc ggc ttt gac ctt gcc caa aac cag aag gac tgc aca<br>Asp Cys Arg Pro Gly Phe Asp Leu Ala Gln Asn Gln Lys Asp Cys Thr<br>             190                      195                      200 | 629 |
| cta acc tgt aat tat gga aac gga ggc tgc cag cac agc tgt gag gac<br>Leu Thr Cys Asn Tyr Gly Asn Gly Gly Cys Gln His Ser Cys Glu Asp<br>        205                      210                      215 | 677 |
| aca gac aca ggc ccc acg tgt ggt tgc cac cag aag tac gcc ccc cac<br>Thr Asp Thr Gly Pro Thr Cys Gly Cys His Gln Lys Tyr Ala Pro His<br>220                      225                      230                      235 | 725 |
| tca gac ggt cgc acg tgc atc gag acg tgc gca gtc aat aac gga ggc<br>Ser Asp Gly Arg Thr Cys Ile Glu Thr Cys Ala Val Asn Asn Gly Gly<br>             240                      245                      250 | 773 |
| tgc gac cgg aca tgc aag gac aca gcc act ggc gtg cga tgc agc tgc<br>Cys Asp Arg Thr Cys Lys Asp Thr Ala Thr Gly Val Arg Cys Ser Cys<br>             255                      260                      265 | 821 |
| ccc gtt gga ttc aca ctg cag ccg gac ggg aag aca tgc aaa gac atc<br>Pro Val Gly Phe Thr Leu Gln Pro Asp Gly Lys Thr Cys Lys Asp Ile<br>             270                      275                      280 | 869 |
| aac gag tgc ctg gtc aac aac gga ggc tgc gac cac ttc tgc cgc aac<br>Asn Glu Cys Leu Val Asn Asn Gly Gly Cys Asp His Phe Cys Arg Asn<br>        285                      290                      295 | 917 |
| acc gta ggc agc ttc gag tgc ggc tgc cgg aag ggc tac aag ctg ctc<br>Thr Val Gly Ser Phe Glu Cys Gly Cys Arg Lys Gly Tyr Lys Leu Leu<br>300                      305                      310                      315 | 965 |
| acc gac gag cgc acc tgc cag gac atc gac gag tgc tcc ttc gag cgg<br>Thr Asp Glu Arg Thr Cys Gln Asp Ile Asp Glu Cys Ser Phe Glu Arg<br>                    320                      325                      330 | 1013 |
| acc tgt gac cac atc tgc atc aac tcc ccg ggc agc ttc cag tgc ctg<br>Thr Cys Asp His Ile Cys Ile Asn Ser Pro Gly Ser Phe Gln Cys Leu<br>             335                      340                      345 | 1061 |
| tgt cac cgc ggc tac atc ctc tac ggg aca acc cac tgc gga gat gtg<br>Cys His Arg Gly Tyr Ile Leu Tyr Gly Thr Thr His Cys Gly Asp Val<br>        350                      355                      360 | 1109 |
| gac gag tgc agc atg agc aac ggg agc tgt gac cag ggc tgc gtc aac<br>Asp Glu Cys Ser Met Ser Asn Gly Ser Cys Asp Gln Gly Cys Val Asn<br>365                      370                      375 | 1157 |
| acc aag ggc agc tac gag tgc gtc tgt ccc ccg ggg agg cgg ctc cac<br>Thr Lys Gly Ser Tyr Glu Cys Val Cys Pro Pro Gly Arg Arg Leu His | 1205 |

|                   |      |
|-------------------|------|
| ```
            380                 385                 390                 395
tgg aac cgg aag gat tgc gtg gag aca ggc aag tgt ctt tct cgc gcc
Trp Asn Arg Lys Asp Cys Val Glu Thr Gly Lys Cys Leu Ser Arg Ala
                400                 405                 410 aag acc tcc ccc cgg gcc cag ctg tcc tgc agc aag gca ggc ggt gtg
Lys Thr Ser Pro Arg Ala Gln Leu Ser Cys Ser Lys Ala Gly Gly Val
                415                 420                 425 gag agc tgc ttc ctt tcc tgc ccg gct cac aca ctc ttc gtg cca gac
Glu Ser Cys Phe Leu Ser Cys Pro Ala His Thr Leu Phe Val Pro Asp
                430                 435                 440 tcg gaa aat agc tac gtc ctg agc tgc gga gtt cca ggg ccg cag ggc
Ser Glu Asn Ser Tyr Val Leu Ser Cys Gly Val Pro Gly Pro Gln Gly
                445                 450                 455 aag gcg ctg cag aaa cgc aac ggc acc agc tct ggc ctc ggc ccc agc
Lys Ala Leu Gln Lys Arg Asn Gly Thr Ser Ser Gly Leu Gly Pro Ser
460                 465                 470                 475 tgc tca gat gcc ccc acc acc ccc atc aaa cag aag gcc cgc ttc aag
Cys Ser Asp Ala Pro Thr Thr Pro Ile Lys Gln Lys Ala Arg Phe Lys
                480                 485                 490 atc cga gat gcc aag tgc cac ctc cgg ccc cac agc cag gca cga gca
Ile Arg Asp Ala Lys Cys His Leu Arg Pro His Ser Gln Ala Arg Ala
                495                 500                 505 aag gag acc gcc agg cag ccg ctg ctg gac cac tgc cat gtg act ttc
Lys Glu Thr Ala Arg Gln Pro Leu Leu Asp His Cys His Val Thr Phe
                510                 515                 520 gtg acc ctc aag tgt gac tcc tcc aag aag agg cgc gtg ggc cgc aag
Val Thr Leu Lys Cys Asp Ser Ser Lys Lys Arg Arg Arg Gly Arg Lys
525                 530                 535 tcc cca tcc aag gag gtg tcc cac att aca gca gag ttt gag atc gag
Ser Pro Ser Lys Glu Val Ser His Ile Thr Ala Glu Phe Glu Ile Glu
540                 545                 550                 555 aca aag atg gaa gag gcc tca gac aca tgc gaa gcg gac tgc ttg cgg
Thr Lys Met Glu Glu Ala Ser Asp Thr Cys Glu Ala Asp Cys Leu Arg
                560                 565                 570 aag cga gca gaa cag agc ctg cag gcc gcc atc aag acc ctg cgc aag
Lys Arg Ala Glu Gln Ser Leu Gln Ala Ala Ile Lys Thr Leu Arg Lys
                575                 580                 585 tcc atc ggc cgg cag cag ttc tat gtc cag gtc tca ggc act gag tac
Ser Ile Gly Arg Gln Gln Phe Tyr Val Gln Val Ser Gly Thr Glu Tyr
                590                 595                 600 gag gta gcc cag agg cca gcc aag gcg ctg gag ggg cag ggg gca tgt
Glu Val Ala Gln Arg Pro Ala Lys Ala Leu Glu Gly Gln Gly Ala Cys
605                 610                 615 ggc gca ggc cag gtg cta cag gac agc aaa tgc gtt gcc tgt ggg cct
Gly Ala Gly Gln Val Leu Gln Asp Ser Lys Cys Val Ala Cys Gly Pro
620                 625                 630                 635 ggc acc cac ttc ggt ggt gag ctc ggc cag tgt gtg cca tgt atg cca
Gly Thr His Phe Gly Gly Glu Leu Gly Gln Cys Val Pro Cys Met Pro
                640                 645                 650 gga aca tac cag gac atg gaa ggc cag ctc agt tgc aca ccg tgc ccc
Gly Thr Tyr Gln Asp Met Glu Gly Gln Leu Ser Cys Thr Pro Cys Pro
                655                 660                 665 agc agc gac ggg ctt ggt ctg cct ggt gcc cgc aac gtg tcg gaa tgt
Ser Ser Asp Gly Leu Gly Leu Pro Gly Ala Arg Asn Val Ser Glu Cys
                670                 675                 680 gga ggc cag tgt tct cca ggc ttc ttc tcg gcc gat ggc ttc aag ccc
Gly Gly Gln Cys Ser Pro Gly Phe Phe Ser Ala Asp Gly Phe Lys Pro
                685                 690                 695 tgc cag gcc tgc ccc gtg ggc acg tac cag cct gag ccc ggg cgc acc
``` | 1253 |
|  | 1301 |
|  | 1349 |
|  | 1397 |
|  | 1445 |
|  | 1493 |
|  | 1541 |
|  | 1589 |
|  | 1637 |
|  | 1685 |
|  | 1733 |
|  | 1781 |
|  | 1829 |
|  | 1877 |
|  | 1925 |
|  | 1973 |
|  | 2021 |
|  | 2069 |
|  | 2117 |
|  | 2165 |

```
Cys Gln Ala Cys Pro Val Gly Thr Tyr Gln Pro Glu Pro Gly Arg Thr
700             705                 710                 715 ggc tgc ttc ccc tgt gga ggg ggt ttg ctc acc aaa cac gaa ggc acc    2213
Gly Cys Phe Pro Cys Gly Gly Gly Leu Leu Thr Lys His Glu Gly Thr
                720                 725                 730 acc tcc ttc cag gac tgc gag gct aaa gtg cac tgc tcc ccc ggc cac    2261
Thr Ser Phe Gln Asp Cys Glu Ala Lys Val His Cys Ser Pro Gly His
            735                 740                 745 cac tac aac acc acc acc cac cgc tgc atc cgc tgc ccc gtc ggc acc    2309
His Tyr Asn Thr Thr Thr His Arg Cys Ile Arg Cys Pro Val Gly Thr
        750                 755                 760 tac cag ccc gag ttt ggc cag aac cac tgc atc acc tgt ccg ggc aac    2357
Tyr Gln Pro Glu Phe Gly Gln Asn His Cys Ile Thr Cys Pro Gly Asn
    765                 770                 775 acc agc aca gac ttc gat ggc tcc acc aac gtc aca cac tgc aaa aac    2405
Thr Ser Thr Asp Phe Asp Gly Ser Thr Asn Val Thr His Cys Lys Asn
780                 785                 790                 795 cag cac tgc ggc ggc gag ctt ggt gac tac acc ggc tac atc gag tcc    2453
Gln His Cys Gly Gly Glu Leu Gly Asp Tyr Thr Gly Tyr Ile Glu Ser
                800                 805                 810 ccc aac tac cct ggc gac tac cca gcc aac gct gaa tgc gtc tgg cac    2501
Pro Asn Tyr Pro Gly Asp Tyr Pro Ala Asn Ala Glu Cys Val Trp His
            815                 820                 825 atc gca cct ccc cca aag cgc agg atc ctc atc gtg gtc cct gag atc    2549
Ile Ala Pro Pro Pro Lys Arg Arg Ile Leu Ile Val Val Pro Glu Ile
        830                 835                 840 ttc ctg ccc atc gag gat gag tgc ggc gat gtt ctg gtc atg agg aag    2597
Phe Leu Pro Ile Glu Asp Glu Cys Gly Asp Val Leu Val Met Arg Lys
    845                 850                 855 agt gcc tct ccc acg tcc atc acc acc tat gag acc tgc cag acc tac    2645
Ser Ala Ser Pro Thr Ser Ile Thr Thr Tyr Glu Thr Cys Gln Thr Tyr
860                 865                 870                 875 gag agg ccc atc gcc ttc acc tcc cgc tcc cgc aag ctc tgg atc cag    2693
Glu Arg Pro Ile Ala Phe Thr Ser Arg Ser Arg Lys Leu Trp Ile Gln
                880                 885                 890 ttc aaa tcc aat gaa ggc aac agc ggc aaa ggc ttc caa gtg ccc tat    2741
Phe Lys Ser Asn Glu Gly Asn Ser Gly Lys Gly Phe Gln Val Pro Tyr
            895                 900                 905 gtc acc tac gat gag gac tac cag caa ctc ata gag gac atc gtg cgc    2789
Val Thr Tyr Asp Glu Asp Tyr Gln Gln Leu Ile Glu Asp Ile Val Arg
        910                 915                 920 gat ggg cgc ctg tac gcc tcg gag aac cac cag gaa att ttg aaa gac    2837
Asp Gly Arg Leu Tyr Ala Ser Glu Asn His Gln Glu Ile Leu Lys Asp
    925                 930                 935 aag aag ctg atc aag gcc ctc ttc gac gtg ctg gcg cat ccc cag aac    2885
Lys Lys Leu Ile Lys Ala Leu Phe Asp Val Leu Ala His Pro Gln Asn
940                 945                 950                 955 tac ttc aag tac aca gcc cag gaa tcc aag gag atg ttc cca cgg tcc    2933
Tyr Phe Lys Tyr Thr Ala Gln Glu Ser Lys Glu Met Phe Pro Arg Ser
                960                 965                 970 ttc atc aaa ctg ctg cgc tcc aaa gtg tct cgg ttc ctg cgg ccc tac    2981
Phe Ile Lys Leu Leu Arg Ser Lys Val Ser Arg Phe Leu Arg Pro Tyr
            975                 980                 985 aaa taa ccggg                                                      2992
Lys

<210> SEQ ID NO 2
<211> LENGTH: 988
<212> TYPE: PRT
<213> ORGANISM: Homo sapiens
```

<400> SEQUENCE: 2

```
Met Gly Ala Ala Ala Val Arg Trp His Leu Cys Val Leu Leu Ala Leu
1               5                   10                  15
Gly Thr Arg Gly Arg Leu Ala Gly Gly Ser Gly Leu Pro Gly Ser Val
            20                  25                  30
Asp Val Asp Glu Cys Ser Glu Gly Thr Asp Asp Cys His Ile Asp Ala
        35                  40                  45
Ile Cys Gln Asn Ala Pro Lys Ser Tyr Lys Cys Leu Cys Lys Pro Gly
    50                  55                  60
Tyr Lys Gly Glu Gly Lys Gln Cys Gly Asp Ile Asp Glu Cys Glu Asn
65                  70                  75                  80
Asp Tyr Tyr Asn Gly Gly Cys Val His Glu Cys Ile Asn Ile Pro Gly
                85                  90                  95
Asn Tyr Arg Cys Thr Cys Phe Asp Gly Phe Met Leu Ala His Asp Gly
            100                 105                 110
His Asn Cys Leu Asp Val Asp Glu Cys Gln Asp Asn Asn Gly Gly Cys
        115                 120                 125
Gln Gln Ile Cys Val Asn Ala Met Gly Ser Tyr Glu Cys Gln Cys His
    130                 135                 140
Ser Gly Phe Phe Leu Ser Asp Asn Gln His Thr Cys Ile His Arg Ser
145                 150                 155                 160
Asn Glu Gly Met Asn Cys Met Asn Lys Asp His Gly Cys Ala His Ile
                165                 170                 175
Cys Arg Glu Thr Pro Lys Gly Gly Val Ala Cys Asp Cys Arg Pro Gly
            180                 185                 190
Phe Asp Leu Ala Gln Asn Gln Lys Asp Cys Thr Leu Thr Cys Asn Tyr
        195                 200                 205
Gly Asn Gly Gly Cys Gln His Ser Cys Glu Asp Thr Asp Thr Gly Pro
    210                 215                 220
Thr Cys Gly Cys His Gln Lys Tyr Ala Pro His Ser Asp Gly Arg Thr
225                 230                 235                 240
Cys Ile Glu Thr Cys Ala Val Asn Asn Gly Gly Cys Asp Arg Thr Cys
                245                 250                 255
Lys Asp Thr Ala Thr Gly Val Arg Cys Ser Cys Pro Val Gly Phe Thr
            260                 265                 270
Leu Gln Pro Asp Gly Lys Thr Cys Lys Asp Ile Asn Glu Cys Leu Val
        275                 280                 285
Asn Asn Gly Gly Cys Asp His Phe Cys Arg Asn Thr Val Gly Ser Phe
    290                 295                 300
Glu Cys Gly Cys Arg Lys Gly Tyr Lys Leu Leu Thr Asp Glu Arg Thr
305                 310                 315                 320
Cys Gln Asp Ile Asp Glu Cys Ser Phe Glu Arg Thr Cys Asp His Ile
                325                 330                 335
Cys Ile Asn Ser Pro Gly Ser Phe Gln Cys Leu Cys His Arg Gly Tyr
            340                 345                 350
Ile Leu Tyr Gly Thr Thr His Cys Gly Asp Val Asp Glu Cys Ser Met
        355                 360                 365
Ser Asn Gly Ser Cys Asp Gln Gly Cys Val Asn Thr Lys Gly Ser Tyr
    370                 375                 380
Glu Cys Val Cys Pro Pro Gly Arg Arg Leu His Trp Asn Arg Lys Asp
385                 390                 395                 400
Cys Val Glu Thr Gly Lys Cys Leu Ser Arg Ala Lys Thr Ser Pro Arg
```

-continued

```
            405                 410                 415
Ala Gln Leu Ser Cys Ser Lys Ala Gly Val Glu Ser Cys Phe Leu
            420                 425                 430

Ser Cys Pro Ala His Thr Leu Phe Val Pro Asp Ser Glu Asn Ser Tyr
            435                 440                 445

Val Leu Ser Cys Gly Val Pro Gly Pro Gln Gly Lys Ala Leu Gln Lys
            450                 455                 460

Arg Asn Gly Thr Ser Ser Gly Leu Gly Pro Ser Cys Ser Asp Ala Pro
465                 470                 475                 480

Thr Thr Pro Ile Lys Gln Lys Ala Arg Phe Lys Ile Arg Asp Ala Lys
            485                 490                 495

Cys His Leu Arg Pro His Ser Gln Ala Arg Ala Lys Glu Thr Ala Arg
            500                 505                 510

Gln Pro Leu Leu Asp His Cys His Val Thr Phe Val Thr Leu Lys Cys
            515                 520                 525

Asp Ser Ser Lys Lys Arg Arg Arg Gly Arg Lys Ser Pro Ser Lys Glu
            530                 535                 540

Val Ser His Ile Thr Ala Glu Phe Glu Ile Glu Thr Lys Met Glu Glu
545                 550                 555                 560

Ala Ser Asp Thr Cys Glu Ala Asp Cys Leu Arg Lys Arg Ala Glu Gln
            565                 570                 575

Ser Leu Gln Ala Ala Ile Lys Thr Leu Arg Lys Ser Ile Gly Arg Gln
            580                 585                 590

Gln Phe Tyr Val Gln Val Ser Gly Thr Glu Tyr Glu Val Ala Gln Arg
            595                 600                 605

Pro Ala Lys Ala Leu Glu Gly Gln Gly Ala Cys Gly Ala Gly Gln Val
            610                 615                 620

Leu Gln Asp Ser Lys Cys Val Ala Cys Gly Pro Gly Thr His Phe Gly
625                 630                 635                 640

Gly Glu Leu Gly Gln Cys Val Pro Cys Met Pro Gly Thr Tyr Gln Asp
            645                 650                 655

Met Glu Gly Gln Leu Ser Cys Thr Pro Cys Pro Ser Ser Asp Gly Leu
            660                 665                 670

Gly Leu Pro Gly Ala Arg Asn Val Ser Glu Cys Gly Gly Gln Cys Ser
            675                 680                 685

Pro Gly Phe Phe Ser Ala Asp Gly Phe Lys Pro Cys Gln Ala Cys Pro
            690                 695                 700

Val Gly Thr Tyr Gln Pro Glu Pro Gly Arg Thr Gly Cys Phe Pro Cys
705                 710                 715                 720

Gly Gly Gly Leu Leu Thr Lys His Glu Gly Thr Thr Ser Phe Gln Asp
            725                 730                 735

Cys Glu Ala Lys Val His Cys Ser Pro Gly His His Tyr Asn Thr Thr
            740                 745                 750

Thr His Arg Cys Ile Arg Cys Pro Val Gly Thr Tyr Gln Pro Glu Phe
            755                 760                 765

Gly Gln Asn His Cys Ile Thr Cys Pro Gly Asn Thr Ser Thr Asp Phe
            770                 775                 780

Asp Gly Ser Thr Asn Val Thr His Cys Lys Asn Gln His Cys Gly Gly
785                 790                 795                 800

Glu Leu Gly Asp Tyr Thr Gly Tyr Ile Glu Ser Pro Asn Tyr Pro Gly
            805                 810                 815

Asp Tyr Pro Ala Asn Ala Glu Cys Val Trp His Ile Ala Pro Pro Pro
            820                 825                 830
```

```
Lys Arg Arg Ile Leu Ile Val Val Pro Glu Ile Phe Leu Pro Ile Glu
                835                 840                 845

Asp Glu Cys Gly Asp Val Leu Val Met Arg Lys Ser Ala Ser Pro Thr
    850                 855                 860

Ser Ile Thr Thr Tyr Glu Thr Cys Gln Thr Tyr Glu Arg Pro Ile Ala
865                 870                 875                 880

Phe Thr Ser Arg Ser Arg Lys Leu Trp Ile Gln Phe Lys Ser Asn Glu
                885                 890                 895

Gly Asn Ser Gly Lys Gly Phe Gln Val Pro Tyr Val Thr Tyr Asp Glu
            900                 905                 910

Asp Tyr Gln Gln Leu Ile Glu Asp Ile Val Arg Asp Gly Arg Leu Tyr
        915                 920                 925

Ala Ser Glu Asn His Gln Glu Ile Leu Lys Asp Lys Leu Ile Lys
    930                 935                 940

Ala Leu Phe Asp Val Leu Ala His Pro Gln Asn Tyr Phe Lys Tyr Thr
945                 950                 955                 960

Ala Gln Glu Ser Lys Glu Met Phe Pro Arg Ser Phe Ile Lys Leu Leu
                965                 970                 975

Arg Ser Lys Val Ser Arg Phe Leu Arg Pro Tyr Lys
            980                 985
```

```
<210> SEQ ID NO 3
<211> LENGTH: 3497
<212> TYPE: DNA
<213> ORGANISM: Homo sapiens
<220> FEATURE:
<221> NAME/KEY: CDS
<222> LOCATION: (81)..(2840)
<223> OTHER INFORMATION: SCUBE2

<400> SEQUENCE: 3
```

| | |
|---|---:|
| ggcgtccgcg cacacctccc cgcgccgccg ccgccaccgc ccgcactccg ccgcctctgc | 60 |

| | | |
|---|---|---:|
| ccgcaaccgc tgagccatcc atg ggg gtc gcg ggc cgc aac cgt ccc ggg gcg | | 113 |
| Met Gly Val Ala Gly Arg Asn Arg Pro Gly Ala | | |
| 1 5 10 | | |

| | | |
|---|---|---:|
| gcc tgg gcg gtg ctg ctg ctg ctg ctg ctg ccg cca ctg ctg ctg | | 161 |
| Ala Trp Ala Val Leu Leu Leu Leu Leu Leu Pro Pro Leu Leu Leu | | |
| 15 20 25 | | |

| | | |
|---|---|---:|
| ctg gcg ggg gcc gtc ccg ccg ggt cgg ggc cgt gcc gcg ggg ccg cag | | 209 |
| Leu Ala Gly Ala Val Pro Pro Gly Arg Gly Arg Ala Ala Gly Pro Gln | | |
| 30 35 40 | | |

| | | |
|---|---|---:|
| gag gat gta gat gag tgt gcc caa ggg cta gat gac tgc cat gcc gac | | 257 |
| Glu Asp Val Asp Glu Cys Ala Gln Gly Leu Asp Asp Cys His Ala Asp | | |
| 45 50 55 | | |

| | | |
|---|---|---:|
| gcc ctg tgt cag aac aca ccc acc tcc tac aag tgc tcc tgc aag cct | | 305 |
| Ala Leu Cys Gln Asn Thr Pro Thr Ser Tyr Lys Cys Ser Cys Lys Pro | | |
| 60 65 70 75 | | |

| | | |
|---|---|---:|
| ggc tac caa ggg gaa ggc agg cag tgt gag gac atc gat gaa tgt gga | | 353 |
| Gly Tyr Gln Gly Glu Gly Arg Gln Cys Glu Asp Ile Asp Glu Cys Gly | | |
| 80 85 90 | | |

| | | |
|---|---|---:|
| aat gag ctc aat gga ggc tgt gtc cat gac tgt ttg aat att cca ggc | | 401 |
| Asn Glu Leu Asn Gly Gly Cys Val His Asp Cys Leu Asn Ile Pro Gly | | |
| 95 100 105 | | |

| | | |
|---|---|---:|
| aat tat cgt tgc act tgt ttt gat ggc ttc atg ttg gct cat gac ggt | | 449 |
| Asn Tyr Arg Cys Thr Cys Phe Asp Gly Phe Met Leu Ala His Asp Gly | | |
| 110 115 120 | | |

| | | |
|---|---|---:|
| cat aat tgt ctt gat gtg gac gag tgc ctg gag aac aat ggc ggc tgc | | 497 |
| His Asn Cys Leu Asp Val Asp Glu Cys Leu Glu Asn Asn Gly Gly Cys | | |

-continued

```
            125                 130                 135
cag cat acc tgt gtc aac gtc atg ggg agc tat gag tgc tgc tgc aag      545
Gln His Thr Cys Val Asn Val Met Gly Ser Tyr Glu Cys Cys Cys Lys
140                 145                 150                 155 gag ggg ttt ttc ctg agt gac aat cag cac acc tgc att cac cgc tcg      593
Glu Gly Phe Phe Leu Ser Asp Asn Gln His Thr Cys Ile His Arg Ser
                160                 165                 170 gaa gag ggc ctg agc tgc atg aat aag gat cac ggc tgt agt cac atc      641
Glu Glu Gly Leu Ser Cys Met Asn Lys Asp His Gly Cys Ser His Ile
        175                 180                 185 tgc aag gag gcc cca agg ggc agc gtc gcc tgt gag tgc agg cct ggt      689
Cys Lys Glu Ala Pro Arg Gly Ser Val Ala Cys Glu Cys Arg Pro Gly
                190                 195                 200 ttt gag ctg gcc aag aac cag aga gac tgc atc ttg acc tgt aac cat      737
Phe Glu Leu Ala Lys Asn Gln Arg Asp Cys Ile Leu Thr Cys Asn His
        205                 210                 215 ggg aac ggt ggg tgc cag cac tcc tgt gac gat aca gcc gat ggc cca      785
Gly Asn Gly Gly Cys Gln His Ser Cys Asp Asp Thr Ala Asp Gly Pro
220                 225                 230                 235 gag tgc agc tgc cat cca cag tac aag atg cac aca gat ggg agg agc      833
Glu Cys Ser Cys His Pro Gln Tyr Lys Met His Thr Asp Gly Arg Ser
                240                 245                 250 tgc ctt gag cga gag gac act gtc ctg gag gtg aca gag agc aac acc      881
Cys Leu Glu Arg Glu Asp Thr Val Leu Glu Val Thr Glu Ser Asn Thr
        255                 260                 265 aca tca gtg gtg gat ggg gat aaa cgg gtg aaa cgg cgg ctc ctc atg      929
Thr Ser Val Val Asp Gly Asp Lys Arg Val Lys Arg Arg Leu Leu Met
270                 275                 280 gaa acg tgt gct gtc aac aat gga ggc tgt gac cgc acc tgt aag gat      977
Glu Thr Cys Ala Val Asn Asn Gly Gly Cys Asp Arg Thr Cys Lys Asp
285                 290                 295 act tcg aca ggt gtc cac tgc agt tgt cct gtt gga ttc act ctc cag     1025
Thr Ser Thr Gly Val His Cys Ser Cys Pro Val Gly Phe Thr Leu Gln
300                 305                 310                 315 ttg gat ggg aag aca tgt aaa gat att gat gag tgc agg acc cgc aat     1073
Leu Asp Gly Lys Thr Cys Lys Asp Ile Asp Glu Cys Gln Thr Arg Asn
                320                 325                 330 gga ggt tgt gat cat ttc tgc aaa aac atc gtg ggc agt ttt gac tgc     1121
Gly Gly Cys Asp His Phe Cys Lys Asn Ile Val Gly Ser Phe Asp Cys
        335                 340                 345 ggc tgc aag aaa gga ttt aaa tta tta aca gat gag aag tct tgc caa     1169
Gly Cys Lys Lys Gly Phe Lys Leu Leu Thr Asp Glu Lys Ser Cys Gln
                350                 355                 360 gat gtg gat gag tgc tct ttg gat agg acc tgt gac cac agc tgc atc     1217
Asp Val Asp Glu Cys Ser Leu Asp Arg Thr Cys Asp His Ser Cys Ile
365                 370                 375 aac cac cct ggc aca ttt gct tgt gct tgc aac cga ggg tac acc ctg     1265
Asn His Pro Gly Thr Phe Ala Cys Ala Cys Asn Arg Gly Tyr Thr Leu
380                 385                 390                 395 tat ggc ttc acc cac tgt gga gac gtc acc acc atc agg aca agt gta     1313
Tyr Gly Phe Thr His Cys Gly Asp Val Thr Thr Ile Arg Thr Ser Val
                400                 405                 410 acc ttt aag cta aat gaa ggc aag tgt agt ttg aaa aat gct gag ctg     1361
Thr Phe Lys Leu Asn Glu Gly Lys Cys Ser Leu Lys Asn Ala Glu Leu
        415                 420                 425 ttt ccc gag ggt ctg cga cca gca cta cca gag aag cac agc tca gta     1409
Phe Pro Glu Gly Leu Arg Pro Ala Leu Pro Glu Lys His Ser Ser Val
                430                 435                 440 aaa gag agc ttc cgc tac gta aac ctt aca tgc agc tct ggc aag caa     1457
```

```
                Lys Glu Ser Phe Arg Tyr Val Asn Leu Thr Cys Ser Ser Gly Lys Gln
                    445                 450                 455 gtc cca gga gcc cct ggc cga cca agc acc cct aag gaa atg ttt atc        1505
Val Pro Gly Ala Pro Gly Arg Pro Ser Thr Pro Lys Glu Met Phe Ile
460                 465                 470                 475 act gtt gag ttt gag ctt gaa act aac caa aag gag gtg aca gct tct        1553
Thr Val Glu Phe Glu Leu Glu Thr Asn Gln Lys Glu Val Thr Ala Ser
                    480                 485                 490 tgt gac ctg agc tgc atc gta aag cga acc gag aag cgg ctc cgt aaa        1601
Cys Asp Leu Ser Cys Ile Val Lys Arg Thr Glu Lys Arg Leu Arg Lys
                495                 500                 505 gcc atc cgc acg ctc aga aag gcc gtc cac agg gag cag ttt cac ctc        1649
Ala Ile Arg Thr Leu Arg Lys Ala Val His Arg Glu Gln Phe His Leu
        510                 515                 520 cag ctc tca ggc atg aac ctc gac gtg gct aaa aag cct ccc aga aca        1697
Gln Leu Ser Gly Met Asn Leu Asp Val Ala Lys Lys Pro Pro Arg Thr
    525                 530                 535 tct gaa cgc cag gca gag tcc tgt gga gtg ggc cag ggt cat gca gaa        1745
Ser Glu Arg Gln Ala Glu Ser Cys Gly Val Gly Gln Gly His Ala Glu
540                 545                 550                 555 aac caa tgt gtc agt tgc agg gct ggg acc tat tat gat gga gca cga        1793
Asn Gln Cys Val Ser Cys Arg Ala Gly Thr Tyr Tyr Asp Gly Ala Arg
                560                 565                 570 gaa cgc tgc att tta tgt cca aat gga acc ttc caa aat gag gaa gga        1841
Glu Arg Cys Ile Leu Cys Pro Asn Gly Thr Phe Gln Asn Glu Glu Gly
                575                 580                 585 caa atg act tgt gaa cca tgc cca aga cca gga aat tct ggg gcc ctg        1889
Gln Met Thr Cys Glu Pro Cys Pro Arg Pro Gly Asn Ser Gly Ala Leu
                590                 595                 600 aag acc cca gaa gct tgg aat atg tct gaa tgt gga ggt ctg tgt caa        1937
Lys Thr Pro Glu Ala Trp Asn Met Ser Glu Cys Gly Gly Leu Cys Gln
605                 610                 615 cct ggt gaa tat tct gca gat ggc ttt gca cct tgc cag ctc tgt gcc        1985
Pro Gly Glu Tyr Ser Ala Asp Gly Phe Ala Pro Cys Gln Leu Cys Ala
620                 625                 630                 635 ctg ggc acg ttc cag cct gaa gct ggt cga act tcc tgc ttc ccc tgt        2033
Leu Gly Thr Phe Gln Pro Glu Ala Gly Arg Thr Ser Cys Phe Pro Cys
                640                 645                 650 gga gga ggc ctt gcc acc aaa cat cag gga gct act tcc ttt cag gac        2081
Gly Gly Gly Leu Ala Thr Lys His Gln Gly Ala Thr Ser Phe Gln Asp
                655                 660                 665 tgt gaa acc aga gtt caa tgt tca cct gga cat ttc tac aac acc acc        2129
Cys Glu Thr Arg Val Gln Cys Ser Pro Gly His Phe Tyr Asn Thr Thr
                670                 675                 680 act cac cga tgt att cgt tgc cca gtg gga aca tac cag cct gaa ttt        2177
Thr His Arg Cys Ile Arg Cys Pro Val Gly Thr Tyr Gln Pro Glu Phe
        685                 690                 695 gga aaa aat aat tgt gtt tct tgc cca gga aat act acg act gac ttt        2225
Gly Lys Asn Asn Cys Val Ser Cys Pro Gly Asn Thr Thr Thr Asp Phe
700                 705                 710                 715 gat ggc tcc aca aac ata acc cag tgt aaa aac aga aga tgt gga ggg        2273
Asp Gly Ser Thr Asn Ile Thr Gln Cys Lys Asn Arg Arg Cys Gly Gly
                720                 725                 730 gag ctg gga gat ttc act ggg tac att gaa tcc cca aac tac cca ggc        2321
Glu Leu Gly Asp Phe Thr Gly Tyr Ile Glu Ser Pro Asn Tyr Pro Gly
                735                 740                 745 aat tac cca gcc aac acc gag tgt acg tgg acc atc aac cca ccc ccc        2369
Asn Tyr Pro Ala Asn Thr Glu Cys Thr Trp Thr Ile Asn Pro Pro Pro
                750                 755                 760
```

```
aag cgc cgc atc ctg atc gtg gtc cct gag atc ttc ctg ccc ata gag    2417
Lys Arg Arg Ile Leu Ile Val Val Pro Glu Ile Phe Leu Pro Ile Glu
    765                 770                 775 gac gac tgt ggg gac tat ctg gtg atg cgg aaa acc tct tca tcc aat    2465
Asp Asp Cys Gly Asp Tyr Leu Val Met Arg Lys Thr Ser Ser Ser Asn
780                 785                 790                 795 tct gtg aca aca tat gaa acc tgc cag acc tac gaa cgc ccc atc gcc    2513
Ser Val Thr Thr Tyr Glu Thr Cys Gln Thr Tyr Glu Arg Pro Ile Ala
                800                 805                 810 ttc acc tcc agg tca aag aag ctg tgg att cag ttc aag tcc aat gaa    2561
Phe Thr Ser Arg Ser Lys Lys Leu Trp Ile Gln Phe Lys Ser Asn Glu
            815                 820                 825 ggg aac agc gct aga ggg ttc cag gtc cca tac gtg aca tat gat gag    2609
Gly Asn Ser Ala Arg Gly Phe Gln Val Pro Tyr Val Thr Tyr Asp Glu
        830                 835                 840 gac tac cag gaa ctc att gaa gac ata gtt cga gat ggc agg ctc tat    2657
Asp Tyr Gln Glu Leu Ile Glu Asp Ile Val Arg Asp Gly Arg Leu Tyr
    845                 850                 855 gca tct gag aac cat cag gaa ata ctt aag gat aag aaa ctt atc aag    2705
Ala Ser Glu Asn His Gln Glu Ile Leu Lys Asp Lys Lys Leu Ile Lys
860                 865                 870                 875 gct ctg ttt gat gtc ctg gcc cat ccc cag aac tat ttc aag tac aca    2753
Ala Leu Phe Asp Val Leu Ala His Pro Gln Asn Tyr Phe Lys Tyr Thr
                880                 885                 890 gcc cag gag tcc cga gag atg ttt cca aga tcg ttc atc cga ttg cta    2801
Ala Gln Glu Ser Arg Glu Met Phe Pro Arg Ser Phe Ile Arg Leu Leu
            895                 900                 905 cgt tcc aaa gtg tcc agg ttt ttg aga cct tac aaa tga ctcagcccac    2850
Arg Ser Lys Val Ser Arg Phe Leu Arg Pro Tyr Lys
        910                 915 gtgccactca atacaaatgt tctgctatag ggttggtggg acagagctgt cttccttctg    2910
catgtcagca cagtcgggta ttgctgcctc ccgtatcagt gactcattag agttcaattt    2970
ttatagataa tacagatatt ttggtaaatt gaacttggtt tttctttccc agcatcgtgg    3030
atgtagactg agaatggctt tgagtggcat cagcttctca ctgctgtggg cggatgtctt    3090
ggatagatca cgggctggct gagctggact ttggtcagcc taggtgagac tcacctgtcc    3150
ttctggggtc ttactcctcc tcaaggagtc tgtagtggaa aggaggccac agaataagct    3210
gcttattctg aaacttcagc ttcctctagc ccggccctct ctaagggagc cctctgcact    3270
cgtgtgcagg ctctgaccag gcagaacagg caagaggggga gggaaggaga ccctgcagg    3330 ctccctccac ccaccttgag acctgggagg actcagtttc tccacagcct tctccagcct    3390
gtgtgataca gtttgatcc caggaacttg agttctaagc agtgctcgtg aaaaaaaaa    3450 gcagaaagaa ttagaaataa ataaaaacta agcacttctg gagacat                 3497
```

<210> SEQ ID NO 4
<211> LENGTH: 919
<212> TYPE: PRT
<213> ORGANISM: Homo sapiens

<400> SEQUENCE: 4

Met Gly Val Ala Gly Arg Asn Arg Pro Gly Ala Ala Trp Ala Val Leu
1               5                   10                  15

Leu Leu Leu Leu Leu Leu Pro Pro Leu Leu Leu Ala Gly Ala Val
            20                  25                  30

Pro Pro Gly Arg Gly Arg Ala Ala Gly Pro Gln Glu Asp Val Asp Glu
        35                  40                  45

-continued

```
Cys Ala Gln Gly Leu Asp Asp Cys His Ala Asp Ala Leu Cys Gln Asn
 50                  55                  60
Thr Pro Thr Ser Tyr Lys Cys Ser Cys Lys Pro Gly Tyr Gln Gly Glu
 65                      70                  75                  80
Gly Arg Gln Cys Glu Asp Ile Asp Glu Cys Gly Asn Glu Leu Asn Gly
                 85                  90                  95
Gly Cys Val His Asp Cys Leu Asn Ile Pro Gly Asn Tyr Arg Cys Thr
            100                 105                 110
Cys Phe Asp Gly Phe Met Leu Ala His Asp Gly His Asn Cys Leu Asp
            115                 120                 125
Val Asp Glu Cys Leu Glu Asn Asn Gly Gly Cys Gln His Thr Cys Val
130                 135                 140
Asn Val Met Gly Ser Tyr Glu Cys Cys Lys Glu Gly Phe Phe Leu
145                 150                 155                 160
Ser Asp Asn Gln His Thr Cys Ile His Arg Ser Glu Glu Gly Leu Ser
                165                 170                 175
Cys Met Asn Lys Asp His Gly Cys Ser His Ile Cys Lys Glu Ala Pro
            180                 185                 190
Arg Gly Ser Val Ala Cys Glu Cys Arg Pro Gly Phe Glu Leu Ala Lys
            195                 200                 205
Asn Gln Arg Asp Cys Ile Leu Thr Cys Asn His Gly Asn Gly Gly Cys
210                 215                 220
Gln His Ser Cys Asp Asp Thr Ala Asp Gly Pro Glu Cys Ser Cys His
225                 230                 235                 240
Pro Gln Tyr Lys Met His Thr Asp Gly Arg Ser Cys Leu Glu Arg Glu
                245                 250                 255
Asp Thr Val Leu Glu Val Thr Glu Ser Asn Thr Thr Ser Val Val Asp
            260                 265                 270
Gly Asp Lys Arg Val Lys Arg Leu Leu Met Glu Thr Cys Ala Val
            275                 280                 285
Asn Asn Gly Gly Cys Asp Arg Thr Cys Lys Asp Thr Ser Thr Gly Val
290                 295                 300
His Cys Ser Cys Pro Val Gly Phe Thr Leu Gln Leu Asp Gly Lys Thr
305                 310                 315                 320
Cys Lys Asp Ile Asp Glu Cys Gln Thr Arg Asn Gly Gly Cys Asp His
                325                 330                 335
Phe Cys Lys Asn Ile Val Gly Ser Phe Asp Cys Gly Cys Lys Lys Gly
            340                 345                 350
Phe Lys Leu Leu Thr Asp Glu Lys Ser Cys Gln Asp Val Asp Glu Cys
            355                 360                 365
Ser Leu Asp Arg Thr Cys Asp His Ser Cys Ile Asn His Pro Gly Thr
370                 375                 380
Phe Ala Cys Ala Cys Asn Arg Gly Tyr Thr Leu Tyr Gly Phe Thr His
385                 390                 395                 400
Cys Gly Asp Val Thr Thr Ile Arg Thr Ser Val Thr Phe Lys Leu Asn
                405                 410                 415
Glu Gly Lys Cys Ser Leu Lys Asn Ala Glu Leu Phe Pro Glu Gly Leu
            420                 425                 430
Arg Pro Ala Leu Pro Glu Lys His Ser Ser Val Lys Glu Ser Phe Arg
            435                 440                 445
Tyr Val Asn Leu Thr Cys Ser Ser Gly Lys Gln Val Pro Gly Ala Pro
450                 455                 460
Gly Arg Pro Ser Thr Pro Lys Glu Met Phe Ile Thr Val Glu Phe Glu
```

-continued

```
        465                 470                 475                 480
Leu Glu Thr Asn Gln Lys Glu Val Thr Ala Ser Cys Asp Leu Ser Cys
                    485                 490                 495

Ile Val Lys Arg Thr Glu Lys Arg Leu Arg Lys Ala Ile Arg Thr Leu
                500                 505                 510

Arg Lys Ala Val His Arg Glu Gln Phe His Leu Gln Leu Ser Gly Met
            515                 520                 525

Asn Leu Asp Val Ala Lys Lys Pro Arg Thr Ser Glu Arg Gln Ala
        530                 535                 540

Glu Ser Cys Gly Val Gly Gln Gly His Ala Glu Asn Gln Cys Val Ser
545                 550                 555                 560

Cys Arg Ala Gly Thr Tyr Tyr Asp Gly Ala Arg Glu Arg Cys Ile Leu
                565                 570                 575

Cys Pro Asn Gly Thr Phe Gln Asn Glu Glu Gly Gln Met Thr Cys Glu
                580                 585                 590

Pro Cys Pro Arg Pro Gly Asn Ser Gly Ala Leu Lys Thr Pro Glu Ala
                595                 600                 605

Trp Asn Met Ser Glu Cys Gly Gly Leu Cys Gln Pro Gly Glu Tyr Ser
        610                 615                 620

Ala Asp Gly Phe Ala Pro Cys Gln Leu Cys Ala Leu Gly Thr Phe Gln
625                 630                 635                 640

Pro Glu Ala Gly Arg Thr Ser Cys Phe Pro Cys Gly Gly Gly Leu Ala
                645                 650                 655

Thr Lys His Gln Gly Ala Thr Ser Phe Gln Asp Cys Glu Thr Arg Val
                660                 665                 670

Gln Cys Ser Pro Gly His Phe Tyr Asn Thr Thr Thr His Arg Cys Ile
            675                 680                 685

Arg Cys Pro Val Gly Thr Tyr Gln Pro Glu Phe Gly Lys Asn Asn Cys
        690                 695                 700

Val Ser Cys Pro Gly Asn Thr Thr Asp Phe Asp Gly Ser Thr Asn
705                 710                 715                 720

Ile Thr Gln Cys Lys Asn Arg Arg Cys Gly Gly Glu Leu Gly Asp Phe
                725                 730                 735

Thr Gly Tyr Ile Glu Ser Pro Asn Tyr Pro Gly Asn Tyr Pro Ala Asn
                740                 745                 750

Thr Glu Cys Thr Trp Thr Ile Asn Pro Pro Lys Arg Arg Ile Leu
            755                 760                 765

Ile Val Val Pro Glu Ile Phe Leu Pro Ile Glu Asp Asp Cys Gly Asp
        770                 775                 780

Tyr Leu Val Met Arg Lys Thr Ser Ser Ser Asn Ser Val Thr Thr Tyr
785                 790                 795                 800

Glu Thr Cys Gln Thr Tyr Glu Arg Pro Ile Ala Phe Thr Ser Arg Ser
                805                 810                 815

Lys Lys Leu Trp Ile Gln Phe Lys Ser Asn Glu Gly Asn Ser Ala Arg
                820                 825                 830

Gly Phe Gln Val Pro Tyr Val Thr Tyr Asp Glu Asp Tyr Gln Glu Leu
            835                 840                 845

Ile Glu Asp Ile Val Arg Asp Gly Arg Leu Tyr Ala Ser Glu Asn His
        850                 855                 860

Gln Glu Ile Leu Lys Asp Lys Lys Leu Ile Lys Ala Leu Phe Asp Val
865                 870                 875                 880

Leu Ala His Pro Gln Asn Tyr Phe Lys Tyr Thr Ala Gln Glu Ser Arg
                885                 890                 895
```

```
Glu Met Phe Pro Arg Ser Phe Ile Arg Leu Leu Arg Ser Lys Val Ser
                900                 905                 910
Arg Phe Leu Arg Pro Tyr Lys
        915

<210> SEQ ID NO 5
<211> LENGTH: 3193
<212> TYPE: DNA
<213> ORGANISM: Homo sapiens
<220> FEATURE:
<221> NAME/KEY: CDS
<222> LOCATION: (449)...(3190)

<400> SEQUENCE: 5
cagcggcccg gcagcctggg gaggggggcca ccgcgcccgg gcgcgcaggg ggagcggcca      60
ccgcgccgag gccccatttg aaagaaaaaa gggcacgaaa aaggaggtgg tggagaagga     120
ggaggaggag gaggaggagg aggggagga ggaagaaaac gaaaaggagc gaggagagga     180
ggagaaagag gaggaggagg agaaaggcga agaaaaagag cctgagagac ggagaaagag     240
cgagagagga agaaagagag gcagaaaggg cgtgtttctg gcgctgcgtt tcccctcccc     300
tttctcaggt ccttcgctcg ggctctgcgc gctctccggc tgcagctctc tcccggcgaa     360
gctgggaatt ggctgggatc cggccggctt ccgccctccc ctggccgcga gaccggcccc     420
ggcggctggg ccgccagtag ctccagcc atg ggc tcg ggg cgc gta ccc ggg        472
                                Met Gly Ser Gly Arg Val Pro Gly
                                  1               5 ctc tgc ctg ctt gtc ctg ctg gtc cac gcc cgc gcc gcc cag tac agc        520
Leu Cys Leu Leu Val Leu Leu Val His Ala Arg Ala Ala Gln Tyr Ser
     10                  15                  20 aaa gcc gcg caa gat gtg gat gag tgt gtg gag ggg act gac aac tgc       568
Lys Ala Ala Gln Asp Val Asp Glu Cys Val Glu Gly Thr Asp Asn Cys
 25                  30                  35                  40 cac atc gat gct atc tgc cag aac acc ccg agg tca tac aag tgc atc       616
His Ile Asp Ala Ile Cys Gln Asn Thr Pro Arg Ser Tyr Lys Cys Ile
                 45                  50                  55 tgc aag tct ggc tac aca ggg gac ggc aaa cac tgc aaa gac gtg gat       664
Cys Lys Ser Gly Tyr Thr Gly Asp Gly Lys His Cys Lys Asp Val Asp
             60                  65                  70 gag tgc gag cga gag gat aat gca ggt tgt gtg cat gac tgt gtc aac       712
Glu Cys Glu Arg Glu Asp Asn Ala Gly Cys Val His Asp Cys Val Asn
         75                  80                  85 atc cct ggc aat tac cgg tgt acc tgc tat gat gga ttc cac ctg gca       760
Ile Pro Gly Asn Tyr Arg Cys Thr Cys Tyr Asp Gly Phe His Leu Ala
     90                  95                 100 cat gac gga cac aac tgt ctg gat gtg gac gag tgt gcc gag ggc aac       808
His Asp Gly His Asn Cys Leu Asp Val Asp Glu Cys Ala Glu Gly Asn
105                 110                 115                 120 ggc ggc tgt cag cag agc tgt gtc aac atg atg ggc agc tat gag tgc       856
Gly Gly Cys Gln Gln Ser Cys Val Asn Met Met Gly Ser Tyr Glu Cys
                125                 130                 135 cac tgc cgg gaa ggc ttc ttc ctc agc gac aac cag cat acc tgt atc       904
His Cys Arg Glu Gly Phe Phe Leu Ser Asp Asn Gln His Thr Cys Ile
            140                 145                 150 cag cgg cca gaa gaa gga atg aat tgc atg aac aag aac cac ggc tgt       952
Gln Arg Pro Glu Glu Gly Met Asn Cys Met Asn Lys Asn His Gly Cys
        155                 160                 165 gcc cac att tgc cgg gag aca ccc aag ggg ggt att gcc tgt gaa tgc      1000
Ala His Ile Cys Arg Glu Thr Pro Lys Gly Gly Ile Ala Cys Glu Cys
    170                 175                 180
```

-continued

| | | |
|---|---|---|
| cgt cct ggc ttt gag ctt acc aag aac caa cgg gac tgt aaa tgt gag<br>Arg Pro Gly Phe Glu Leu Thr Lys Asn Gln Arg Asp Cys Lys Cys Glu<br>185                    190                    195                    200 | 1048 |
| ata att ggg atg gca gtg aca tgc aac tat ggt aac ggc ggc tgc cag<br>Ile Ile Gly Met Ala Val Thr Cys Asn Tyr Gly Asn Gly Gly Cys Gln<br>                    205                    210                    215 | 1096 |
| cac acg tgt gat gac aca gag cag ggt ccc cgg tgc ggc tgc cat atc<br>His Thr Cys Asp Asp Thr Glu Gln Gly Pro Arg Cys Gly Cys His Ile<br>    220                    225                    230 | 1144 |
| aag ttt gtg ctc cat acc gac ggg aag aca tgc atc gag acc tgt gct<br>Lys Phe Val Leu His Thr Asp Gly Lys Thr Cys Ile Glu Thr Cys Ala<br>        235                    240                    245 | 1192 |
| gtc aac aac ggg ggc tgt gac agt aag tgc cat gat gca gcg act ggt<br>Val Asn Asn Gly Gly Cys Asp Ser Lys Cys His Asp Ala Ala Thr Gly<br>250                    255                    260 | 1240 |
| gtc cac tgc acc tgc cct gtg ggc ttc atg ctg cag cca gac agg aag<br>Val His Cys Thr Cys Pro Val Gly Phe Met Leu Gln Pro Asp Arg Lys<br>265                    270                    275                    280 | 1288 |
| acg tgc aaa gat ata gat gag tgc cgc tta aac aac ggg ggc tgt gac<br>Thr Cys Lys Asp Ile Asp Glu Cys Arg Leu Asn Asn Gly Gly Cys Asp<br>                    285                    290                    295 | 1336 |
| cat att tgc cgc aac aca gtg ggc agc ttc gaa tgc agt tgc aag aaa<br>His Ile Cys Arg Asn Thr Val Gly Ser Phe Glu Cys Ser Cys Lys Lys<br>    300                    305                    310 | 1384 |
| ggc tat aag ctt ctc atc aat gag agg aac tgc cag gat ata gac gag<br>Gly Tyr Lys Leu Leu Ile Asn Glu Arg Asn Cys Gln Asp Ile Asp Glu<br>        315                    320                    325 | 1432 |
| tgt tcc ttt gat cga acc tgt gac cac ata tgt gtc aac aca cca gga<br>Cys Ser Phe Asp Arg Thr Cys Asp His Ile Cys Val Asn Thr Pro Gly<br>330                    335                    340 | 1480 |
| agc ttc cag tgt ctc tgc cat cgt ggc tac ctg ttg tat ggt atc acc<br>Ser Phe Gln Cys Leu Cys His Arg Gly Tyr Leu Leu Tyr Gly Ile Thr<br>345                    350                    355                    360 | 1528 |
| cac tgt ggg gat gtg gat gaa tgc agc atc aac cgg gga ggt tgc cgc<br>His Cys Gly Asp Val Asp Glu Cys Ser Ile Asn Arg Gly Gly Cys Arg<br>                    365                    370                    375 | 1576 |
| ttt ggc tgc atc aac act cct ggc agc tac cag tgt acc tgc cca gca<br>Phe Gly Cys Ile Asn Thr Pro Gly Ser Tyr Gln Cys Thr Cys Pro Ala<br>    380                    385                    390 | 1624 |
| ggc cag ggt cgg ctg cac tgg aat ggc aaa gat tgc aca gag cca ctg<br>Gly Gln Gly Arg Leu His Trp Asn Gly Lys Asp Cys Thr Glu Pro Leu<br>        395                    400                    405 | 1672 |
| aag tgt cag ggc agt cct ggg gcc tcg aaa gcc atg ctc agc tgc aac<br>Lys Cys Gln Gly Ser Pro Gly Ala Ser Lys Ala Met Leu Ser Cys Asn<br>410                    415                    420 | 1720 |
| cgg tct ggc aag aag gac acc tgt gcc ctg acc tgt ccc tcc agg gcc<br>Arg Ser Gly Lys Lys Asp Thr Cys Ala Leu Thr Cys Pro Ser Arg Ala<br>425                    430                    435                    440 | 1768 |
| cga ttt ttg cca gag tct gag aat ggc ttc acg gtg agc tgt ggg acc<br>Arg Phe Leu Pro Glu Ser Glu Asn Gly Phe Thr Val Ser Cys Gly Thr<br>                    445                    450                    455 | 1816 |
| ccc agc ccc agg gct gct cca gcc cga gct ggc cac aat ggg aac agc<br>Pro Ser Pro Arg Ala Ala Pro Ala Arg Ala Gly His Asn Gly Asn Ser<br>    460                    465                    470 | 1864 |
| acc aac tcc aac cac tgc cat ggt ggt gcc ccc tgc tct gaa tgc cag<br>Thr Asn Ser Asn His Cys His Gly Gly Ala Pro Cys Ser Glu Cys Gln<br>        475                    480                    485 | 1912 |
| gtc acc ttc atc cac ctt aag tgt gac tcc tct cgg aag ggc aag ggc<br>Val Thr Phe Ile His Leu Lys Cys Asp Ser Ser Arg Lys Gly Lys Gly | 1960 |

-continued

|  |  |
|---|---|
| cga cgg gcc cgg acc cct cca ggc aaa gag gtc aca agg ctc acc ctg<br>Arg Arg Ala Arg Thr Pro Pro Gly Lys Glu Val Thr Arg Leu Thr Leu<br>505                      510                      515                      520 | 2008 |
| gaa ctg gag gca gag caa ctc ttt ctc ctc cct gat aca cac ggc cat<br>Glu Leu Glu Ala Glu Gln Leu Phe Leu Leu Pro Asp Thr His Gly His<br>                        525                      530                      535 | 2056 |
| cca cca cca gcc agc tgt ggg ctg ccc tgc ctc cga cag cga atg gaa<br>Pro Pro Pro Ala Ser Cys Gly Leu Pro Cys Leu Arg Gln Arg Met Glu<br>540                      545                      550 | 2104 |
| cgg cgg ctg aaa gga tcc ctg aag atg ctc aga aag tcc atc aac cag<br>Arg Arg Leu Lys Gly Ser Leu Lys Met Leu Arg Lys Ser Ile Asn Gln<br>              555                      560                      565 | 2152 |
| gac cgc ttc ctg ctg cgc ctg gca ggc ctt gat tat gag ctg gcc cac<br>Asp Arg Phe Leu Leu Arg Leu Ala Gly Leu Asp Tyr Glu Leu Ala His<br>570                      575                      580 | 2200 |
| aag ccg ggc ctg gta gcc ggg gag cga tca gag act aat gac cac tgt<br>Lys Pro Gly Leu Val Ala Gly Glu Arg Ser Glu Thr Asn Asp His Cys<br>585                      590                      595                      600 | 2248 |
| act ccc gga cac aac aac gcc acc acc aat tca ggt cag tgc cca cct<br>Thr Pro Gly His Asn Asn Ala Thr Thr Asn Ser Gly Gln Cys Pro Pro<br>              605                      610                      615 | 2296 |
| ggc caa cac tct gta gat ggg ttc aag ccc tgt cag cca tgc cca cgt<br>Gly Gln His Ser Val Asp Gly Phe Lys Pro Cys Gln Pro Cys Pro Arg<br>620                      625                      630 | 2344 |
| ggc acc tac caa cct gaa gca gga cgg acc cta tgc ttc cct tgt ggt<br>Gly Thr Tyr Gln Pro Glu Ala Gly Arg Thr Leu Cys Phe Pro Cys Gly<br>              635                      640                      645 | 2392 |
| ggg ggc ctc acc acc aag cat gaa ggg gcc att tcc ttc caa gac tgt<br>Gly Gly Leu Thr Thr Lys His Glu Gly Ala Ile Ser Phe Gln Asp Cys<br>650                      655                      660 | 2440 |
| gac acc aaa gtc cag tgc tcc cca ggg cac tac tac aac acc agc atc<br>Asp Thr Lys Val Gln Cys Ser Pro Gly His Tyr Tyr Asn Thr Ser Ile<br>665                      670                      675                      680 | 2488 |
| cac cgc tgt att cgc tgt gcc atg ggc tcc tat cag ccc gac ttc cgt<br>His Arg Cys Ile Arg Cys Ala Met Gly Ser Tyr Gln Pro Asp Phe Arg<br>              685                      690                      695 | 2536 |
| cag aac ttc tgc agc cgc tgt cca gga aac aca agc aca gac ttt gat<br>Gln Asn Phe Cys Ser Arg Cys Pro Gly Asn Thr Ser Thr Asp Phe Asp<br>700                      705                      710 | 2584 |
| ggc tct acc agt gtg gcc caa tgc aag aat cgt cag tgt ggt ggg gag<br>Gly Ser Thr Ser Val Ala Gln Cys Lys Asn Arg Gln Cys Gly Gly Glu<br>              715                      720                      725 | 2632 |
| ctg ggt gag ttc act ggc tat att gag tcc ccc aac tac ccg ggc aac<br>Leu Gly Glu Phe Thr Gly Tyr Ile Glu Ser Pro Asn Tyr Pro Gly Asn<br>730                      735                      740 | 2680 |
| tac cca gct ggt gtg gag tgc atc tgg aac atc aac ccc cca ccc aag<br>Tyr Pro Ala Gly Val Glu Cys Ile Trp Asn Ile Asn Pro Pro Pro Lys<br>745                      750                      755                      760 | 2728 |
| cgc aag atc ctt atc gtg gta cca gag atc ttc ctg cca tct gag gat<br>Arg Lys Ile Leu Ile Val Val Pro Glu Ile Phe Leu Pro Ser Glu Asp<br>              765                      770                      775 | 2776 |
| gag tgt ggg gac gtc ctc gtc atg aga aag aac tca tcc cca tcc tcc<br>Glu Cys Gly Asp Val Leu Val Met Arg Lys Asn Ser Ser Pro Ser Ser<br>780                      785                      790 | 2824 |
| att acc act tat gag acc tgc cag acc tac gag cgt ccc att gcc ttc<br>Ile Thr Thr Tyr Glu Thr Cys Gln Thr Tyr Glu Arg Pro Ile Ala Phe<br>              795                      800                      805 | 2872 |
| act gcc cgt tcc agg aag ctc tgg atc aac ttc aag aca agc gag gcc | 2920 |

```
Thr Ala Arg Ser Arg Lys Leu Trp Ile Asn Phe Lys Thr Ser Glu Ala
    810                 815                 820 aac agc gcc cgt ggc ttc cag att ccc tat gtt acc tat gat gag gac    2968
Asn Ser Ala Arg Gly Phe Gln Ile Pro Tyr Val Thr Tyr Asp Glu Asp
825                 830                 835                 840 tat gag cag ctg gta gaa gac att gtg cga gat ggc cgg ctc tat gcc    3016
Tyr Glu Gln Leu Val Glu Asp Ile Val Arg Asp Gly Arg Leu Tyr Ala
                845                 850                 855 tct gaa aac cac cag gag att tta aag gac aag aag ctc atc aag gcc    3064
Ser Glu Asn His Gln Glu Ile Leu Lys Asp Lys Lys Leu Ile Lys Ala
            860                 865                 870 ttc ttt gag gtg cta gcc cac ccc cag aac tac ttc aag tac aca gag    3112
Phe Phe Glu Val Leu Ala His Pro Gln Asn Tyr Phe Lys Tyr Thr Glu
        875                 880                 885 aaa cac aag gag atg ctg cca aaa tcc ttc atc aag ctg ctc cgc tcc    3160
Lys His Lys Glu Met Leu Pro Lys Ser Phe Ile Lys Leu Leu Arg Ser
    890                 895                 900 aaa gtt tcc agc ttc ctg agg ccc tac aaa tag                         3193
Lys Val Ser Ser Phe Leu Arg Pro Tyr Lys
905                 910

<210> SEQ ID NO 6
<211> LENGTH: 914
<212> TYPE: PRT
<213> ORGANISM: Homo sapiens

<400> SEQUENCE: 6

Met Gly Ser Gly Arg Val Pro Gly Leu Cys Leu Leu Val Leu Leu Val
1               5                   10                  15

His Ala Arg Ala Ala Gln Tyr Ser Lys Ala Ala Gln Asp Val Asp Glu
            20                  25                  30

Cys Val Glu Gly Thr Asp Asn Cys His Ile Asp Ala Ile Cys Gln Asn
        35                  40                  45

Thr Pro Arg Ser Tyr Lys Cys Ile Cys Lys Ser Gly Tyr Thr Gly Asp
    50                  55                  60

Gly Lys His Cys Lys Asp Val Asp Glu Cys Glu Arg Glu Asp Asn Ala
65                  70                  75                  80

Gly Cys Val His Asp Cys Val Asn Ile Pro Gly Asn Tyr Arg Cys Thr
                85                  90                  95

Cys Tyr Asp Gly Phe His Leu Ala His Asp Gly His Asn Cys Leu Asp
            100                 105                 110

Val Asp Glu Cys Ala Glu Gly Asn Gly Gly Cys Gln Gln Ser Cys Val
        115                 120                 125

Asn Met Met Gly Ser Tyr Glu Cys His Cys Arg Glu Gly Phe Phe Leu
    130                 135                 140

Ser Asp Asn Gln His Thr Cys Ile Gln Arg Pro Glu Glu Gly Met Asn
145                 150                 155                 160

Cys Met Asn Lys Asn His Gly Cys Ala His Ile Cys Arg Glu Thr Pro
                165                 170                 175

Lys Gly Gly Ile Ala Cys Glu Cys Arg Pro Gly Phe Glu Leu Thr Lys
            180                 185                 190

Asn Gln Arg Asp Cys Lys Cys Glu Ile Ile Gly Met Ala Val Thr Cys
        195                 200                 205

Asn Tyr Gly Asn Gly Gly Cys Gln His Thr Cys Asp Asp Thr Glu Gln
    210                 215                 220

Gly Pro Arg Cys Gly Cys His Ile Lys Phe Val Leu His Thr Asp Gly
225                 230                 235                 240
```

-continued

```
Lys Thr Cys Ile Glu Thr Cys Ala Val Asn Asn Gly Cys Asp Ser
                245                 250                 255

Lys Cys His Asp Ala Ala Thr Gly Val His Cys Thr Cys Pro Val Gly
            260                 265                 270

Phe Met Leu Gln Pro Asp Arg Lys Thr Cys Lys Asp Ile Asp Glu Cys
        275                 280                 285

Arg Leu Asn Asn Gly Gly Cys Asp His Ile Cys Arg Asn Thr Val Gly
    290                 295                 300

Ser Phe Glu Cys Ser Cys Lys Lys Gly Tyr Lys Leu Leu Ile Asn Glu
305                 310                 315                 320

Arg Asn Cys Gln Asp Ile Asp Glu Cys Ser Phe Asp Arg Thr Cys Asp
                325                 330                 335

His Ile Cys Val Asn Thr Pro Gly Ser Phe Gln Cys Leu Cys His Arg
            340                 345                 350

Gly Tyr Leu Leu Tyr Gly Ile Thr His Cys Gly Asp Val Asp Glu Cys
        355                 360                 365

Ser Ile Asn Arg Gly Gly Cys Arg Phe Gly Cys Ile Asn Thr Pro Gly
    370                 375                 380

Ser Tyr Gln Cys Thr Cys Pro Ala Gly Gln Gly Arg Leu His Trp Asn
385                 390                 395                 400

Gly Lys Asp Cys Thr Glu Pro Leu Lys Cys Gln Gly Ser Pro Gly Ala
                405                 410                 415

Ser Lys Ala Met Leu Ser Cys Asn Arg Ser Gly Lys Lys Asp Thr Cys
            420                 425                 430

Ala Leu Thr Cys Pro Ser Arg Ala Arg Phe Leu Pro Glu Ser Glu Asn
        435                 440                 445

Gly Phe Thr Val Ser Cys Gly Thr Pro Ser Pro Arg Ala Ala Pro Ala
    450                 455                 460

Arg Ala Gly His Asn Gly Asn Ser Thr Asn Ser Asn His Cys His Gly
465                 470                 475                 480

Gly Ala Pro Cys Ser Glu Cys Gln Val Thr Phe Ile His Leu Lys Cys
                485                 490                 495

Asp Ser Ser Arg Lys Gly Lys Gly Arg Arg Ala Arg Thr Pro Pro Gly
            500                 505                 510

Lys Glu Val Thr Arg Leu Thr Leu Glu Leu Glu Ala Glu Gln Leu Phe
        515                 520                 525

Leu Leu Pro Asp Thr His Gly His Pro Pro Ala Ser Cys Gly Leu
    530                 535                 540

Pro Cys Leu Arg Gln Arg Met Glu Arg Arg Leu Lys Gly Ser Leu Lys
545                 550                 555                 560

Met Leu Arg Lys Ser Ile Asn Gln Asp Arg Phe Leu Leu Arg Leu Ala
                565                 570                 575

Gly Leu Asp Tyr Glu Leu Ala His Lys Pro Gly Leu Val Ala Gly Glu
            580                 585                 590

Arg Ser Glu Thr Asn Asp His Cys Thr Pro Gly His Asn Asn Ala Thr
        595                 600                 605

Thr Asn Ser Gly Gln Cys Pro Pro Gly Gln His Ser Val Asp Gly Phe
    610                 615                 620

Lys Pro Cys Gln Pro Cys Pro Arg Gly Thr Tyr Gln Pro Glu Ala Gly
625                 630                 635                 640

Arg Thr Leu Cys Phe Pro Cys Gly Gly Gly Leu Thr Thr Lys His Glu
                645                 650                 655
```

-continued

Gly Ala Ile Ser Phe Gln Asp Cys Asp Thr Lys Val Gln Cys Ser Pro
              660                 665                 670

Gly His Tyr Tyr Asn Thr Ser Ile His Arg Cys Ile Arg Cys Ala Met
         675                 680                 685

Gly Ser Tyr Gln Pro Asp Phe Arg Gln Asn Phe Cys Ser Arg Cys Pro
     690                 695                 700

Gly Asn Thr Ser Thr Asp Phe Asp Gly Ser Thr Ser Val Ala Gln Cys
705                 710                 715                 720

Lys Asn Arg Gln Cys Gly Gly Glu Leu Gly Glu Phe Thr Gly Tyr Ile
                725                 730                 735

Glu Ser Pro Asn Tyr Pro Gly Asn Tyr Pro Ala Gly Val Glu Cys Ile
             740                 745                 750

Trp Asn Ile Asn Pro Pro Lys Arg Lys Ile Leu Ile Val Val Pro
         755                 760                 765

Glu Ile Phe Leu Pro Ser Glu Asp Cys Gly Asp Val Leu Val Met
     770                 775                 780

Arg Lys Asn Ser Ser Pro Ser Ser Ile Thr Thr Tyr Glu Thr Cys Gln
785                 790                 795                 800

Thr Tyr Glu Arg Pro Ile Ala Phe Thr Ala Arg Ser Arg Lys Leu Trp
                805                 810                 815

Ile Asn Phe Lys Thr Ser Glu Ala Asn Ser Ala Arg Gly Phe Gln Ile
             820                 825                 830

Pro Tyr Val Thr Tyr Asp Glu Asp Tyr Glu Gln Leu Val Glu Asp Ile
         835                 840                 845

Val Arg Asp Gly Arg Leu Tyr Ala Ser Glu Asn His Gln Glu Ile Leu
     850                 855                 860

Lys Asp Lys Lys Leu Ile Lys Ala Phe Phe Glu Val Leu Ala His Pro
865                 870                 875                 880

Gln Asn Tyr Phe Lys Tyr Thr Glu Lys His Lys Glu Met Leu Pro Lys
                885                 890                 895

Ser Phe Ile Lys Leu Leu Arg Ser Lys Val Ser Ser Phe Leu Arg Pro
             900                 905                 910

Tyr Lys

<210> SEQ ID NO 7
<211> LENGTH: 3947
<212> TYPE: DNA
<213> ORGANISM: Homo sapiens
<220> FEATURE:
<221> NAME/KEY: CDS
<222> LOCATION: (443)...(3421)

<400> SEQUENCE: 7
agcagaaggg cgtgtttctg gcgctgcgtt tccctcccc tttctcaggt ccttcgctcg      60
ggctctgcgc gctctccggc tgcagctctc tcccggcgaa gctgggaatt gggtgggatt    120
acacggagca gccccgccgc cgccgctggc agaggccggc ttggagaggg cggggttcc     180 cctccgtcag tcgcccctgg cgcccctcgc cttgtcgcac tctccgcctc gctctccccg   240
acgtccggcc aggaggagcc ggtagcatcg ggagcctcgc gccgagggcg ccgcggtccg   300
cgccccgcga ctgcagcccc cggcctggcc cggcgggggc gcccctccc ctccccctcc    360 tgcgagctgg gatccggccg gcttccgccc tccctggccc gcgagaccgg cccggcggc    420 tgggccgcca gtagctccag cc atg ggc tcg ggg cgc gta ccc ggg ctc tgc    472
                        Met Gly Ser Gly Arg Val Pro Gly Leu Cys
                        1               5                   10

```
ctg ctt gtc ctg ctg gtc cac gcc cgc gcc gcc cag tac agc aaa gcc    520
Leu Leu Val Leu Leu Val His Ala Arg Ala Ala Gln Tyr Ser Lys Ala
             15                  20                  25 gcg caa gat gtg gat gag tgt gtg gag ggg act gac aac tgc cac atc    568
Ala Gln Asp Val Asp Glu Cys Val Glu Gly Thr Asp Asn Cys His Ile
             30                  35                  40 gat gct atc tgc cag aac acc ccg agg tca tac aag tgc atc tgc aag    616
Asp Ala Ile Cys Gln Asn Thr Pro Arg Ser Tyr Lys Cys Ile Cys Lys
             45                  50                  55 tct ggc tac aca ggg gac ggc aaa cac tgc aaa gac gtg gat gag tgc    664
Ser Gly Tyr Thr Gly Asp Gly Lys His Cys Lys Asp Val Asp Glu Cys
         60                  65                  70 gag cga gag gat aat gca ggt tgt gtg cat gac tgt gtc aac atc cct    712
Glu Arg Glu Asp Asn Ala Gly Cys Val His Asp Cys Val Asn Ile Pro
 75                  80                  85                  90 ggc aat tac cgg tgt acc tgc tat gat gga ttc cac ctg gca cat gac    760
Gly Asn Tyr Arg Cys Thr Cys Tyr Asp Gly Phe His Leu Ala His Asp
                 95                 100                 105 gga cac aac tgt ctg gat gtg gac gag tgt gcc gag ggc aac ggc ggc    808
Gly His Asn Cys Leu Asp Val Asp Glu Cys Ala Glu Gly Asn Gly Gly
                110                 115                 120 tgt cag cag agc tgt gtc aac atg atg ggc agc tat gag tgc cac tgc    856
Cys Gln Gln Ser Cys Val Asn Met Met Gly Ser Tyr Glu Cys His Cys
             125                 130                 135 cgg gaa ggc ttc ttc ctc agc gac aac cag cat acc tgt atc cag cgg    904
Arg Glu Gly Phe Phe Leu Ser Asp Asn Gln His Thr Cys Ile Gln Arg
         140                 145                 150 cca gaa gaa gga atg aat tgc atg aac aag aac cac ggc tgt gcc cac    952
Pro Glu Glu Gly Met Asn Cys Met Asn Lys Asn His Gly Cys Ala His
155                 160                 165                 170 att tgc cgg gag aca ccc aag ggg ggt att gcc tgt gaa tgc cgt cct   1000
Ile Cys Arg Glu Thr Pro Lys Gly Gly Ile Ala Cys Glu Cys Arg Pro
                175                 180                 185 ggc ttt gag ctt acc aag aac caa cgg gac tgt aaa ttg aca tgc aac   1048
Gly Phe Glu Leu Thr Lys Asn Gln Arg Asp Cys Lys Leu Thr Cys Asn
                190                 195                 200 tat ggt aac ggc ggc tgc cag cac acg tgt gat gac aca gag cag ggt   1096
Tyr Gly Asn Gly Gly Cys Gln His Thr Cys Asp Asp Thr Glu Gln Gly
             205                 210                 215 ccc cgg tgc ggc tgc cat atc aag ttt gtg ctc cat acc gac ggg aag   1144
Pro Arg Cys Gly Cys His Ile Lys Phe Val Leu His Thr Asp Gly Lys
         220                 225                 230 aca tgc atc gag acc tgt gct gtc aac aac ggg ggc tgt gac agt aag   1192
Thr Cys Ile Glu Thr Cys Ala Val Asn Asn Gly Gly Cys Asp Ser Lys
235                 240                 245                 250 tgc cat gat gca gcg act ggt gtc cac tgc acc tgc cct gtg ggc ttc   1240
Cys His Asp Ala Ala Thr Gly Val His Cys Thr Cys Pro Val Gly Phe
                255                 260                 265 atg ctg cag cca gac agg aag acg tgc aaa gat ata gat gag tgc cgc   1288
Met Leu Gln Pro Asp Arg Lys Thr Cys Lys Asp Ile Asp Glu Cys Arg
                270                 275                 280 tta aac aac ggg ggc tgt gac cat att tgc cgc aac aca gtg ggc agc   1336
Leu Asn Asn Gly Gly Cys Asp His Ile Cys Arg Asn Thr Val Gly Ser
             285                 290                 295 ttc gaa tgc agt tgc aag aaa ggc tat aag ctt ctc atc aat gag agg   1384
Phe Glu Cys Ser Cys Lys Lys Gly Tyr Lys Leu Leu Ile Asn Glu Arg
         300                 305                 310 aac tgc cag gat ata gac gag tgt tcc ttt gat cga acc tgt gac cac   1432
Asn Cys Gln Asp Ile Asp Glu Cys Ser Phe Asp Arg Thr Cys Asp His
315                 320                 325                 330
```

```
ata tgt gtc aac aca cca gga agc ttc cag tgt ctc tgc cat cgt ggc      1480
Ile Cys Val Asn Thr Pro Gly Ser Phe Gln Cys Leu Cys His Arg Gly
            335                 340                 345 tac ctg ttg tat ggt atc acc cac tgt ggg gat gtg gat gaa tgc agc      1528
Tyr Leu Leu Tyr Gly Ile Thr His Cys Gly Asp Val Asp Glu Cys Ser
        350                 355                 360 atc aac cgg gga ggt tgc cgc ttt ggc tgc atc aac act cct ggc agc      1576
Ile Asn Arg Gly Gly Cys Arg Phe Gly Cys Ile Asn Thr Pro Gly Ser
            365                 370                 375 tac cag tgt acc tgc cca gca ggc cag ggt cgg ctg cac tgg aat ggc      1624
Tyr Gln Cys Thr Cys Pro Ala Gly Gln Gly Arg Leu His Trp Asn Gly
        380                 385                 390 aaa gat tgc aca gag cca ctg aag tgt cag ggc agt cct ggg gcc tcg      1672
Lys Asp Cys Thr Glu Pro Leu Lys Cys Gln Gly Ser Pro Gly Ala Ser
395                 400                 405                 410 aaa gcc atg ctc agc tgc aac cgg tct ggc aag aag gac acc tgt gcc      1720
Lys Ala Met Leu Ser Cys Asn Arg Ser Gly Lys Lys Asp Thr Cys Ala
            415                 420                 425 ctg acc tgt ccc tcc agg gcc cga ttt ttg cca gag tct gag aat ggc      1768
Leu Thr Cys Pro Ser Arg Ala Arg Phe Leu Pro Glu Ser Glu Asn Gly
        430                 435                 440 ttc acg gtg agc tgt ggg acc ccc agc ccc agg gct gct cca gcc cga      1816
Phe Thr Val Ser Cys Gly Thr Pro Ser Pro Arg Ala Ala Pro Ala Arg
            445                 450                 455 gct ggc cac aat ggg aac agc acc aac tcc aac cac tgc cat gag gct      1864
Ala Gly His Asn Gly Asn Ser Thr Asn Ser Asn His Cys His Glu Ala
        460                 465                 470 gca gtg ctg tcc att aaa caa cgg gcc tcc ttc aag atc aag gat gcc      1912
Ala Val Leu Ser Ile Lys Gln Arg Ala Ser Phe Lys Ile Lys Asp Ala
475                 480                 485                 490 aaa tgc cgt ttg cac ctg cga aac aaa ggc aaa aca gag gag gct ggc      1960
Lys Cys Arg Leu His Leu Arg Asn Lys Gly Lys Thr Glu Glu Ala Gly
            495                 500                 505 aga atc aca ggg cca ggt ggt gcc ccc tgc tct gaa tgc cag gtc acc      2008
Arg Ile Thr Gly Pro Gly Gly Ala Pro Cys Ser Glu Cys Gln Val Thr
        510                 515                 520 ttc atc cac ctt aag tgt gac tcc tct cgg aag ggc aag ggc cga cgg      2056
Phe Ile His Leu Lys Cys Asp Ser Ser Arg Lys Gly Lys Gly Arg Arg
            525                 530                 535 gcc cgg acc cct cca ggc aaa gag gtc aca agg ctc acc ctg gaa ctg      2104
Ala Arg Thr Pro Pro Gly Lys Glu Val Thr Arg Leu Thr Leu Glu Leu
        540                 545                 550 gag gca gag gtc aga gcc gaa gaa acc aca gcc agc tgt ggg ctg ccc      2152
Glu Ala Glu Val Arg Ala Glu Glu Thr Thr Ala Ser Cys Gly Leu Pro
555                 560                 565                 570 tgc ctc cga cag cga atg gaa cgg cgg ctg aaa gga tcc ctg aag atg      2200
Cys Leu Arg Gln Arg Met Glu Arg Arg Leu Lys Gly Ser Leu Lys Met
            575                 580                 585 ctc aga aag tcc atc aac cag gac cgc ttc ctg ctc cgc ctg gca ggc      2248
Leu Arg Lys Ser Ile Asn Gln Asp Arg Phe Leu Leu Arg Leu Ala Gly
        590                 595                 600 ctt gat tat gag ctg gcc cac aag ccg ggc ctg gta gcc ggg gag cga      2296
Leu Asp Tyr Glu Leu Ala His Lys Pro Gly Leu Val Ala Gly Glu Arg
            605                 610                 615 gca gag ccg atg gag tcc tgt agg ccc ggg cag cac cgt gct ggg acc      2344
Ala Glu Pro Met Glu Ser Cys Arg Pro Gly Gln His Arg Ala Gly Thr
        620                 625                 630 aag tgt gtc agc tgc ccg cag gga acg tat tac cac tgc cag acg gag      2392
Lys Cys Val Ser Cys Pro Gln Gly Thr Tyr Tyr His Cys Gln Thr Glu
```

-continued

```
              635                 640                 645                 650 cag tgt gtg cca tgc cca gcg ggc acc ttc cag gag aga gaa ggg cag    2440
Gln Cys Val Pro Cys Pro Ala Gly Thr Phe Gln Glu Arg Glu Gly Gln
                655                 660                 665 ctc tcc tgc gac ctt tgc cct ggg agt gat gcc cac ggg cct ctt gga    2488
Leu Ser Cys Asp Leu Cys Pro Gly Ser Asp Ala His Gly Pro Leu Gly
            670                 675                 680 gcc acc aac gtc acc acg tgt gca ggt cag tgc cca cct ggc caa cac    2536
Ala Thr Asn Val Thr Thr Cys Ala Gly Gln Cys Pro Pro Gly Gln His
        685                 690                 695 tct gta gat ggg ttc aag ccc tgt cag cca tgc cca cgt ggc acc tac    2584
Ser Val Asp Gly Phe Lys Pro Cys Gln Pro Cys Pro Arg Gly Thr Tyr
    700                 705                 710 caa cct gaa gca gga cgg acc cta tgc ttc cct tgt ggt ggg ggc ctc    2632
Gln Pro Glu Ala Gly Arg Thr Leu Cys Phe Pro Cys Gly Gly Gly Leu
715                 720                 725                 730 acc acc aag cat gaa ggg gcc att tcc ttc caa gac tgt gac acc aaa    2680
Thr Thr Lys His Glu Gly Ala Ile Ser Phe Gln Asp Cys Asp Thr Lys
                735                 740                 745 gtc cag tgc tcc cca ggg cac tac tac aac acc agc atc cac cgc tgt    2728
Val Gln Cys Ser Pro Gly His Tyr Tyr Asn Thr Ser Ile His Arg Cys
            750                 755                 760 att cgc tgt gcc atg ggc tcc tat cag ccc gac ttc gtc cag aac ttc    2776
Ile Arg Cys Ala Met Gly Ser Tyr Gln Pro Asp Phe Arg Gln Asn Phe
        765                 770                 775 tgc agc cgc tgt cca gga aac aca agc aca gac ttt gat ggc tct acc    2824
Cys Ser Arg Cys Pro Gly Asn Thr Ser Thr Asp Phe Asp Gly Ser Thr
    780                 785                 790 agt gtg gcc caa tgc aag aat cgt cag tgt ggt ggg gag ctg ggt gag    2872
Ser Val Ala Gln Cys Lys Asn Arg Gln Cys Gly Gly Glu Leu Gly Glu
795                 800                 805                 810 ttc act ggc tat att gag tcc ccc aac tac ccg ggc aac tac cca gct    2920
Phe Thr Gly Tyr Ile Glu Ser Pro Asn Tyr Pro Gly Asn Tyr Pro Ala
                815                 820                 825 ggt gtg gag tgc atc tgg aac atc aac ccc cca ccc aag cgc aag atc    2968
Gly Val Glu Cys Ile Trp Asn Ile Asn Pro Pro Pro Lys Arg Lys Ile
            830                 835                 840 ctt atc gtg gta cca gag atc ttc ctg cca tct gag gat gag tgt ggg    3016
Leu Ile Val Val Pro Glu Ile Phe Leu Pro Ser Glu Asp Glu Cys Gly
        845                 850                 855 gac gtc ctc gtc atg aga aag aac tca tcc cca tcc tcc att acc act    3064
Asp Val Leu Val Met Arg Lys Asn Ser Ser Pro Ser Ser Ile Thr Thr
    860                 865                 870 tat gag acc tgc cag acc tac gag cgt ccc att gcc ttc act gcc cgt    3112
Tyr Glu Thr Cys Gln Thr Tyr Glu Arg Pro Ile Ala Phe Thr Ala Arg
875                 880                 885                 890 tcc agg aag ctc tgg atc aac ttc aag aca agc gag gcc aac agc gcc    3160
Ser Arg Lys Leu Trp Ile Asn Phe Lys Thr Ser Glu Ala Asn Ser Ala
                895                 900                 905 cgt ggc ttc cag att ccc tat gtt acc tat gat gag gac tat gag cag    3208
Arg Gly Phe Gln Ile Pro Tyr Val Thr Tyr Asp Glu Asp Tyr Glu Gln
            910                 915                 920 ctg gta gaa gac att gtg cga gat ggc cgg ctc tat gcc tct gaa aac    3256
Leu Val Glu Asp Ile Val Arg Asp Gly Arg Leu Tyr Ala Ser Glu Asn
        925                 930                 935 cac cag gag att tta aag gac aag aag ctc atc aag gcc ttc ttt gag    3304
His Gln Glu Ile Leu Lys Asp Lys Lys Leu Ile Lys Ala Phe Phe Glu
    940                 945                 950 gtg cta gcc cac ccc cag aac tac ttc aag tac aca gag aaa cac aag    3352
```

```
Val Leu Ala His Pro Gln Asn Tyr Phe Lys Tyr Thr Glu Lys His Lys
955                 960                 965                 970 gag atg ctg cca aaa tcc ttc atc aag ctg ctc cgc tcc aaa gtt tcc    3400
Glu Met Leu Pro Lys Ser Phe Ile Lys Leu Leu Arg Ser Lys Val Ser
                975                 980                 985 agc ttc ctg agg ccc tac aaa tagtaaccct aggctcagag acccaatttt       3451
Ser Phe Leu Arg Pro Tyr Lys
                990 ttaagccccc agactcctta gccctcagag ccggcagccc cctaccctca gacaaggaac  3511 tctctcctct cttttggag ggaaaaaaaa aatatcacta cacaaaccag gcactctccc   3571 tttctgtctt tctagtttcc tttccttgtc tctctctgcc tgcctctcta ctgttccccc  3631 ttttctaaca cactacctag aaaagccatt cagtactggc tctagtcccc atgagatgta  3691 aagaaacagt acagccccct ccactgccca ttttaccagc tcacattccc gaccccatca  3751 gcttggaagg gtgctagagg cccatcaagg aagtgggtct ggtgggaaac ggggagggga  3811 aagaagggct tctgccatta tagggttgtg ccttgctagt caggggccaa aatgtcccct  3871 ggctctgctc cctagggtga ttctaacagc ccagggtcct gccaagaag cctttgattt   3931 acaggcttaa tgccag                                                  3947
```

<210> SEQ ID NO 8
<211> LENGTH: 993
<212> TYPE: PRT
<213> ORGANISM: Homo sapiens

<400> SEQUENCE: 8

```
Met Gly Ser Gly Arg Val Pro Gly Leu Cys Leu Leu Val Leu Leu Val
 1               5                  10                  15

His Ala Arg Ala Ala Gln Tyr Ser Lys Ala Ala Gln Asp Val Asp Glu
                20                  25                  30

Cys Val Glu Gly Thr Asp Asn Cys His Ile Asp Ala Ile Cys Gln Asn
            35                  40                  45

Thr Pro Arg Ser Tyr Lys Cys Ile Cys Lys Ser Gly Tyr Thr Gly Asp
        50                  55                  60

Gly Lys His Cys Lys Asp Val Asp Glu Cys Glu Arg Glu Asp Asn Ala
65                  70                  75                  80

Gly Cys Val His Asp Cys Val Asn Ile Pro Gly Asn Tyr Arg Cys Thr
                85                  90                  95

Cys Tyr Asp Gly Phe His Leu Ala His Asp Gly His Asn Cys Leu Asp
            100                 105                 110

Val Asp Glu Cys Ala Glu Gly Asn Gly Gly Cys Gln Gln Ser Cys Val
        115                 120                 125

Asn Met Met Gly Ser Tyr Glu Cys His Cys Arg Glu Gly Phe Phe Leu
130                 135                 140

Ser Asp Asn Gln His Thr Cys Ile Gln Arg Pro Glu Glu Gly Met Asn
                145                 150                 155                 160

Cys Met Asn Lys Asn His Gly Cys Ala His Ile Cys Arg Glu Thr Pro
                165                 170                 175

Lys Gly Gly Ile Ala Cys Glu Cys Arg Pro Gly Phe Glu Leu Thr Lys
            180                 185                 190

Asn Gln Arg Asp Cys Lys Leu Thr Cys Asn Tyr Gly Asn Gly Gly Cys
        195                 200                 205

Gln His Thr Cys Asp Asp Thr Glu Gln Gly Pro Arg Cys Gly Cys His
    210                 215                 220
```

```
Ile Lys Phe Val Leu His Thr Asp Gly Lys Thr Cys Ile Glu Thr Cys
225                 230                 235                 240

Ala Val Asn Asn Gly Gly Cys Asp Ser Lys Cys His Asp Ala Ala Thr
            245                 250                 255

Gly Val His Cys Thr Cys Pro Val Gly Phe Met Leu Gln Pro Asp Arg
        260                 265                 270

Lys Thr Cys Lys Asp Ile Asp Glu Cys Arg Leu Asn Asn Gly Gly Cys
    275                 280                 285

Asp His Ile Cys Arg Asn Thr Val Gly Ser Phe Glu Cys Ser Cys Lys
290                 295                 300

Lys Gly Tyr Lys Leu Leu Ile Asn Glu Arg Asn Cys Gln Asp Ile Asp
305                 310                 315                 320

Glu Cys Ser Phe Asp Arg Thr Cys Asp His Ile Cys Val Asn Thr Pro
                325                 330                 335

Gly Ser Phe Gln Cys Leu Cys His Arg Gly Tyr Leu Leu Tyr Gly Ile
            340                 345                 350

Thr His Cys Gly Asp Val Asp Glu Cys Ser Ile Asn Arg Gly Gly Cys
        355                 360                 365

Arg Phe Gly Cys Ile Asn Thr Pro Gly Ser Tyr Gln Cys Thr Cys Pro
370                 375                 380

Ala Gly Gln Gly Arg Leu His Trp Asn Gly Lys Asp Cys Thr Glu Pro
385                 390                 395                 400

Leu Lys Cys Gln Gly Ser Pro Gly Ala Ser Lys Ala Met Leu Ser Cys
                405                 410                 415

Asn Arg Ser Gly Lys Lys Asp Thr Cys Ala Leu Thr Cys Pro Ser Arg
            420                 425                 430

Ala Arg Phe Leu Pro Glu Ser Glu Asn Gly Phe Thr Val Ser Cys Gly
        435                 440                 445

Thr Pro Ser Pro Arg Ala Ala Pro Ala Arg Ala Gly His Asn Gly Asn
450                 455                 460

Ser Thr Asn Ser Asn His Cys His Glu Ala Ala Val Leu Ser Ile Lys
465                 470                 475                 480

Gln Arg Ala Ser Phe Lys Ile Lys Asp Ala Lys Cys Arg Leu His Leu
                485                 490                 495

Arg Asn Lys Gly Lys Thr Glu Glu Ala Gly Arg Ile Thr Gly Pro Gly
            500                 505                 510

Gly Ala Pro Cys Ser Glu Cys Gln Val Thr Phe Ile His Leu Lys Cys
        515                 520                 525

Asp Ser Ser Arg Lys Gly Lys Gly Arg Arg Ala Arg Thr Pro Pro Gly
530                 535                 540

Lys Glu Val Thr Arg Leu Thr Leu Glu Leu Glu Ala Glu Val Arg Ala
545                 550                 555                 560

Glu Glu Thr Thr Ala Ser Cys Gly Leu Pro Cys Leu Arg Gln Arg Met
                565                 570                 575

Glu Arg Arg Leu Lys Gly Ser Leu Lys Met Leu Arg Lys Ser Ile Asn
            580                 585                 590

Gln Asp Arg Phe Leu Leu Arg Leu Ala Gly Leu Asp Tyr Glu Leu Ala
        595                 600                 605

His Lys Pro Gly Leu Val Ala Gly Glu Arg Ala Glu Pro Met Glu Ser
610                 615                 620

Cys Arg Pro Gly Gln His Arg Ala Gly Thr Lys Cys Val Ser Cys Pro
625                 630                 635                 640

Gln Gly Thr Tyr Tyr His Cys Gln Thr Glu Gln Cys Val Pro Cys Pro
```

```
                     645                 650                 655
Ala Gly Thr Phe Gln Glu Arg Glu Gly Gln Leu Ser Cys Asp Leu Cys
            660                 665                 670

Pro Gly Ser Asp Ala His Gly Pro Leu Gly Ala Thr Asn Val Thr Thr
            675                 680                 685

Cys Ala Gly Gln Cys Pro Pro Gly Gln His Ser Val Asp Gly Phe Lys
            690                 695                 700

Pro Cys Gln Pro Cys Pro Arg Gly Thr Tyr Gln Pro Glu Ala Gly Arg
705                 710                 715                 720

Thr Leu Cys Phe Pro Cys Gly Gly Leu Thr Thr Lys His Glu Gly
                725                 730                 735

Ala Ile Ser Phe Gln Asp Cys Asp Thr Lys Val Gln Cys Ser Pro Gly
            740                 745                 750

His Tyr Tyr Asn Thr Ser Ile His Arg Cys Ile Arg Cys Ala Met Gly
            755                 760                 765

Ser Tyr Gln Pro Asp Phe Arg Gln Asn Phe Cys Ser Arg Cys Pro Gly
            770                 775                 780

Asn Thr Ser Thr Asp Phe Asp Gly Ser Thr Ser Val Ala Gln Cys Lys
785                 790                 795                 800

Asn Arg Gln Cys Gly Gly Glu Leu Gly Glu Phe Thr Gly Tyr Ile Glu
                805                 810                 815

Ser Pro Asn Tyr Pro Gly Asn Tyr Pro Ala Gly Val Glu Cys Ile Trp
            820                 825                 830

Asn Ile Asn Pro Pro Lys Arg Lys Ile Leu Ile Val Val Pro Glu
            835                 840                 845

Ile Phe Leu Pro Ser Glu Asp Glu Cys Gly Asp Val Leu Val Met Arg
850                 855                 860

Lys Asn Ser Ser Pro Ser Ser Ile Thr Thr Tyr Glu Thr Cys Gln Thr
865                 870                 875                 880

Tyr Glu Arg Pro Ile Ala Phe Thr Ala Arg Ser Arg Lys Leu Trp Ile
                885                 890                 895

Asn Phe Lys Thr Ser Glu Ala Asn Ser Ala Arg Gly Phe Gln Ile Pro
            900                 905                 910

Tyr Val Thr Tyr Asp Glu Asp Tyr Glu Gln Leu Val Glu Asp Ile Val
            915                 920                 925

Arg Asp Gly Arg Leu Tyr Ala Ser Glu Asn His Gln Glu Ile Leu Lys
            930                 935                 940

Asp Lys Lys Leu Ile Lys Ala Phe Phe Glu Val Leu Ala His Pro Gln
945                 950                 955                 960

Asn Tyr Phe Lys Tyr Thr Glu Lys His Lys Glu Met Leu Pro Lys Ser
                965                 970                 975

Phe Ile Lys Leu Leu Arg Ser Lys Val Ser Ser Phe Leu Arg Pro Tyr
            980                 985                 990

Lys

<210> SEQ ID NO 9
<211> LENGTH: 45
<212> TYPE: PRT
<213> ORGANISM: Artificial Sequence
<220> FEATURE:
<223> OTHER INFORMATION: consensus

<400> SEQUENCE: 9

Cys Ala Pro Asn Asn Pro Cys Ser Asn Gly Gly Thr Cys Val Asn Thr
1               5                   10                  15
```

```
Pro Gly Gly Ser Ser Asp Asn Phe Gly Gly Tyr Thr Cys Glu Cys Pro
            20                  25                  30

Pro Gly Asp Tyr Tyr Leu Ser Tyr Thr Gly Lys Arg Cys
        35                  40                  45

<210> SEQ ID NO 10
<211> LENGTH: 116
<212> TYPE: PRT
<213> ORGANISM: Artificial Sequence
<220> FEATURE:
<223> OTHER INFORMATION: consensus

<400> SEQUENCE: 10

Cys Gly Gly Thr Leu Asp Leu Thr Glu Ser Ser Gly Ser Ile Ser Ser
 1               5                  10                  15

Pro Asn Tyr Pro Asn Arg Ser Asp Tyr Pro Pro Asn Lys Glu Cys Val
            20                  25                  30

Trp Arg Ile Arg Ala Pro Pro Gly Tyr Arg Val Val Glu Leu Thr Phe
        35                  40                  45

Gln Asp Phe Asp Leu Glu Asp His Asp Gly Ala Cys Arg Tyr Asp Tyr
    50                  55                  60

Val Glu Ile Arg Asp Gly Asp Pro Ser Ser Pro Leu Leu Gly Arg
65                  70                  75                  80

Phe Cys Gly Ser Gly Lys Pro Glu Asp Ile Arg Ser Thr Ser Asn Arg
                85                  90                  95

Met Leu Ile Lys Phe Val Ser Asp Ala Ser Val Ser Lys Arg Gly Phe
            100                 105                 110

Lys Ala Thr Tyr
        115

<210> SEQ ID NO 11
<211> LENGTH: 16
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 2,4,5,8-15
<223> OTHER INFORMATION: The Xaa at these positions can be any amino
      acid.
<220> FEATURE:
<221> NAME/KEY: VARIANT
<222> LOCATION: 6
<223> OTHER INFORMATION: The amino acid residue at position 6 can be
      Gly or Pro.
<220> FEATURE:
<221> NAME/KEY: VARIANT
<222> LOCATION: 7
<223> OTHER INFORMATION: The amino acid residue at position 7 can be
      Phe, Tyr, or Trp.
<220> FEATURE:
<221> NAME/KEY: VARIANT
<222> LOCATION: (8)...(15)
<223> OTHER INFORMATION: This region can have 4, 5, 6, 7, or 8 residues.

<400> SEQUENCE: 11

Cys Xaa Cys Xaa Xaa Xaa Xaa Xaa Xaa Xaa Xaa Xaa Xaa Xaa Xaa Cys
 1               5                  10                  15

<210> SEQ ID NO 12
<211> LENGTH: 37
<212> TYPE: PRT
<213> ORGANISM: Artificial Sequence
<220> FEATURE:
```

```
<223> OTHER INFORMATION: consensus
<220> FEATURE:
<221> NAME/KEY: VARIANT
<222> LOCATION: 1,3,4
<223> OTHER INFORMATION: The amino acid residue at position 1, 3, or 4
      can be Asp, Glu, Gln or Asn.
<220> FEATURE:
<221> NAME/KEY: VARIANT
<222> LOCATION: 2,6-19,21-27,29,31-34,36
<223> OTHER INFORMATION: The Xaa amino acid residue at these positions
      can be any amino acid.
<220> FEATURE:
<221> NAME/KEY: VARIANT
<222> LOCATION: 30
<223> OTHER INFORMATION: The amino acid residue at position 30 can be
      Asp or Asn.
<220> FEATURE:
<221> NAME/KEY: VARIANT
<222> LOCATION: 35
<223> OTHER INFORMATION: The amino acid residue at position 35 can be
      Phe or Tyr.
<220> FEATURE:
<221> NAME/KEY: VARIANT
<222> LOCATION: (6)...(19)
<223> OTHER INFORMATION: The number of residues in this region can be
      between three and fourteen.
<220> FEATURE:
<221> NAME/KEY: VARIANT
<222> LOCATION: (21)...(27)
<223> OTHER INFORMATION: The number of residues in this region can be
      between three and seven.

<400> SEQUENCE: 12

Xaa Xaa Xaa Xaa Cys Xaa Xaa Xaa Xaa Xaa Xaa Xaa Xaa Xaa Xaa
 1               5                  10                  15

Xaa Xaa Xaa Cys Xaa Xaa Xaa Xaa Xaa Xaa Xaa Cys Xaa Xaa Xaa Xaa
            20                  25                  30

Xaa Xaa Xaa Xaa Cys
            35

<210> SEQ ID NO 13
<211> LENGTH: 961
<212> TYPE: PRT
<213> ORGANISM: Mus musculus

<400> SEQUENCE: 13

Met Gly Ala Ala Ala Val Arg Trp His Leu Ser Leu Leu Ala Leu
 1               5                  10                  15

Gly Ala Arg Gly Gln Leu Val Gly Gly Ser Gly Leu Pro Gly Ala Val
            20                  25                  30

Asp Val Asp Glu Cys Ser Glu Gly Thr Asp Asp Cys His Ile Asp Ala
            35                  40                  45

Ile Cys Gln Asn Thr Pro Lys Ser Tyr Lys Cys Leu Cys Lys Pro Gly
 50                  55                  60

Tyr Lys Gly Glu Gly Arg Gln Cys Glu Asp Ile Asp Glu Cys Glu Asn
 65                  70                  75                  80

Asp Tyr Tyr Asn Gly Gly Cys Val His Asp Cys Ile Asn Ile Pro Gly
                 85                  90                  95

Asn Tyr Arg Cys Thr Cys Phe Asp Gly Phe Met Leu Ala His Asp Gly
                100                 105                 110

His Asn Cys Leu Asp Val Asp Glu Cys Gln Asp Asn Asn Gly Gly Cys
            115                 120                 125

Gln Gln Ile Cys Val Asn Ala Met Gly Ser Tyr Glu Cys Gln Cys His
         130                 135                 140

Ser Gly Phe Phe Leu Ser Asp Asn Gln His Thr Cys Ile His Arg Ser
```

-continued

```
            145                 150                 155                 160
Asn Glu Gly Met Asn Cys Met Asn Lys Asp His Gly Cys Ala His Ile
                165                 170                 175
Cys Arg Glu Thr Pro Lys Gly Val Ala Cys Asp Cys Arg Pro Gly
            180                 185                 190
Phe Asp Leu Ala Gln Asn Gln Lys Asp Cys Thr Leu Thr Cys Asn Tyr
                195                 200                 205
Gly Asn Gly Gly Cys Gln His Ser Cys Glu Asp Thr Asp Gly Pro
            210                 215                 220
Met Cys Gly Cys His Gln Lys Tyr Ala Leu His Ala Asp Gly Arg Thr
225                 230                 235                 240
Cys Ile Glu Thr Cys Ala Val Asn Asn Gly Gly Cys Asp Arg Thr Cys
                245                 250                 255
Lys Asp Thr Ala Thr Gly Val Arg Cys Ser Cys Pro Val Gly Phe Thr
            260                 265                 270
Leu Gln Pro Asp Gly Lys Thr Cys Lys Asp Ile Asn Glu Cys Leu Met
            275                 280                 285
Asn Asn Gly Gly Cys Asp His Phe Cys Arg Asn Thr Val Gly Ser Phe
            290                 295                 300
Glu Cys Gly Cys Gln Lys Gly His Lys Leu Leu Thr Asp Glu Arg Thr
305                 310                 315                 320
Cys Gln Asp Ile Asp Glu Cys Ser Phe Glu Arg Thr Cys Asp His Ile
                325                 330                 335
Cys Ile Asn Ser Pro Gly Ser Phe Gln Cys Leu Cys Arg Arg Gly Tyr
                340                 345                 350
Thr Leu Tyr Gly Thr Thr His Cys Gly Asp Val Asp Glu Cys Ser Met
                355                 360                 365
Asn Asn Gly Ser Cys Glu Gln Gly Cys Val Asn Thr Arg Gly Ser Tyr
            370                 375                 380
Glu Cys Val Cys Pro Pro Gly Arg Arg Leu His Trp Asn Gln Lys Asp
385                 390                 395                 400
Cys Val Glu Met Asn Gly Cys Leu Ser Arg Ser Lys Ala Ser Ala Gln
                405                 410                 415
Ala Gln Leu Ser Cys Gly Lys Val Gly Gly Val Glu Asn Cys Phe Leu
            420                 425                 430
Ser Cys Leu Gly His Ser Leu Phe Met Pro Asp Ser Glu Ser Ser Tyr
            435                 440                 445
Ile Leu Ser Cys Gly Val Pro Gly Leu Gln Gly Lys Thr Leu Pro Lys
            450                 455                 460
Arg Asn Gly Thr Ser Ser Thr Gly Pro Gly Cys Ser Asp Ala Pro
465                 470                 475                 480
Thr Thr Pro Ile Arg Gln Lys Ala Arg Phe Lys Ile Arg Asp Ala Lys
                485                 490                 495
Cys His Leu Gln Pro Arg Ser Gln Glu Arg Ala Lys Asp Thr Leu Arg
                500                 505                 510
His Pro Leu Leu Asp Asn Cys His Val Thr Phe Val Thr Leu Lys Cys
            515                 520                 525
Asp Ser Ser Lys Lys Arg Arg Arg Gly Arg Lys Ser Pro Ser Lys Glu
            530                 535                 540
Val Ser His Ile Thr Ala Glu Phe Glu Val Glu Met Lys Val Asp Glu
545                 550                 555                 560
Ala Ser Gly Thr Cys Glu Ala Asp Cys Met Arg Lys Arg Ala Glu Gln
                565                 570                 575
```

-continued

```
Ser Leu Gln Ala Ala Ile Lys Ile Leu Arg Lys Ser Thr Gly Arg Asn
            580                 585                 590
Gln Phe Tyr Val Gln Val Leu Gly Thr Glu Tyr Glu Val Ala Gln Arg
        595                 600                 605
Pro Ala Lys Ala Leu Glu Gly Thr Gly Thr Cys Gly Ile Gly Gln Ile
    610                 615                 620
Leu Gln Asp Gly Lys Cys Val Pro Cys Ala Pro Gly Thr Tyr Phe Ser
625                 630                 635                 640
Gly Asp Pro Gly Gln Cys Met Pro Cys Val Ser Gly Thr Tyr Gln Asp
                645                 650                 655
Met Glu Gly Gln Leu Ser Cys Thr Pro Cys Pro Ser Ser Glu Gly Leu
            660                 665                 670
Gly Leu Ala Gly Ala Arg Asn Val Ser Glu Cys Gly Gly Gln Cys Ser
        675                 680                 685
Pro Gly Tyr Phe Ser Ala Asp Gly Phe Lys Pro Cys Gln Ala Cys Pro
    690                 695                 700
Val Gly Thr Tyr Gln Pro Glu Pro Gly Arg Thr Gly Cys Phe Pro Cys
705                 710                 715                 720
Gly Gly Gly Leu Leu Thr Lys His Thr Gly Thr Ala Ser Phe Gln Asp
                725                 730                 735
Cys Glu Ala Lys Val His Cys Ser Pro Gly His His Tyr Asn Thr Thr
            740                 745                 750
Thr His Arg Cys Ile Arg Cys Pro Val Gly Thr Tyr Gln Pro Glu Phe
        755                 760                 765
Gly Gln Asn His Cys Ile Ser Cys Pro Gly Asn Thr Ser Thr Asp Phe
    770                 775                 780
Asp Gly Ser Thr Asn Val Thr His Cys Lys Asn Gln His Cys Gly Gly
785                 790                 795                 800
Glu Leu Gly Asp Tyr Thr Gly Tyr Ile Glu Ser Pro Asn Tyr Pro Gly
                805                 810                 815
Asp Tyr Pro Ala Asn Ala Glu Cys Val Trp His Ile Ala Pro Pro Pro
            820                 825                 830
Lys Arg Arg Ile Leu Ile Val Val Pro Glu Ile Phe Leu Pro Ile Glu
        835                 840                 845
Asp Glu Cys Gly Asp Val Leu Val Met Arg Lys Ser Ala Ser Pro Thr
    850                 855                 860
Ser Val Thr Thr Tyr Glu Thr Cys Gln Thr Tyr Glu Arg Pro Ile Ala
865                 870                 875                 880
Phe Thr Ser Arg Ser Arg Lys Leu Trp Ile Gln Phe Lys Ser Asn Glu
                885                 890                 895
Ala Asn Ser Gly Lys Gly Phe Gln Val Pro Tyr Val Thr Tyr Asp Gly
            900                 905                 910
Lys Ser Pro Pro Ser Cys His Ser Pro Leu Cys Ala Ser Gln Gly Leu
        915                 920                 925
Ala Trp Gly Leu Arg Asn Glu Leu His Ile Pro Ala Ser Asp Arg Ala
    930                 935                 940
Gln Thr Gln Arg Gln Lys Leu Gly Leu Gly Asn Ala Glu Thr Gln Gly
945                 950                 955                 960
Val
```

<210> SEQ ID NO 14
<211> LENGTH: 999
<212> TYPE: PRT

<213> ORGANISM: Homo sapiens

<400> SEQUENCE: 14

```
Met Gly Val Ala Gly Arg Asn Arg Pro Gly Ala Ala Trp Ala Val Leu
 1               5                  10                  15

Leu Leu Leu Leu Leu Leu Pro Pro Leu Leu Leu Ala Gly Ala Val
                20                  25                  30

Pro Pro Gly Arg Gly Arg Ala Ala Gly Pro Gln Glu Asp Val Asp Glu
             35                  40                  45

Cys Ala Gln Gly Leu Asp Asp Cys His Ala Asp Ala Leu Cys Gln Asn
 50                  55                  60

Thr Pro Thr Ser Tyr Lys Cys Ser Cys Lys Pro Gly Tyr Gln Gly Glu
 65                  70                  75                  80

Gly Arg Gln Cys Glu Asp Ile Asp Glu Cys Gly Asn Glu Leu Asn Gly
             85                  90                  95

Gly Cys Val His Asp Cys Leu Asn Ile Pro Gly Asn Tyr Arg Cys Thr
                100                 105                 110

Cys Phe Asp Gly Phe Met Leu Ala His Asp Gly His Asn Cys Leu Asp
         115                 120                 125

Val Asp Glu Cys Leu Glu Asn Asn Gly Gly Cys Gln His Thr Cys Val
130                 135                 140

Asn Val Met Gly Ser Tyr Glu Cys Cys Lys Glu Gly Phe Phe Leu
145                 150                 155                 160

Ser Asp Asn Gln His Thr Cys Ile His Arg Ser Glu Glu Gly Leu Ser
                165                 170                 175

Cys Met Asn Lys Asp His Gly Cys Ser His Ile Cys Lys Glu Ala Pro
            180                 185                 190

Arg Gly Ser Val Ala Cys Glu Cys Arg Pro Gly Phe Glu Leu Ala Lys
        195                 200                 205

Asn Gln Arg Asp Cys Ile Leu Thr Cys Asn His Gly Asn Gly Gly Cys
210                 215                 220

Gln His Ser Cys Asp Asp Thr Ala Asp Gly Pro Glu Cys Ser Cys His
225                 230                 235                 240

Pro Gln Tyr Lys Met His Thr Asp Gly Arg Ser Cys Leu Glu Arg Glu
                245                 250                 255

Asp Thr Val Leu Glu Val Thr Glu Ser Asn Thr Thr Ser Val Val Asp
            260                 265                 270

Gly Asp Lys Arg Val Lys Arg Arg Leu Leu Met Glu Thr Cys Ala Val
        275                 280                 285

Asn Asn Gly Gly Cys Asp Arg Thr Cys Lys Asp Thr Ser Thr Gly Val
290                 295                 300

His Cys Ser Cys Pro Val Gly Phe Thr Leu Gln Leu Asp Gly Lys Thr
305                 310                 315                 320

Cys Lys Asp Ile Asp Glu Cys Gln Thr Arg Asn Gly Gly Cys Asp His
                325                 330                 335

Phe Cys Lys Asn Ile Val Gly Ser Phe Asp Cys Gly Cys Lys Lys Gly
            340                 345                 350

Phe Lys Leu Leu Thr Asp Glu Lys Ser Cys Gln Asp Val Asp Glu Cys
        355                 360                 365

Ser Leu Asp Arg Thr Cys Asp His Ser Cys Ile Asn His Pro Gly Thr
370                 375                 380

Phe Ala Cys Ala Cys Asn Arg Gly Tyr Thr Leu Tyr Gly Phe Thr His
385                 390                 395                 400
```

-continued

```
Cys Gly Asp Thr Asn Glu Cys Ser Ile Asn Asn Gly Gly Cys Gln Gln
                405                 410                 415

Val Cys Val Asn Thr Val Gly Ser Tyr Glu Cys Gln Cys His Pro Gly
            420                 425                 430

Tyr Lys Leu His Trp Asn Lys Lys Asp Cys Val Glu Val Lys Gly Leu
        435                 440                 445

Leu Pro Thr Ser Val Ser Pro Arg Val Ser Leu His Cys Gly Lys Ser
450                 455                 460

Gly Gly Gly Asp Gly Cys Phe Leu Arg Cys His Ser Gly Ile His Leu
465                 470                 475                 480

Ser Ser Asp Val Thr Thr Ile Arg Thr Ser Val Thr Phe Lys Leu Asn
                485                 490                 495

Glu Gly Lys Cys Ser Leu Lys Asn Ala Glu Leu Phe Pro Glu Gly Leu
            500                 505                 510

Arg Pro Ala Leu Pro Glu Lys His Ser Ser Val Lys Glu Ser Phe Arg
        515                 520                 525

Tyr Val Asn Leu Thr Cys Ser Ser Gly Lys Gln Val Pro Gly Ala Pro
530                 535                 540

Gly Arg Pro Ser Thr Pro Lys Glu Met Phe Ile Thr Val Glu Phe Glu
545                 550                 555                 560

Leu Glu Thr Asn Gln Lys Glu Val Thr Ala Ser Cys Asp Leu Ser Cys
                565                 570                 575

Ile Val Lys Arg Thr Glu Lys Arg Leu Arg Lys Ala Ile Arg Thr Leu
            580                 585                 590

Arg Lys Ala Val His Arg Glu Gln Phe His Leu Gln Leu Ser Gly Met
        595                 600                 605

Asn Leu Asp Val Ala Lys Lys Pro Pro Arg Thr Ser Glu Arg Gln Ala
610                 615                 620

Glu Ser Cys Gly Val Gly Gln Gly His Ala Glu Asn Gln Cys Val Ser
625                 630                 635                 640

Cys Arg Ala Gly Thr Tyr Tyr Asp Gly Ala Arg Glu Arg Cys Ile Leu
                645                 650                 655

Cys Pro Asn Gly Thr Phe Gln Asn Glu Glu Gly Gln Met Thr Cys Glu
            660                 665                 670

Pro Cys Pro Arg Pro Gly Asn Ser Gly Ala Leu Lys Thr Pro Glu Ala
        675                 680                 685

Trp Asn Met Ser Glu Cys Gly Gly Leu Cys Gln Pro Gly Glu Tyr Ser
690                 695                 700

Ala Asp Gly Phe Ala Pro Cys Gln Leu Cys Ala Leu Gly Thr Phe Gln
705                 710                 715                 720

Pro Glu Ala Gly Arg Thr Ser Cys Phe Pro Cys Gly Gly Gly Leu Ala
                725                 730                 735

Thr Lys His Gln Gly Ala Thr Ser Phe Gln Asp Cys Glu Thr Arg Val
            740                 745                 750

Gln Cys Ser Pro Gly His Phe Tyr Asn Thr Thr His Arg Cys Ile
        755                 760                 765

Arg Cys Pro Val Gly Thr Tyr Gln Pro Glu Phe Gly Lys Asn Asn Cys
770                 775                 780

Val Ser Cys Pro Gly Asn Thr Thr Asp Phe Asp Gly Ser Thr Asn
785                 790                 795                 800

Ile Thr Gln Cys Lys Asn Arg Arg Cys Gly Gly Glu Leu Gly Asp Phe
                805                 810                 815

Thr Gly Tyr Ile Glu Ser Pro Asn Tyr Pro Gly Asn Tyr Pro Ala Asn
```

-continued

```
                    820                 825                 830
Thr Glu Cys Thr Trp Thr Ile Asn Pro Pro Lys Arg Arg Ile Leu
            835                 840                 845

Ile Val Val Pro Glu Ile Phe Leu Pro Ile Glu Asp Asp Cys Gly Asp
        850                 855                 860

Tyr Leu Val Met Arg Lys Thr Ser Ser Asn Ser Val Thr Thr Tyr
865                 870                 875                 880

Glu Thr Cys Gln Thr Tyr Glu Arg Pro Ile Ala Phe Thr Ser Arg Ser
                885                 890                 895

Lys Lys Leu Trp Ile Gln Phe Lys Ser Asn Glu Gly Asn Ser Ala Arg
            900                 905                 910

Gly Phe Gln Val Pro Tyr Val Thr Tyr Asp Glu Asp Tyr Gln Glu Leu
        915                 920                 925

Ile Glu Asp Ile Val Arg Asp Gly Arg Leu Tyr Ala Ser Glu Asn His
    930                 935                 940

Gln Glu Ile Leu Lys Asp Lys Lys Leu Ile Lys Ala Leu Phe Asp Val
945                 950                 955                 960

Leu Ala His Pro Gln Asn Tyr Phe Lys Tyr Thr Ala Gln Glu Ser Arg
                965                 970                 975

Glu Met Phe Pro Arg Ser Phe Ile Arg Leu Leu Arg Ser Lys Val Ser
            980                 985                 990

Arg Phe Leu Arg Pro Tyr Lys
        995
```

```
<210> SEQ ID NO 15
<211> LENGTH: 993
<212> TYPE: PRT
<213> ORGANISM: Homo sapiens

<400> SEQUENCE: 15

Met Gly Ser Gly Arg Val Pro Gly Leu Cys Leu Leu Val Leu Leu Val
1               5                   10                  15

His Ala Arg Ala Ala Gln Tyr Ser Lys Ala Ala Gln Asp Val Asp Glu
            20                  25                  30

Cys Val Glu Gly Thr Asp Asn Cys His Ile Asp Ala Ile Cys Gln Asn
        35                  40                  45

Thr Pro Arg Ser Tyr Lys Cys Ile Cys Lys Ser Gly Tyr Thr Gly Asp
    50                  55                  60

Gly Lys His Cys Lys Asp Val Asp Glu Cys Glu Arg Glu Asp Asn Ala
65                  70                  75                  80

Gly Cys Val His Asp Cys Val Asn Ile Pro Gly Asn Tyr Arg Cys Thr
                85                  90                  95

Cys Tyr Asp Gly Phe His Leu Ala His Asp Gly His Asn Cys Leu Asp
            100                 105                 110

Val Asp Glu Cys Ala Glu Gly Asn Gly Gly Cys Gln Gln Ser Cys Val
        115                 120                 125

Asn Met Met Gly Ser Tyr Glu Cys His Cys Arg Glu Gly Phe Phe Leu
    130                 135                 140

Ser Asp Asn Gln His Thr Cys Ile Gln Arg Pro Glu Glu Gly Met Asn
145                 150                 155                 160

Cys Met Asn Lys Asn His Gly Cys Ala His Ile Cys Arg Glu Thr Pro
                165                 170                 175

Lys Gly Gly Ile Ala Cys Glu Cys Arg Pro Gly Phe Glu Leu Thr Lys
            180                 185                 190
```

-continued

```
Asn Gln Arg Asp Cys Lys Leu Thr Cys Asn Tyr Gly Asn Gly Gly Cys
        195                 200                 205

Gln His Thr Cys Asp Asp Thr Glu Gln Gly Pro Arg Cys Gly Cys His
        210                 215                 220

Ile Lys Phe Val Leu His Thr Asp Gly Lys Thr Cys Ile Glu Thr Cys
225                 230                 235                 240

Ala Val Asn Asn Gly Gly Cys Asp Ser Lys Cys His Asp Ala Ala Thr
                245                 250                 255

Gly Val His Cys Thr Cys Pro Val Gly Phe Met Leu Gln Pro Asp Arg
                260                 265                 270

Lys Thr Cys Lys Asp Ile Asp Glu Cys Arg Leu Asn Asn Gly Gly Cys
            275                 280                 285

Asp His Ile Cys Arg Asn Thr Val Gly Ser Phe Glu Cys Ser Cys Lys
        290                 295                 300

Lys Gly Tyr Lys Leu Leu Ile Asn Glu Arg Asn Cys Gln Asp Ile Asp
305                 310                 315                 320

Glu Cys Ser Phe Asp Arg Thr Cys Asp His Ile Cys Val Asn Thr Pro
                325                 330                 335

Gly Ser Phe Gln Cys Leu Cys His Arg Gly Tyr Leu Leu Tyr Gly Ile
            340                 345                 350

Thr His Cys Gly Asp Val Asp Glu Cys Ser Ile Asn Arg Gly Gly Cys
        355                 360                 365

Arg Phe Gly Cys Ile Asn Thr Pro Gly Ser Tyr Gln Cys Thr Cys Pro
        370                 375                 380

Ala Gly Gln Gly Arg Leu His Trp Asn Gly Lys Asp Cys Thr Glu Pro
385                 390                 395                 400

Leu Lys Cys Gln Gly Ser Pro Gly Ala Ser Lys Ala Met Leu Ser Cys
                405                 410                 415

Asn Arg Ser Gly Lys Lys Asp Thr Cys Ala Leu Thr Cys Pro Ser Arg
            420                 425                 430

Ala Arg Phe Leu Pro Glu Ser Glu Asn Gly Phe Thr Val Ser Cys Gly
        435                 440                 445

Thr Pro Ser Pro Arg Ala Ala Pro Ala Arg Ala Gly His Asn Gly Asn
        450                 455                 460

Ser Thr Asn Ser Asn His Cys His Glu Ala Ala Val Leu Ser Ile Lys
465                 470                 475                 480

Gln Arg Ala Ser Phe Lys Ile Lys Asp Ala Lys Cys Arg Leu His Leu
                485                 490                 495

Arg Asn Lys Gly Lys Thr Glu Glu Ala Gly Arg Ile Thr Gly Pro Gly
            500                 505                 510

Gly Ala Pro Cys Ser Glu Cys Gln Val Thr Phe Ile His Leu Lys Cys
        515                 520                 525

Asp Ser Ser Arg Lys Gly Lys Gly Arg Arg Ala Arg Thr Pro Pro Gly
        530                 535                 540

Lys Glu Val Thr Arg Leu Thr Leu Glu Leu Glu Ala Glu Val Arg Ala
545                 550                 555                 560

Glu Glu Thr Thr Ala Ser Cys Gly Leu Pro Cys Leu Arg Gln Arg Met
                565                 570                 575

Glu Arg Arg Leu Lys Gly Ser Leu Lys Met Leu Arg Lys Ser Ile Asn
            580                 585                 590

Gln Asp Arg Phe Leu Leu Arg Leu Ala Gly Leu Asp Tyr Glu Leu Ala
        595                 600                 605

His Lys Pro Gly Leu Val Ala Gly Glu Arg Ala Glu Pro Met Glu Ser
```

```
                610                 615                 620
Cys Arg Pro Gly Gln His Arg Ala Gly Thr Lys Cys Val Ser Cys Pro
625                 630                 635                 640

Gln Gly Thr Tyr Tyr His Gly Gln Thr Glu Gln Cys Val Pro Cys Pro
            645                 650                 655

Ala Gly Thr Phe Gln Glu Arg Glu Gly Gln Leu Ser Cys Asp Leu Cys
                660                 665                 670

Pro Gly Ser Asp Ala His Gly Pro Leu Gly Ala Thr Asn Val Thr Thr
            675                 680                 685

Cys Ala Gly Gln Cys Pro Pro Gly Gln His Ser Val Asp Gly Phe Lys
690                 695                 700

Pro Cys Gln Pro Cys Pro Arg Gly Thr Tyr Gln Pro Glu Ala Gly Arg
705                 710                 715                 720

Thr Leu Cys Phe Pro Cys Gly Gly Leu Thr Thr Lys His Glu Gly
            725                 730                 735

Ala Ile Ser Phe Gln Asp Cys Asp Thr Lys Val Gln Cys Ser Pro Gly
                740                 745                 750

His Tyr Tyr Asn Thr Ser Ile His Arg Cys Ile Arg Cys Ala Met Gly
            755                 760                 765

Ser Tyr Gln Pro Asp Phe Arg Gln Asn Phe Cys Ser Arg Cys Pro Gly
770                 775                 780

Asn Thr Ser Thr Asp Phe Asp Gly Ser Thr Ser Val Ala Gln Cys Lys
785                 790                 795                 800

Asn Arg Gln Cys Gly Gly Glu Leu Gly Glu Phe Thr Gly Tyr Ile Glu
                805                 810                 815

Ser Pro Asn Tyr Pro Gly Asn Tyr Pro Ala Gly Val Glu Cys Ile Trp
            820                 825                 830

Asn Ile Asn Pro Pro Lys Arg Lys Ile Leu Ile Val Val Pro Glu
835                 840                 845

Ile Phe Leu Pro Ser Glu Asp Glu Cys Gly Asp Val Leu Val Met Arg
850                 855                 860

Lys Asn Ser Ser Pro Ser Ser Ile Thr Thr Tyr Glu Thr Cys Gln Thr
865                 870                 875                 880

Tyr Glu Arg Pro Ile Ala Phe Thr Ala Arg Ser Arg Lys Leu Trp Ile
            885                 890                 895

Asn Phe Lys Thr Ser Glu Ala Asn Ser Ala Arg Gly Phe Gln Ile Pro
            900                 905                 910

Tyr Val Thr Tyr Asp Glu Asp Tyr Glu Gln Leu Val Glu Asp Ile Val
            915                 920                 925

Arg Asp Gly Arg Leu Tyr Ala Ser Glu Asn His Gln Glu Ile Leu Lys
930                 935                 940

Asp Lys Lys Leu Ile Lys Ala Phe Phe Glu Val Leu Ala His Pro Gln
945                 950                 955                 960

Asn Tyr Phe Lys Tyr Thr Glu Lys His Lys Glu Met Leu Pro Lys Ser
            965                 970                 975

Phe Ile Lys Leu Leu Arg Ser Lys Val Ser Ser Phe Leu Arg Pro Tyr
            980                 985                 990

Lys

<210> SEQ ID NO 16
<211> LENGTH: 2292
<212> TYPE: DNA
<213> ORGANISM: Homo sapiens
<220> FEATURE:
```

-continued

```
<221> NAME/KEY: CDS
<222> LOCATION: (1)...(2292)

<400> SEQUENCE: 16 agc ggg ctc cca ggg tca gtc gac gtg gat gag tgc tca gag ggc aca      48
Ser Gly Leu Pro Gly Ser Val Asp Val Asp Glu Cys Ser Glu Gly Thr
 1               5                  10                  15 gat gac tgc cac atc gat gcc atc tgt cag aac gcg ccc aag tcc tac      96
Asp Asp Cys His Ile Asp Ala Ile Cys Gln Asn Ala Pro Lys Ser Tyr
             20                  25                  30 aaa tgc ctc tgc aag cca ggc tac aag ggg gaa ggc aag cag tgt gga     144
Lys Cys Leu Cys Lys Pro Gly Tyr Lys Gly Glu Gly Lys Gln Cys Gly
         35                  40                  45 gac att gac gag tgt gag aat gac tac tac aat ggg ggc tgt gtc cac     192
Asp Ile Asp Glu Cys Glu Asn Asp Tyr Tyr Asn Gly Gly Cys Val His
 50                  55                  60 gag tgc atc aac atc ccg ggg aac tac agg tgt acc tgc ttt gat ggc     240
Glu Cys Ile Asn Ile Pro Gly Asn Tyr Arg Cys Thr Cys Phe Asp Gly
 65                  70                  75                  80 ttc atg ctg gca cac gat gga cac aac tgc ctg gat gtg gac gag tgt     288
Phe Met Leu Ala His Asp Gly His Asn Cys Leu Asp Val Asp Glu Cys
             85                  90                  95 cag gac aat aat ggt ggc tgc cag cag atc tgc gtc aat gcc atg ggc     336
Gln Asp Asn Asn Gly Gly Cys Gln Gln Ile Cys Val Asn Ala Met Gly
        100                 105                 110 agc tac gag tgt cag tgc cac agt ggc ttc ttc ctt agt gac aac cag     384
Ser Tyr Glu Cys Gln Cys His Ser Gly Phe Phe Leu Ser Asp Asn Gln
        115                 120                 125 cat acc tgc atc cac cgc tcc aat gag ggt atg aac tgc atg aac aaa     432
His Thr Cys Ile His Arg Ser Asn Glu Gly Met Asn Cys Met Asn Lys
        130                 135                 140 gac cat ggc tgt gcc cac atc tgc cgg gag acg ccc aaa ggt ggg gtg     480
Asp His Gly Cys Ala His Ile Cys Arg Glu Thr Pro Lys Gly Gly Val
145                 150                 155                 160 gcc tgc gac tgc agg ccc ggc ttt gac ctt gcc caa aac cag aag gac     528
Ala Cys Asp Cys Arg Pro Gly Phe Asp Leu Ala Gln Asn Gln Lys Asp
                165                 170                 175 tgc aca cta acc tgt aat tat gga aac gga ggc tgc cag cac agc tgt     576
Cys Thr Leu Thr Cys Asn Tyr Gly Asn Gly Gly Cys Gln His Ser Cys
            180                 185                 190 gag gac aca gac aca ggc ccc acg tgt ggt tgc cac cag aag tac gcc     624
Glu Asp Thr Asp Thr Gly Pro Thr Cys Gly Cys His Gln Lys Tyr Ala
        195                 200                 205 ccc cac tca gac ggt cgc acg tgc atc gag acg tgc gca gtc aat aac     672
Pro His Ser Asp Gly Arg Thr Cys Ile Glu Thr Cys Ala Val Asn Asn
        210                 215                 220 gga ggc tgc gac cgg aca tgc aag gac aca gcc act ggc gtg cga tgc     720
Gly Gly Cys Asp Arg Thr Cys Lys Asp Thr Ala Thr Gly Val Arg Cys
225                 230                 235                 240 agc tgc ccc gtt gga ttc aca ctg cag ccg gac ggg aag aca tgc aaa     768
Ser Cys Pro Val Gly Phe Thr Leu Gln Pro Asp Gly Lys Thr Cys Lys
                245                 250                 255 gac atc aac gag tgc ctg gtc aac aac gga ggc tgc gac cac ttc tgc     816
Asp Ile Asn Glu Cys Leu Val Asn Asn Gly Gly Cys Asp His Phe Cys
            260                 265                 270 cgc aac acc gta ggc agc ttc gag tgc ggc tgc cgg aag ggc tac aag     864
Arg Asn Thr Val Gly Ser Phe Glu Cys Gly Cys Arg Lys Gly Tyr Lys
        275                 280                 285 ctg ctc acc gac gag cgc acc tgc cag gac atc gac gag tgc tcc ttc     912
Leu Leu Thr Asp Glu Arg Thr Cys Gln Asp Ile Asp Glu Cys Ser Phe
```

```
                        290                 295                 300
gag cgg acc tgt gac cac atc tgc atc aac tcc ccg ggc agc ttc cag           960
Glu Arg Thr Cys Asp His Ile Cys Ile Asn Ser Pro Gly Ser Phe Gln
305                 310                 315                 320 tgc ctg tgt cac cgc ggc tac atc ctc tac ggg aca acc cac tgc gga          1008
Cys Leu Cys His Arg Gly Tyr Ile Leu Tyr Gly Thr Thr His Cys Gly
                325                 330                 335 gat gtg gac gag tgc agc atg agc aac ggg agc tgt gac cag ggc tgc          1056
Asp Val Asp Glu Cys Ser Met Ser Asn Gly Ser Cys Asp Gln Gly Cys
            340                 345                 350 gtc aac acc aag ggc agc tac gag tgc gtc tgt ccc ccg ggg agg cgg          1104
Val Asn Thr Lys Gly Ser Tyr Glu Cys Val Cys Pro Pro Gly Arg Arg
        355                 360                 365 ctc cac tgg aac cgg aag gat tgc gtg gag aca ggc aag tgt ctt tct          1152
Leu His Trp Asn Arg Lys Asp Cys Val Glu Thr Gly Lys Cys Leu Ser
    370                 375                 380 cgc gcc aag acc tcc ccc cgg gcc cag ctg tcc tgc agc aag gca ggc          1200
Arg Ala Lys Thr Ser Pro Arg Ala Gln Leu Ser Cys Ser Lys Ala Gly
385                 390                 395                 400 ggt gtg gag agc tgc ttc ctt tcc tgc ccg gct cac aca ctc ttc gtg          1248
Gly Val Glu Ser Cys Phe Leu Ser Cys Pro Ala His Thr Leu Phe Val
                405                 410                 415 cca gac tcg gaa aat agc tac gtc ctg agc tgc gga gtt cca ggg ccg          1296
Pro Asp Ser Glu Asn Ser Tyr Val Leu Ser Cys Gly Val Pro Gly Pro
            420                 425                 430 cag ggc aag gcg ctg cag aaa cgc aac ggc acc agc tct ggc ctc ggg          1344
Gln Gly Lys Ala Leu Gln Lys Arg Asn Gly Thr Ser Ser Gly Leu Gly
        435                 440                 445 ccc agc tgc tca gat gcc ccc acc acc ccc atc aaa cag aag gcc cgc          1392
Pro Ser Cys Ser Asp Ala Pro Thr Thr Pro Ile Lys Gln Lys Ala Arg
    450                 455                 460 ttc aag atc cga gat gcc aag tgc cac ctc cgg ccc cac agc cag gca          1440
Phe Lys Ile Arg Asp Ala Lys Cys His Leu Arg Pro His Ser Gln Ala
465                 470                 475                 480 cga gca aag gag acc gcc agg cag ccg ctg ctg gac cac tgc cat gtg          1488
Arg Ala Lys Glu Thr Ala Arg Gln Pro Leu Leu Asp His Cys His Val
                485                 490                 495 act ttc gtg acc ctc aag tgt gac tcc tcc aag aag agg cgc gtt ggc          1536
Thr Phe Val Thr Leu Lys Cys Asp Ser Ser Lys Lys Arg Arg Val Gly
            500                 505                 510 cgc aag tcc cca tcc aag gag gtg tcc cac att aca gca gag ttt gag          1584
Arg Lys Ser Pro Ser Lys Glu Val Ser His Ile Thr Ala Glu Phe Glu
        515                 520                 525 atc gag aca aag atg gaa gag gcc tca gac aca tgc gaa gcg gac tgc          1632
Ile Glu Thr Lys Met Glu Glu Ala Ser Asp Thr Cys Glu Ala Asp Cys
    530                 535                 540 ttg cgg aag cga gca gaa cag agc ctg cag gcc gcc atc aag acc ctg          1680
Leu Arg Lys Arg Ala Glu Gln Ser Leu Gln Ala Ala Ile Lys Thr Leu
545                 550                 555                 560 cgc aag tcc atc ggc cgg cag cag ttc tat gtc cag gtc tca ggc act          1728
Arg Lys Ser Ile Gly Arg Gln Gln Phe Tyr Val Gln Val Ser Gly Thr
                565                 570                 575 gag tac gag gta gcc cag agg cca gcc aag gcg ctg gag ggg cag ggg          1776
Glu Tyr Glu Val Ala Gln Arg Pro Ala Lys Ala Leu Glu Gly Gln Gly
            580                 585                 590 gca tgt ggc gca ggc cag gtg cta cag gac agc aaa tgc gtt gcc tgt          1824
Ala Cys Gly Ala Gly Gln Val Leu Gln Asp Ser Lys Cys Val Ala Cys
        595                 600                 605 ggg cct ggc acc cac ttc ggt ggt gag ctc ggc cag tgt gtg cca tgt          1872
```

-continued

```
                Gly Pro Gly Thr His Phe Gly Gly Glu Leu Gly Gln Cys Val Pro Cys
                    610                 615                 620 atg cca gga aca tac cag gac atg gaa ggc cag ctc agt tgc aca ccg       1920
Met Pro Gly Thr Tyr Gln Asp Met Glu Gly Gln Leu Ser Cys Thr Pro
625                 630                 635                 640 tgc ccc agc agc gac ggg ctt ggt ctg cct ggt gcc cgc aac gtg tcg       1968
Cys Pro Ser Ser Asp Gly Leu Gly Leu Pro Gly Ala Arg Asn Val Ser
                645                 650                 655 gaa tgt gga ggc cag tgt tct cca ggc ttc ttc tcg gcc gat ggc ttc       2016
Glu Cys Gly Gly Gln Cys Ser Pro Gly Phe Phe Ser Ala Asp Gly Phe
            660                 665                 670 aag ccc tgc cag gcc tgc ccc gtg ggc acg tac cag cct gag ccc ggg       2064
Lys Pro Cys Gln Ala Cys Pro Val Gly Thr Tyr Gln Pro Glu Pro Gly
        675                 680                 685 cgc acc ggc tgc ttc ccc tgt gga ggg ggt ttg ctc acc aaa cac gaa       2112
Arg Thr Gly Cys Phe Pro Cys Gly Gly Gly Leu Leu Thr Lys His Glu
    690                 695                 700 ggc acc acc tcc ttc cag gac tgc gag gct aaa gtg cac tgc tcc ccc       2160
Gly Thr Thr Ser Phe Gln Asp Cys Glu Ala Lys Val His Cys Ser Pro
705                 710                 715                 720 ggc cac cac tac aac acc acc acc cac cgc tgc atc cgc tgc ccc gtc       2208
Gly His His Tyr Asn Thr Thr Thr His Arg Cys Ile Arg Cys Pro Val
                725                 730                 735 ggc acc tac cag ccc gag ttt ggc cag aac cac tgc atc acc tgt ccg       2256
Gly Thr Tyr Gln Pro Glu Phe Gly Gln Asn His Cys Ile Thr Cys Pro
            740                 745                 750 ggc aac acc agc aca gac ttc gat ggc tcc acc aac                       2292
Gly Asn Thr Ser Thr Asp Phe Asp Gly Ser Thr Asn
        755                 760
```

<210> SEQ ID NO 17
<211> LENGTH: 764
<212> TYPE: PRT
<213> ORGANISM: Homo sapiens

<400> SEQUENCE: 17

```
Ser Gly Leu Pro Gly Ser Val Asp Val Asp Glu Cys Ser Glu Gly Thr
1               5                   10                  15

Asp Asp Cys His Ile Asp Ala Ile Cys Gln Asn Ala Pro Lys Ser Tyr
            20                  25                  30

Lys Cys Leu Cys Lys Pro Gly Tyr Lys Gly Glu Gly Lys Gln Cys Gly
        35                  40                  45

Asp Ile Asp Glu Cys Glu Asn Asp Tyr Tyr Asn Gly Gly Cys Val His
    50                  55                  60

Glu Cys Ile Asn Ile Pro Gly Asn Tyr Arg Cys Thr Cys Phe Asp Gly
65                  70                  75                  80

Phe Met Leu Ala His Asp Gly His Asn Cys Leu Asp Val Asp Glu Cys
                85                  90                  95

Gln Asp Asn Asn Gly Gly Cys Gln Gln Ile Cys Val Asn Ala Met Gly
            100                 105                 110

Ser Tyr Glu Cys Gln Cys His Ser Gly Phe Phe Leu Ser Asp Asn Gln
        115                 120                 125

His Thr Cys Ile His Arg Ser Asn Glu Gly Met Asn Cys Met Asn Lys
    130                 135                 140

Asp His Gly Cys Ala His Ile Cys Arg Glu Thr Pro Lys Gly Gly Val
145                 150                 155                 160

Ala Cys Asp Cys Arg Pro Gly Phe Asp Leu Ala Gln Asn Gln Lys Asp
                165                 170                 175
```

-continued

```
Cys Thr Leu Thr Cys Asn Tyr Gly Asn Gly Gly Cys Gln His Ser Cys
            180                 185                 190

Glu Asp Thr Asp Thr Gly Pro Thr Cys Gly Cys His Gln Lys Tyr Ala
            195                 200                 205

Pro His Ser Asp Gly Arg Thr Cys Ile Glu Thr Cys Ala Val Asn Asn
            210                 215                 220

Gly Gly Cys Asp Arg Thr Cys Lys Asp Thr Ala Thr Gly Val Arg Cys
225                 230                 235                 240

Ser Cys Pro Val Gly Phe Thr Leu Gln Pro Asp Gly Lys Thr Cys Lys
            245                 250                 255

Asp Ile Asn Glu Cys Leu Val Asn Asn Gly Gly Cys Asp His Phe Cys
            260                 265                 270

Arg Asn Thr Val Gly Ser Phe Glu Cys Gly Cys Arg Lys Gly Tyr Lys
            275                 280                 285

Leu Leu Thr Asp Glu Arg Thr Cys Gln Asp Ile Asp Glu Cys Ser Phe
            290                 295                 300

Glu Arg Thr Cys Asp His Ile Cys Ile Asn Ser Pro Gly Ser Phe Gln
305                 310                 315                 320

Cys Leu Cys His Arg Gly Tyr Ile Leu Tyr Gly Thr Thr His Cys Gly
            325                 330                 335

Asp Val Asp Glu Cys Ser Met Ser Asn Gly Ser Cys Asp Gln Gly Cys
            340                 345                 350

Val Asn Thr Lys Gly Ser Tyr Glu Cys Val Cys Pro Pro Gly Arg Arg
            355                 360                 365

Leu His Trp Asn Arg Lys Asp Cys Val Glu Thr Gly Lys Cys Leu Ser
            370                 375                 380

Arg Ala Lys Thr Ser Pro Arg Ala Gln Leu Ser Cys Ser Lys Ala Gly
385                 390                 395                 400

Gly Val Glu Ser Cys Phe Leu Ser Cys Pro Ala His Thr Leu Phe Val
            405                 410                 415

Pro Asp Ser Glu Asn Ser Tyr Val Leu Ser Cys Gly Val Pro Gly Pro
            420                 425                 430

Gln Gly Lys Ala Leu Gln Lys Arg Asn Gly Thr Ser Ser Gly Leu Gly
            435                 440                 445

Pro Ser Cys Ser Asp Ala Pro Thr Thr Pro Ile Lys Gln Lys Ala Arg
            450                 455                 460

Phe Lys Ile Arg Asp Ala Lys Cys His Leu Arg Pro His Ser Gln Ala
465                 470                 475                 480

Arg Ala Lys Glu Thr Ala Arg Gln Pro Leu Leu Asp His Cys His Val
            485                 490                 495

Thr Phe Val Thr Leu Lys Cys Asp Ser Ser Lys Lys Arg Arg Arg Gly
            500                 505                 510

Arg Lys Ser Pro Ser Lys Glu Val Ser His Ile Thr Ala Glu Phe Glu
            515                 520                 525

Ile Glu Thr Lys Met Glu Glu Ala Ser Asp Thr Cys Glu Ala Asp Cys
            530                 535                 540

Leu Arg Lys Arg Ala Glu Gln Ser Leu Gln Ala Ala Ile Lys Thr Leu
545                 550                 555                 560

Arg Lys Ser Ile Gly Arg Gln Gln Phe Tyr Val Gln Val Ser Gly Thr
            565                 570                 575

Glu Tyr Glu Val Ala Gln Arg Pro Ala Lys Ala Leu Glu Gly Gln Gly
            580                 585                 590
```

```
Ala Cys Gly Ala Gly Gln Val Leu Gln Asp Ser Lys Cys Val Ala Cys
            595                 600                 605

Gly Pro Gly Thr His Phe Gly Gly Glu Leu Gly Gln Cys Val Pro Cys
    610                 615                 620

Met Pro Gly Thr Tyr Gln Asp Met Glu Gly Gln Leu Ser Cys Thr Pro
625                 630                 635                 640

Cys Pro Ser Ser Asp Gly Leu Gly Leu Pro Gly Ala Arg Asn Val Ser
                645                 650                 655

Glu Cys Gly Gly Gln Cys Ser Pro Gly Phe Phe Ser Ala Asp Gly Phe
            660                 665                 670

Lys Pro Cys Gln Ala Cys Pro Val Gly Thr Tyr Gln Pro Glu Pro Gly
        675                 680                 685

Arg Thr Gly Cys Phe Pro Cys Gly Gly Gly Leu Leu Thr Lys His Glu
    690                 695                 700

Gly Thr Thr Ser Phe Gln Asp Cys Glu Ala Lys Val His Cys Ser Pro
705                 710                 715                 720

Gly His His Tyr Asn Thr Thr Thr His Arg Cys Ile Arg Cys Pro Val
                725                 730                 735

Gly Thr Tyr Gln Pro Glu Phe Gly Gln Asn His Cys Ile Thr Cys Pro
            740                 745                 750

Gly Asn Thr Ser Thr Asp Phe Asp Gly Ser Thr Asn
        755                 760

<210> SEQ ID NO 18
<211> LENGTH: 1158
<212> TYPE: DNA
<213> ORGANISM: Homo sapiens
<220> FEATURE:
<221> NAME/KEY: CDS
<222> LOCATION: (1)...(1158)

<400> SEQUENCE: 18 agc ggg ctc cca ggg tca gtc gac gtg gat gag tgc tca gag ggc aca        48
Ser Gly Leu Pro Gly Ser Val Asp Val Asp Glu Cys Ser Glu Gly Thr
1               5                   10                  15 gat gac tgc cac atc gat gcc atc tgt cag aac gcg ccc aag tcc tac        96
Asp Asp Cys His Ile Asp Ala Ile Cys Gln Asn Ala Pro Lys Ser Tyr
            20                  25                  30 aaa tgc ctc tgc aag cca ggc tac aag ggg gaa ggc aag cag tgt gga       144
Lys Cys Leu Cys Lys Pro Gly Tyr Lys Gly Glu Gly Lys Gln Cys Gly
        35                  40                  45 gac att gac gag tgt gag aat gac tac tac aat ggg ggc tgt gtc cac       192
Asp Ile Asp Glu Cys Glu Asn Asp Tyr Tyr Asn Gly Gly Cys Val His
    50                  55                  60 gag tgc atc aac atc ccg ggg aac tac agg tgt acc tgc ttt gat ggc       240
Glu Cys Ile Asn Ile Pro Gly Asn Tyr Arg Cys Thr Cys Phe Asp Gly
65                  70                  75                  80 ttc atg ctg gca cac gat gga cac aac tgc ctg gat gtg gac gag tgt       288
Phe Met Leu Ala His Asp Gly His Asn Cys Leu Asp Val Asp Glu Cys
                85                  90                  95 cag gac aat aat ggt ggc tgt cag cag atc tgc gtc aat gcc atg ggc       336
Gln Asp Asn Asn Gly Gly Cys Gln Gln Ile Cys Val Asn Ala Met Gly
            100                 105                 110 agc tac gag tgt cag tgc cac agt ggc ttc ttc ctt agt gac aac cag       384
Ser Tyr Glu Cys Gln Cys His Ser Gly Phe Phe Leu Ser Asp Asn Gln
        115                 120                 125 cat acc tgc atc cac cgc tcc aat gag ggt atg aac tgc atg aac aaa       432
His Thr Cys Ile His Arg Ser Asn Glu Gly Met Asn Cys Met Asn Lys
    130                 135                 140
```

```
gac cat ggc tgt gcc cac atc tgc cgg gag acg ccc aaa ggt ggg gtg       480
Asp His Gly Cys Ala His Ile Cys Arg Glu Thr Pro Lys Gly Gly Val
145                 150                 155                 160 gcc tgc gac tgc agg ccc ggc ttt gac ctt gcc caa aac cag aag gac       528
Ala Cys Asp Cys Arg Pro Gly Phe Asp Leu Ala Gln Asn Gln Lys Asp
                165                 170                 175 tgc aca cta acc tgt aat tat gga aac gga ggc tgc cag cac agc tgt       576
Cys Thr Leu Thr Cys Asn Tyr Gly Asn Gly Gly Cys Gln His Ser Cys
            180                 185                 190 gag gac aca gac aca ggc ccc acg tgt ggt tgc cac cag aag tac gcc       624
Glu Asp Thr Asp Thr Gly Pro Thr Cys Gly Cys His Gln Lys Tyr Ala
                195                 200                 205 ccc cac tca gac ggt cgc acg tgc atc gag acg tgc gca gtc aat aac       672
Pro His Ser Asp Gly Arg Thr Cys Ile Glu Thr Cys Ala Val Asn Asn
        210                 215                 220 gga ggc tgc gac cgg aca tgc aag gac aca gcc act ggc gtg cga tgc       720
Gly Gly Cys Asp Arg Thr Cys Lys Asp Thr Ala Thr Gly Val Arg Cys
225                 230                 235                 240 agc tgc ccc gtt gga ttc aca ctg cag ccg gac ggg aag aca tgc aaa       768
Ser Cys Pro Val Gly Phe Thr Leu Gln Pro Asp Gly Lys Thr Cys Lys
                245                 250                 255 gac atc aac gag tgc ctg gtc aac aac gga ggc tgc gac cac ttc tgc       816
Asp Ile Asn Glu Cys Leu Val Asn Asn Gly Gly Cys Asp His Phe Cys
            260                 265                 270 cgc aac acc gta ggc agc ttc gag tgc ggc tgc cgg aag ggc tac aag       864
Arg Asn Thr Val Gly Ser Phe Glu Cys Gly Cys Arg Lys Gly Tyr Lys
                275                 280                 285 ctg ctc acc gac gag cgc acc tgc cag gac atc gac gag tgc tcc ttc       912
Leu Leu Thr Asp Glu Arg Thr Cys Gln Asp Ile Asp Glu Cys Ser Phe
290                 295                 300 gag cgg acc tgt gac cac atc tgc atc aac tcc ccg ggc agc ttc cag       960
Glu Arg Thr Cys Asp His Ile Cys Ile Asn Ser Pro Gly Ser Phe Gln
305                 310                 315                 320 tgc ctg tgt cac cgc ggc tac atc ctc tac ggg aca acc cac tgc gga      1008
Cys Leu Cys His Arg Gly Tyr Ile Leu Tyr Gly Thr Thr His Cys Gly
                325                 330                 335 gat gtg gac gag tgc agc atg agc aac ggg agc tgt gac cag ggc tgc      1056
Asp Val Asp Glu Cys Ser Met Ser Asn Gly Ser Cys Asp Gln Gly Cys
                340                 345                 350 gtc aac acc aag ggc agc tac gag tgc gtc tgt ccc ccg ggg agg cgg      1104
Val Asn Thr Lys Gly Ser Tyr Glu Cys Val Cys Pro Pro Gly Arg Arg
                355                 360                 365 ctc cac tgg aac cgg aag gat tgc gtg gag aca ggc aag tgt ctt tct      1152
Leu His Trp Asn Arg Lys Asp Cys Val Glu Thr Gly Lys Cys Leu Ser
370                 375                 380 cgc gcc                                                               1158
Arg Ala
385
```

<210> SEQ ID NO 19
<211> LENGTH: 386
<212> TYPE: PRT
<213> ORGANISM: Homo sapiens

<400> SEQUENCE: 19

```
Ser Gly Leu Pro Gly Ser Val Asp Val Asp Glu Cys Ser Glu Gly Thr
1               5                   10                  15

Asp Asp Cys His Ile Asp Ala Ile Cys Gln Asn Ala Pro Lys Ser Tyr
            20                  25                  30
```

-continued

```
Lys Cys Leu Cys Lys Pro Gly Tyr Lys Gly Glu Gly Lys Gln Cys Gly
         35                  40                  45

Asp Ile Asp Glu Cys Glu Asn Asp Tyr Tyr Asn Gly Gly Cys Val His
 50                  55                  60

Glu Cys Ile Asn Ile Pro Gly Asn Tyr Arg Cys Thr Cys Phe Asp Gly
 65                  70                  75                  80

Phe Met Leu Ala His Asp Gly His Asn Cys Leu Asp Val Asp Glu Cys
                 85                  90                  95

Gln Asp Asn Asn Gly Gly Cys Gln Gln Ile Cys Val Asn Ala Met Gly
             100                 105                 110

Ser Tyr Glu Cys Gln Cys His Ser Gly Phe Phe Leu Ser Asp Asn Gln
             115                 120                 125

His Thr Cys Ile His Arg Ser Asn Glu Gly Met Asn Cys Met Asn Lys
         130                 135                 140

Asp His Gly Cys Ala His Ile Cys Arg Glu Thr Pro Lys Gly Gly Val
145                 150                 155                 160

Ala Cys Asp Cys Arg Pro Gly Phe Asp Leu Ala Gln Asn Gln Lys Asp
                 165                 170                 175

Cys Thr Leu Thr Cys Asn Tyr Gly Asn Gly Gly Cys Gln His Ser Cys
             180                 185                 190

Glu Asp Thr Asp Thr Gly Pro Thr Cys Gly Cys His Gln Lys Tyr Ala
             195                 200                 205

Pro His Ser Asp Gly Arg Thr Cys Ile Glu Thr Cys Ala Val Asn Asn
         210                 215                 220

Gly Gly Cys Asp Arg Thr Cys Lys Asp Thr Ala Thr Gly Val Arg Cys
225                 230                 235                 240

Ser Cys Pro Val Gly Phe Thr Leu Gln Pro Asp Gly Lys Thr Cys Lys
                 245                 250                 255

Asp Ile Asn Glu Cys Leu Val Asn Asn Gly Gly Cys Asp His Phe Cys
             260                 265                 270

Arg Asn Thr Val Gly Ser Phe Glu Cys Gly Cys Arg Lys Gly Tyr Lys
         275                 280                 285

Leu Leu Thr Asp Glu Arg Thr Cys Gln Asp Ile Asp Glu Cys Ser Phe
290                 295                 300

Glu Arg Thr Cys Asp His Ile Cys Ile Asn Ser Pro Gly Ser Phe Gln
305                 310                 315                 320

Cys Leu Cys His Arg Gly Tyr Ile Leu Tyr Gly Thr Thr His Cys Gly
                 325                 330                 335

Asp Val Asp Glu Cys Ser Met Ser Asn Gly Ser Cys Asp Gln Gly Cys
             340                 345                 350

Val Asn Thr Lys Gly Ser Tyr Glu Cys Val Cys Pro Pro Gly Arg Arg
             355                 360                 365

Leu His Trp Asn Arg Lys Asp Cys Val Glu Thr Gly Lys Cys Leu Ser
         370                 375                 380

Arg Ala
385
```

<210> SEQ ID NO 20
<211> LENGTH: 15
<212> TYPE: PRT
<213> ORGANISM: Artificial Sequence
<220> FEATURE:
<223> OTHER INFORMATION: peptide

<400> SEQUENCE: 20

-continued

```
Glu Cys Ser Glu Gly Thr Asp Asp Cys His Ile Asp Ala Ile Cys
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: peptide

<400> SEQUENCE: 21

Lys Ala Arg Phe Lys Ile Arg Asp Ala Lys Cys His Leu Arg Pro His
1               5                   10                  15

Ser

<210> SEQ ID NO 22
<211> LENGTH: 16
<212> TYPE: PRT
<213> ORGANISM: Artificial Sequence
<220> FEATURE:
<223> OTHER INFORMATION: peptide

<400> SEQUENCE: 22

Ser His Ile Cys Lys Glu Ala Pro Arg Gly Ser Val Ala Cys Glu Cys
1               5                   10                  15

<210> SEQ ID NO 23
<211> LENGTH: 19
<212> TYPE: PRT
<213> ORGANISM: Artificial Sequence
<220> FEATURE:
<223> OTHER INFORMATION: peptide

<400> SEQUENCE: 23

Phe Leu Arg Cys His Ser Gly Ile His Leu Ser Ser Asp Val Thr Thr
1               5                   10                  15

Ile Arg Thr
```

IDENTIFICATION OF A FAMILY OF SECRETED PROTEINS IN VASCULAR ENDOTHELIUM

CROSS-REFERENCE TO RELATED APPLICATION

This application is a continuation of U.S. patent application Ser. No. 10/406,073, filed Apr. 3, 2003 now U.S. Pat. No. 7,258,988, which claims the benefit of U.S. Provisional Application No. 60/369,876, filed Apr. 5, 2002. The entire contents of each of these applications are incorporated herein by this reference.

FIELD OF THE INVENTION

The invention relates generally to gene expression in vascular endothelial cells. The invention specifically relates to the discovery of a novel gene and protein family referred to herein as SCUBE1, SCUBE2 and SCUBE3 genes and proteins which can be expressed in endothelial cells. These genes and proteins may be involved in a variety of pathophysiological processes, such as cardiovascular disease, hemostasis, thrombosis, inflammatory disease, bone metabolism disorders, urinary bladder disorders and breast disorders.

The present invention includes novel proteins encoded by a cDNA and/or by genomic DNA and proteins similar to it, namely, new proteins bearing sequence similarity to SCUBE1, SCUBE2 and SCUBE3 proteins, nucleic acids that encode these proteins or fragments thereof, and binding partners, such as antibodies, that bind specifically to a protein of the invention.

BACKGROUND OF THE INVENTION

Vascular Endothelium

Endothelium is composed of a single layer of flattened transparent squamous cells, joined edge to edge in such a manner as to form a membrane of cells. This is found on the free surfaces of the serous membranes, as the lining membrane of the heart, blood vessels and lymphatics. Endothelial cells also line the surface of the brain and spinal cord, as well as the anterior surface of the eye. Endothelial tissue originates from the mesoderm of the embryo, while epithelium arises only from the ectoderm or endoderm (Gray, H. in: Gray's Anatomy. Pick and Howden, eds., pp. 1083 and 1154, Bounty Books, New York, 1977).

Vascular endothelium forms a continuous, single-cell-thick layer which lines the entire circulatory system. Despite its microscopic dimensions (often less than 1 micron in thickness), this living tissue is a multifunctional organ whose health is essential to normal vascular physiology and whose dysfunction can be a critical factor in the pathogenesis of vascular disease. Anatomically, the vascular endothelium forms the physical boundary separating the intravascular compartment from all of the tissues and organs of the body. Biologically, this interface supports a number of vital functions.

First and foremost, the vascular endothelium comprises a "container" for blood. As long as this cellular layer remains intact and is functioning normally, a non-thrombogenic surface is presented to the circulating blood, thus allowing it to remain fluid and perform its nutritive functions unimpeded by intravascular clotting. Physical disruption of the endothelial lining, even on a microscopic scale, elicits an immediate hemostatic response, involving localized activation of the coagulation cascade and the adherence and aggregation of platelets, an adaptive reaction that serves to limit blood loss at sites of injury. Conversely, acute or chronic impairment of the non-thrombogenic properties of the intact endothelial lining (a form of endothelial dysfunction, see below) can be an important predisposing factor for intravascular thrombosis.

Because of its unique anatomical location, the vascular endothelium also functions as a selectively permeable barrier. Macromolecules encountering various regional specializations of the endothelium, including cell surface glycocalyx, cell-cell junctional complexes, microvesicles, transcellular channels and subendothelial extracellular matrix, are enhanced or retarded in their movement from (or into) the intravascular space. Selectivity of this barrier function typically reflects the size and/or charge of the permeant molecule, but may also involve active metabolic processing on the part of the endothelial cell. Enhanced permeability to plasma macromolecules, such as albumin, is a hallmark of acute inflammation, and, in the case of lipoproteins, is an important part of atherosclerotic lesion development. Pathophysiologic stimuli, as well as therapeutic drugs, that can modulate this endothelial function thus have potential clinical relevance.

Another functionally important consequence of the location of the vascular endothelium is its ability to monitor, integrate and transduce blood-borne signals. Through expression of cell surface receptors for various cytokines (IL-1α,β, TNF-α, IFN-γ, TGF-β), growth factors and other hormones (e.g., basic FGF, VEGF/VPF, insulin and insulin-like growth factors), as well as bacterial products, (e.g., Gram-negative endotoxins such as lipopolysaccharides (LPS) and related binding proteins), and their intracellular coupling, via second messenger cascades, to the metabolic and transcriptional generation of other biological effector molecules, endothelial cells function as important tissue response regulators. At every site in the circulatory system they are sensing and responding to the local pathophysiological milieu, and can help propagate these responses transmurally, from the intimal lining into the walls of larger vessels (e.g., coronary arteries), or from the luminal surface of capillaries directly into the interstitium of adjacent tissues (e.g., myocardium). This sensing and transducing function extends beyond classical humoral stimuli to the biotransduction of distinct types of mechanical forces generated by pulsatile blood flow (e.g., fluid shear stresses, circumferential wall stress and transmural pressure).

Endothelium is capable of generating a diverse array of biologically active substances, including lipid mediators, cytokines, growth factors and other hormone-like substances, many of which serve as important biological effector molecules, influencing the behavior of multiple cells and tissues. Some act directly within their cell of origin in a so-called autocrine mode, whereas others act on adjacent cells (within the vessel wall or in the blood) in a paracrine mode. Still other endothelial-derived mediators, such as hematopoietic colony-stimulating factors (GM-CSF, M-CSF) are secreted into the circulation to act at a distance, analogous to classical hormones. In addition to being the source of cytokines, growth factors and hormones, the endothelium also is an important target of their actions. Indeed, the capacity for the endothelium to undergo, local or systemic, "activation" in response to such stimuli, with resultant dramatic changes in functional status, is an important aspect of its biology and pathobiology. First demonstrated in the case of MHC-II histocompatibility antigen upregulation by T-lymphocyte products, and then extended to the induction of procoagulant tissue factor activity and endothelial-leukocyte adhesion molecules by inflammatory cytokines and bacterial endotoxin, the phenomenon of "endothelial activation" has become an important paradigm for modulation of endothelial phenotype. It provides a conceptual model that encompasses both physiological adaptation and pathophysiological dysregulation.

Given its interface location, integrating and transducing capability, and the vast repertoire of its biologically active products, the endothelium plays a pivotal role in a series of pathophysiologic events. In each, endothelial-derived agonists and antagonists dynamically interact in the regulation of important processes that can have both local and systemic ramifications, such as hemostasis and thrombosis, vascular tone, vascular growth and remodeling, and inflammatory and immune reactions. At any given time, factors influencing the activation state or functional integrity of the endothelium determine the relative set-points of each of these balances. For example, the intact, unactivated vascular endothelial lining is non-thrombogenic, because the net activity of anti-thrombotic factors, such as prostacyclin, thrombomodulin, cell surface heparin-like glycosaminoglycans and ecto-ADPases, exceeds that of the various pro-thrombotic factors potentially also generated by the endothelium. The controlled expression of certain of these pro-thrombotic factors in response to local vascular trauma (e.g., thrombin-induced von Willebrand factor release) can function adaptively, as part of a response-to-injury reaction; conversely, decreased production of anti-thrombotic factors (e.g., prostacyclin, tissue plasminogen activator) may contribute to intravascular thrombosis and vital organ damage.

Similarly, imbalances in endothelial-derived smooth muscle relaxants versus endothelial-derived vasoconstrictors can influence local circulatory dynamics, as well as systemic blood pressure. The vascular endothelium is the source of some of the most potent naturally occurring vasoactive substances known, including nitric oxide and related substances (originally described as an EDRF, or "endothelium-dependent relaxing factor", by Furchgott and Zawadski) and endothelin-1, a novel peptide that resembles the lethal toxin in the venom of certain vipers whose bite can induce coronary vasospasm. Other factors in this endothelial vasomotor balance include prostacyclin, angiotensin II (generated by angiotensin converting enzyme at the luminal interface) and platelet-derived growth factor. The latter can be generated by endothelial cells and, in addition to its mitogenic properties, also is a potent smooth muscle contractile agonist.

Under normal conditions, the cells of the vessel wall are essentially growth quiescent, but following experimental endothelial denudation, a burst of medial smooth muscle migration and division is triggered, which then subsides as endothelial regeneration occurs. This well orchestrated wound healing response presumably reflects not only the localized generation or release of growth stimulators but also a transient, relative deficiency in endothelial-derived growth inhibitors. The resultant intimal hyperplasia is very similar to that which occurs in early atherosclerotic lesions. The more complex issues of sustained smooth muscle hyperplasia, secondary to immune-mediated endothelial damage in transplant-associated arteriosclerosis, or in the post-angioplasty setting, as well as the interplay of angiogenic and anti-angiogenic factors in neovascularization phenomena in ischemic myocardium and peripheral tissues may also reflect imbalances in endothelial-derived growth regulators.

It is now increasingly clear that biomechanical stimuli derived from flowing blood can modulate the phenotype of endothelial cells. An important aspect of this phenomenon is the ability of these forces to alter the patterns of genes expressed by vascular endothelium. A growing body of in vitro experimental data has demonstrated that when cultured endothelial cells are subjected to defined biomechanical stimuli they can manifest alterations in gene expression. Interestingly, many of the genes that have been demonstrated to be regulated by these stimuli have been found to be expressed in vascular endothelium in vivo.

Vascular diseases including thrombotic complications are a major cause of death in the industrialized world. Examples of these complications include acute myocardial infarction, unstable angina, chronic stable angina, transient ischemic attacks, strokes, peripheral vascular disease, preeclampsia, deep venous thrombosis, embolism, disseminated intravascular coagulation and thrombotic cytopenic purpura, thrombotic disorders, inflammatory disorders, chronic vascular disease, autoimmune disorders, transplant vasculopathy/rejection, atherosclerosis, hypertension, aneurysmal disease, vasospastic syndromes, ischemic coronary syndromes, cerebral vascular disease, angiogenic (both pro and anti) processes, and wound healing. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and prostheses.

SUMMARY OF THE INVENTION

The present invention is based on the discovery of a new gene family referred to as SCUBE, genes containing a secretory signal region, a chain of EGF-like domains, and a CUB domain, that can be differentially expressed in human endothelial cells compared to other human cell types.

The invention includes isolated nucleic acid molecules selected from the group consisting of isolated nucleic acid molecules that encode an amino acid sequence of SEQ ID NO: 2, 4, 17 or 19, an isolated nucleic acid molecule that encodes a fragment of at least 10 amino acids of SEQ ID NO: 2, 4, 17 or 19, and an isolated nucleic acid molecule which hybridizes to the complement of a nucleic acid molecule comprising SEQ ID NO: 1, 3, 16 or 18.

The present invention also includes isolated nucleic acid molecules selected from the group consisting of isolated nucleic acid molecules that encode an amino acid sequence of SEQ ID NO:6 or 8, an isolated nucleic acid molecule that encodes a fragment of at least 10 amino acids of SEQ ID NO:6 or 8 and an isolated nucleic acid molecule which hybridizes to the complement of a nucleic acid molecule comprising SEQ ID NO:5 or 7.

The present invention also includes isolated nucleic acid molecules selected from the group consisting of isolated nucleic acid molecules that encode an amino acid sequence of SEQ ID NO:6 or 8, an isolated nucleic acid molecule that encodes a fragment of at least 10 amino acids of SEQ ID NO:6 or 8 and an isolated nucleic acid molecule which hybridizes to the complement of a nucleic acid molecule comprising SEQ ID NO:5 or 7.

Nucleic acid molecules of the invention can encode a protein having at least about 85% amino acid sequence identity to SEQ ID NO: 2, 17, or 19, preferably at least about 86-90% sequence identity, and even more preferably at least about 91-100% sequence identity to SEQ ID NO: 2, 17 or 19. Nucleic acid molecules of the invention also can encode a protein having at least about 92% amino acid sequence identity to SEQ ID NO: 4, preferably at least about 93-95% sequence identity, and even more preferably at least about 96-100% sequence identity to SEQ ID NO: 4. Nucleic acid molecules of the invention also can encode a protein having at least about 85% amino acid sequence identity to SEQ ID NO:

6 or 8, preferably at least about 90-95% sequence identity, and even more preferably at least about 96, 97, 98, 99 or 100% sequence identity to SEQ ID NO: 6 or 8.

The present invention further includes the nucleic acid molecules operably linked to one or more expression control elements, including vectors comprising the isolated nucleic acid molecules. The invention further includes host cells transformed to contain the nucleic acid molecules of the invention and methods for producing a protein comprising the step of culturing a host cell transformed with a nucleic acid molecule of the invention under conditions in which the protein is expressed.

The invention further provides an isolated polypeptide selected from the group consisting of an isolated polypeptide comprising the amino acid sequence of SEQ ID NO: 2, 4, 17 or 19, an isolated polypeptide comprising a fragment of at least 10 amino acids of SEQ ID NO: 2, 4, 17 or 19, an isolated polypeptide comprising conservative amino acid substitutions of SEQ ID NO: 2, 4, 17 or 19, and an isolated polypeptide comprising naturally occurring amino acid sequence variants of SEQ ID NO: 2, 4, 17 or 19. Polypeptides of the invention also include polypeptides with an amino acid sequence having at least about 85% amino acid sequence identity with the sequence set forth in SEQ ID NO: 2, 17 or 19, preferably at least about 90%, more preferably at least about 95%, and most preferably at least about 98% sequence identity with the sequence set forth in SEQ ID NO: 2, 17 or 19. Polypeptides of the invention further include polypeptides with an amino acid sequence having at least about 92% amino acid sequence identity with the sequence set forth in SEQ ID NO: 4, preferably at least about 95%, and even more preferably at least about 98% sequence identity with the sequence set forth in SEQ ID NO: 4.

The invention further provides an isolated polypeptide selected from the group consisting of an isolated polypeptide comprising the amino acid sequence of SEQ ID NO: 6 or 8, an isolated polypeptide comprising a fragment of at least 10 amino acids of SEQ ID NO: 6 or 8, an isolated polypeptide comprising conservative amino acid substitutions of SEQ ID NO: 6 or 8, and an isolated polypeptide comprising naturally occurring amino acid sequence variants of SEQ ID NO: 6 or 8. Polypeptides of the invention also include polypeptides with an amino acid sequence having at least about 85% amino acid sequence identity with the sequence set forth in SEQ ID NO: 6 or 8, preferably at least about 90%, more preferably at least about 95%, and most preferably at least about 97%, 98% or 99% sequence identity with the sequence set forth in SEQ ID NO: 6 or 8.

The invention further provides an isolated antibody or antigen-binding antibody fragment that specifically binds to a SCUBE1, SCUBE2 or SCUBE3 polypeptide of the invention, including monoclonal and polyclonal antibodies. The invention also provides engineered antibodies, such as chimeric antibodies, humanized antibodies, bi- or multispecific antibodies, or antibodies or antigen-binding antibody fragments which have been engineered to include non-immunoglobulin polypeptide sequences.

The invention further provides methods of identifying an agent which modulates the expression of a nucleic acid molecule encoding a SCUBE protein of the invention, comprising: exposing cells which express the nucleic acid molecule to the agent; and determining whether the agent modulates expression of said nucleic acid molecule, thereby identifying an agent which modulates the expression of a nucleic acid molecule encoding the protein.

The invention further provides methods of identifying an agent which modulates the level of or at least one activity of a SCUBE protein of the invention, comprising: exposing cells which express the protein to the agent; and determining whether the agent modulates the level of or at least one activity of said protein, thereby identifying an agent which modulates the level of or at least one activity of the protein.

The invention further provides methods of identifying binding partners for a SCUBE protein of the invention, comprising: exposing said protein to a potential binding partner; and determining if the potential binding partner binds to said protein, thereby identifying binding partners for the protein.

The present invention further provides methods of modulating the expression of a nucleic acid molecule encoding a SCUBE protein of the invention, comprising: administering an effective amount of an agent which modulates the expression of a nucleic acid molecule encoding the protein. The invention also provides methods of modulating at least one activity of a SCUBE protein of the invention, comprising: administering an effective amount of an agent which modulates at least one activity of the protein.

The present invention further includes non-human transgenic animals modified to contain the SCUBE nucleic acid molecules of the invention, or non-human transgenic animals modified to contain mutated nucleic acid molecules or deletions of SCUBE such that expression of the encoded SCUBE polypeptides of the invention is prevented.

The invention further provides methods of diagnosing vascular diseases, comprising: determining the level of expression of a nucleic acid molecule of the invention or polypeptide of the invention.

The invention further includes compositions comprising a diluent and a polypeptide or protein selected from the group consisting of an isolated polypeptide comprising the amino acid sequence of SEQ ID NO: 2, 4, 17 or 19, an isolated polypeptide comprising a fragment of at least 10 amino acids of SEQ ID NO: 2, 4, 17 or 19, an isolated polypeptide comprising conservative amino acid substitutions of SEQ ID NO: 2, 4, 17 or 19, naturally occurring amino acid sequence variants of SEQ ID NO: 2, 4, 17 or 19, an isolated polypeptide with an amino acid sequence having at least about 85% amino acid sequence identity with the sequence set forth in SEQ ID NO: 2, 17 or 19, preferably at least about 90%, more preferably at least about 95%, and most preferably at least about 98% sequence identity with the sequence set forth in SEQ ID NO: 2, 17 or 19, and an isolated polypeptide with an amino acid sequence having at least about 92% amino acid sequence identity with the sequence set forth in SEQ ID NO: 4, preferably at least about 95%, and even more preferably at least about 98% sequence identity with the sequence set forth in SEQ ID NO: 4.

The invention further includes compositions comprising a diluent and a polypeptide or protein selected from the group consisting of an isolated polypeptide comprising the amino acid sequence of SEQ ID NO: 6 or 8, an isolated polypeptide comprising a fragment of at least 10 amino acids of SEQ ID NO: 6 or 8, an isolated polypeptide comprising conservative amino acid substitutions of SEQ ID NO: 6 or 8, naturally occurring amino acid sequence variants of SEQ ID NO: 6 or 8, an isolated polypeptide with an amino acid sequence having at least about 85% amino acid sequence identity with the sequence set forth in SEQ ID NO: 6 or 8, preferably at least about 90%, more preferably at least about 95%, and most preferably at least about 97%, 98% or 99% sequence identity with the sequence set forth in SEQ ID NO: 6 or 8.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a SCUBE1, SCUBE2, or SCUBE3 molecule. In one embodiment, the capture probe is a nucleic acid, e.g., a probe complementary to a SCUBE1, SCUBE2, or SCUBE3 nucleic acid sequence. In another embodiment, the capture probe is a polypeptide, e.g., an antibody specific for SCUBE1, SCUBE2, or SCUBE3 polypeptides. Also featured is a method of analyzing a sample by contacting the sample to the aforementioned array and detecting binding of the sample to the array.

BRIEF DESCRIPTION OF THE DRAWINGS

FIG. 1 shows the amino acid sequence of human SCUBE1 (SEQ ID NO:2) as determined from a full-length cDNA clone. The signal peptide, EGF-like repeats and CUB domain are marked or underlined. Potential glycosylation sites are indicated by asterisks. The approximate margins of the C-termini of two deletion constructs in this study, D1 (SEQ ID NO:17) and D2 (SEQ ID NO:19), are marked. The estimated mature mass is 105,553 Da, and the pI is 6.7.

FIG. 3 demonstrates that human SCUBE1 is an uncleaved, secreted protein. a) Inclusion of endogenous signal peptide results in a secreted SCUBE1 protein. SCUBE1 tagged with Myc at the C-terminus (SCUBE1.Myc) is detected in the culture medium by anti-Myc antibody (WB=Western blot). b) Secreted SCUBE1 is the same size as the cell-associated form. Flag- and Myc-tagged SCUBE1 (at the N- and C-termini, respectively, Flag.SCUBE1.Myc) is detected in the culture medium by Western blotting with anti-Flag M2 or anti-Myc antibody. c) Secreted SCUBE1 is not a proteolytic product. Culture medium from cells transfected with Flag.SCUBE1.Myc was immunoprecipitated with anti-Flag M2 antibody, and then immunoblotted with either anti-Flag M2 or anti-Myc antiserum. (IP=immunoprecipitation). As in a and b, the secreted protein and the cell-associated protein are the same size.

FIG. 8 shows the homo-oligomerization of human SCUBE1 in transfected cells. a) When Flag-SCUBE1 and SCUBE1.Myc were co-transfected, the expressed protein molecules could be precipitated with anti-Myc antibody and detected with anti-Flag M2 antibody, or visa versa. b) When SCUBE1.Myc was co-transfected with Flag.SCUBE1-FL, Flag.SCUBE1-D1, or Flag.SCUBE1-D2, analysis of the cell lysates revealed polymeric proteins that could be immunoprecipitated with anti-Myc antibody and detected by immunoblotting with anti-Flag M2 antibody. Cell lysates were also immunoblotted to examine the protein expression levels. The polymeric proteins indicate that the EGF-like repeats, rather than the spacer or CUB domain, function in SCUBE1 homotypic associations.

FIG. 14A depicts the hydropathy plot of SCUBE3.1 (SEQ ID NO:6) and FIG. 14B depicts the hydropathy plot of SCUBE3.2 (SEQ ID NO:8). Relatively hydrophobic residues are shown above the dashed horizontal line, and relatively hydrophilic residues are below the dashed horizontal line. The cysteine residues (cys) are indicated by short vertical lines just below the hydropathy trace. The numbers corresponding to the amino acid sequence of human SCUBE3 are indicated. Polypeptides of the invention include fragments which include: all or part of a hydrophobic sequence, e.g., a sequence above the dashed line, e.g., the sequence from about amino acid 201 to 211 and from about 763 to 773 of SEQ ID NO:6; all or part of a hydrophilic sequence, e.g., a sequence below the dashed line, e.g., the sequence from about amino acid 28 to 41, from about 497 to 508, and from about 881 to 897 of SEQ ID NO:6; all or part of a hydrophobic sequence, e.g., a sequence above the dashed line, e.g., the sequence from about amino acid 254 to 268 and from about 842 to 852 of SEQ ID NO:8; all or part of a hydrophilic sequence, e.g., a sequence below the dashed line, e.g., the sequence from about amino acid 28 to 41, from about 529 to 540, and from about 960 to 976 of SEQ ID NO:8; and a sequence which includes a Cys, or a glycosylation site.

DETAILED DESCRIPTION OF THE INVENTION

I. General Description

Figure 2:
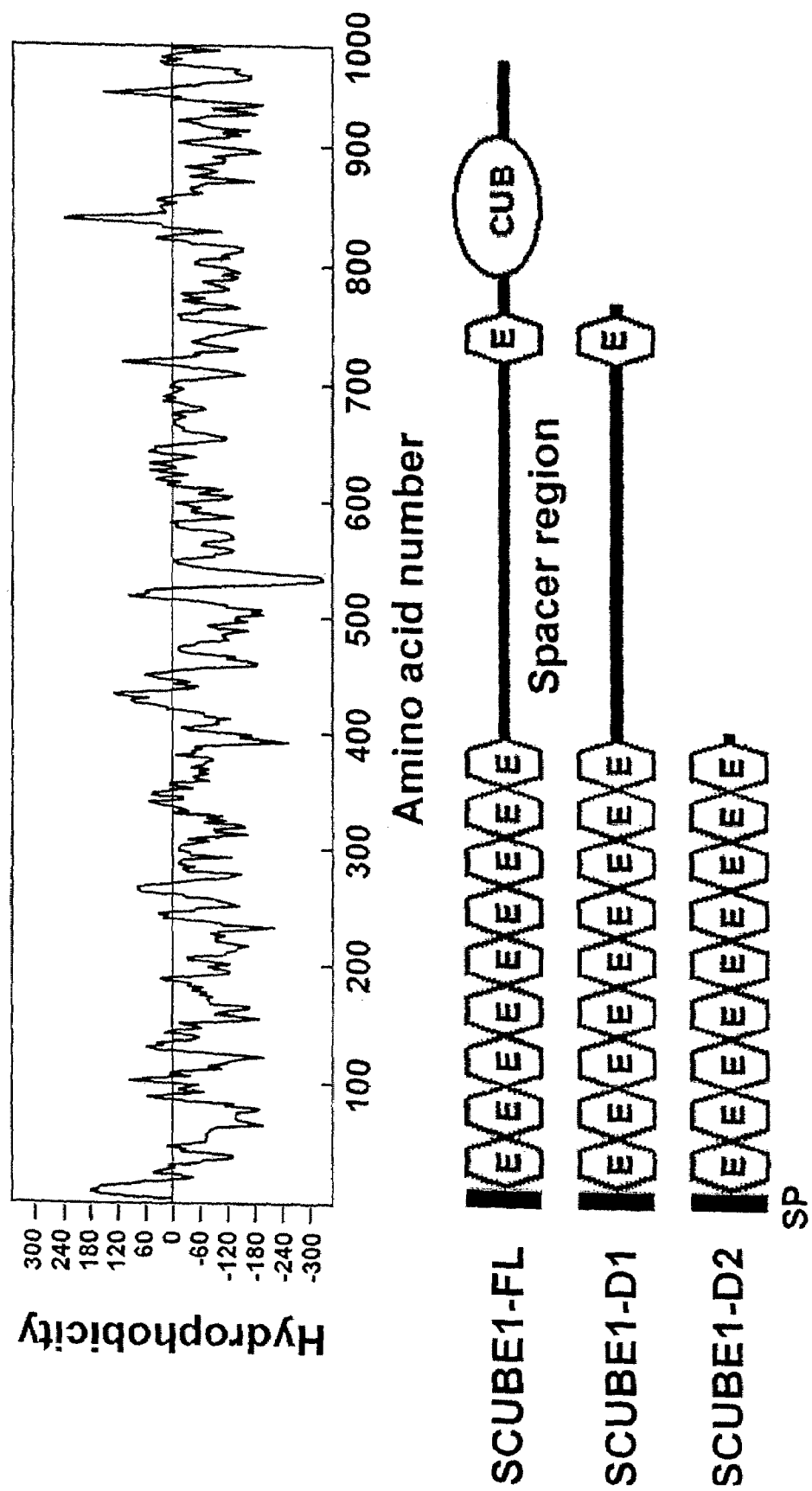
FIG. 2 shows a hydrophobicity plot and the domain structure of human SCUBE1. The plot was generated according to the methods of Kyte and Doolittle. The region marked with a thick line indicates the putative signal peptide (see FIG. 1). Polypeptides of the invention include fragments which include: all or part of a hydrophobic sequence, e.g., a sequence above the dashed line, e.g., the sequence from about amino acid 424 to 441 and from about 836 to 847 of SEQ ID NO:2; all or part of a hydrophilic sequence, e.g., a sequence below the dashed line, e.g., the sequence from about amino acid 55 to 71, from about 485 to 500, and from about 962 to 971 of SEQ ID NO:2. The lower panel shows the domain structure of SCUBE1 protein. In addition to EGF-like repeats and CUB domain, a spacer region is located between the 9$^{th}$ and 10$^{th}$ EGF-like repeat. FL=full-length; D1=deletion construct #1; D2=deletion construct #2; E=EGF-like repeats; CUB=CUB domain.

Vascular endothelial cells (EC) play a key role in a variety of physiologic and pathophysiologic processes, such as angiogenesis, inflammation, cancer metastasis and the development of vascular diseases. As a part of a strategy to identify genes that are differentially expressed in human EC, large-scale EST sequencing and expression profiling approaches were performed in human vascular EC cultured under various stimuli (flow, cytokine, angiogenic, etc). One full-length cDNA identified by these approaches encodes a secreted protein containing a signal peptide at the N-terminus followed by nine EGF-like domains, a spacer region, a tenth EGF-like domain and one CUB domain at the C-terminus (referred to herein as SCUBE1, Signal peptide-CUB-EGF-like domain-containing protein 1). A second cDNA identified by these approaches encodes SCUBE2, with an N-terminal signal peptide, eight EGF-like domains, a spacer region and a C-terminal CUB domain. A third set of sequences identified by homology, domain structure and expression analysis encodes the 47971 (gene MG44547) polypeptides, 47971-031 or SCUBE3.1, and Fbh47971FL or SCUBE3.2 referred to herein collectively as "SCUBE3," with an N-terminal signal peptide, nine EGF-like domains, a spacer region and a C-terminal CUB domain.

Northern and microarray analyses demonstrate that SCUBE1 is expressed in adults in several highly vascularized tissues such as liver, kidney, lung, spleen and brain. The endothelial-selective pattern of expression for SCUBE1 was further confirmed by in situ hybridization to these tissues. We have characterized the SCUBE1 gene product by using a transient expression system in human kidney embryonic (HEK-293) cells. Overproduction in these cells resulted in expression of SCUBE1 protein in the conditioned medium. Flow cytometry and immunofluorescence analyses showed that this protein could bind to and be displayed on the cell surface. Analyses of several deletion mutants of the SCUBE1 protein revealed that the spacer region between the EGF-like and CUB domains is critical for its secretion and cell-surface association. Furthermore, expression of SCUBE1 is decreased in EC after IL-1β and TNF-α treatment, suggesting a possible role for SCUBE1 in the inflammatory response. A second gene encoding a homologue (designated as SCUBE2) was also identified and appears to be expressed in an EC-specific fashion. These results were confirmed by immunohistochemical detection of SCUBE1 and SCUBE2 proteins at endothelial cells in vivo. When overexpressed, SCUBE1 and SCUBE2 can manifest homo- and heterotypic interactions. These results indicate that SCUBE1 and SCUBE2 define an emerging secreted protein family that is highly expressed in human vascular endothelium.

The SCUBE1 polypeptide was found by immunohistochemistry to be associated with thrombi in vessels. These thrombi were the result of acute bleeding events which did not allow time for new protein synthesis. Thus, during a thrombotic event, cell-associated SCUBE1 can be released into the plasma and recruited into the thrombus. Accordingly, SCUBE1 molecules of the invention can be used for the treatment and/or diagnosis of thrombotic disorders.

SCUBE2 mRNA was found at high levels in urge urinary incontinence (UUI) bladder and at lower levels in normal bladder. SCUBE2 also has high levels of expression in breast tumor and low levels of expression in normal breast. Accordingly, SCUBE2 molecules of the invention can be used for the treatment and/or diagnosis of urinary bladder disorders and breast disorders, e.g. breast tumor.

The SCUBE3 mRNA was found at high levels in osteoblasts and normal fetal kidney, at medium levels in normal artery, normal vein, fetal heart, normal adult heart, normal ventricle, umbilical cord and diseased aorta and at medium to low levels in ischemic ventricle. In contrast, SCUBE3 was found at low levels in idiopathic artery, ischemic artery, and coronary diseased artery, to indicate regulated expression of SCUBE3 in some disease processes. Another example of regulated SCUBE3 expression is the medium level of SCUBE3 expression in urge urinary incontinence (UUI) bladder tissue and only a trace level of expression in normal bladder. Accordingly, SCUBE3 molecules of the invention can be used for the treatment and/or diagnosis of cardiovascular diseases, e.g. vessel or heart calcification and ischemia, disorders of bone metabolism and urinary bladder disorders.

SCUBE3 gene maps to chromosome 6p21. The Paget's disease of bone is mapped to the 6p21 locus. Accordingly, SCUBE3 molecules of the invention can be used for the treatment and/or diagnosis of Paget's disease.

The present invention is based in part on the identification of a new gene that encodes SCUBE1 or SCUBE2 and that is differentially expressed in human endothelial cells as compared to other human cell types. These genes correspond to the human cDNAs of SEQ ID NO: 1, 16, or 18, hereinafter referred to collectively as "SCUBE1" or specifically as "SCUBE1," SCUBE1-D1," or SCUBE1-D2," respectively, and SEQ ID NO:3 (SCUBE2). Genes that encode the human SCUBE proteins of SEQ ID NO: 2, 4, 17 or 19 (SCUBE1, SCUBE2, SCUBE1-D1, SCUBE1-D2, respectively) may also be found in other animal species, particularly mammalian species.

The present invention also is based in part on the identification of a gene which encodes SCUBE3 and which is differentially expressed in cardiovascular tissues. This gene corresponds to the human cDNAs of SEQ ID NO:5 and 7. Genes that encode the human SCUBE3 protein of SEQ ID NO:6 and 8 may also be found in other animal species, particularly mammalian species.

The genes and proteins of the invention may be used as diagnostic agents or markers to detect or monitor the progression of diseases or conditions with vascular involvement in a subject or sample.

A. Cardiovascular Disease

SCUBE proteins may be implicated in cardiovascular disorders, including in atherosclerotic plaque formation. For example, SCUBE1 has been identified in thrombi of vessels (e.g. in kidney and spleen). In another example, SCUBE3 has regulated expression in arteries, with higher expression in normal arteries than in idiopathic diseased arteries and ischemic diseased arteries. Diseases such as cardiovascular disease, including cerebral thrombosis or hemorrhage, ischemic heart or renal disease, peripheral vascular disease, or thrombosis of other major vessel, and other diseases, including diabetes mellitus, hypertension, hypothyroidism, cholesterol ester storage disease, systemic lupus erythematosus, homocysteinemia, and familial protein or lipid processing diseases, and the like, are either directly or indirectly associated with atherosclerosis. Accordingly, therapeutics of the invention, particularly those that modulate (or supply) SCUBE activity or formation may be effective in treating or preventing atherosclerosis-associated diseases or disorders. Therapeutics of the invention (particularly therapeutics that modulate the levels or activity) can be assayed by any method known in the art, including those described below, for efficacy in treating or preventing such diseases and disorders.

A vast array of animal and cell culture models exist for processes involved in atherosclerosis. A limited and non-exclusive list of animal models includes knockout mice for premature atherosclerosis (Kurabayashi and Yazaki, 1996, Int. Angiol. 15: 187-194), transgenic mouse models of atherosclerosis (Kappel et al., 1994, FASEB J. 8: 583-592), antisense oligonucleotide treatment of animal models (Callow, 1995, Curr. Opin. Cardiol. 10: 569-576), transgenic rabbit models for atherosclerosis (Taylor, 1997, Ann. N.Y. Acad. Sci. 811: 146-152), hypercholesterolemic animal models (Rosenfeld, 1996, Diabetes Res. Clin. Pract. 30 Suppl.: 1-11), hyperlipidemic mice (Paigen et al., 1994, Curr. Opin. Lipidol. 5: 258-264), and inhibition of lipoxygenase in animals (Sigal et al., 1994, Ann. N.Y. Acad. Sci. 714: 211-224). In addition, in vitro cell models include but are not limited to monocytes exposed to low-density lipoprotein (Frostegard et al., 1996, Atherosclerosis 121: 93-103), cloned vascular smooth muscle cells (Suttles et al., 1995, Exp. Cell Res. 218: 331-338), endothelial cell-derived chemoattractant exposed T cells (Katz et al., 1994, J. Leukoc. Biol. 55: 567-573), cultured human aortic endothelial cells (Farber et al., 1992, Am. J. Physiol. 262: H1088-1085), and foam cell cultures (Libby et al., 1996, Curr Opin Lipidol 7: 330-335). Potentially effective therapeutics, for example but not by way of limitation, reduce foam cell formation in cell culture models, or reduce atherosclerotic plaque formation in hypercholesterolemic mouse models of atherosclerosis in comparison to controls.

Accordingly, once an atherosclerosis-associated disease or disorder has been shown to be amenable to treatment by modulation of activity or formation, that disease or disorder can be treated or prevented by administration of a therapeutic that modulates activity.

Other cardiovascular disorders in which SCUBE molecules of the invention can play a role include, but are not limited to disorders such as arteriosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, arrhythmia, sudden cardiac death, and cardiovascular developmental disorders.

B. Hemostatic and Thrombolytic Activity

A protein or a therapeutic of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

EGF-like domains, such as those found in SCUBE1, SCUBE 2 and SCUBE3, are components of proteins involved in the coagulation process, for example, thrombomodulin, protein C, protein S, protein Z and factors VII, IX, X and XII. Accordingly, SCUBE1 polypeptide can be found in thrombi of vessels. Therefore, SCUBE proteins may play an important role in coagulation and thrombosis formation, as well as in related diseases.

The activity of a protein of the invention may, among other means, be measured by the following methods. Assays for hemostatic and thrombolytic activity include, without limitation, those described in: Linet et al., *J. Clin. Pharmacol.* 26:131-140, 1986; Burdick et al., *Thrombosis Res.* 45:413-419, 1987; Humphrey et al., *Fibrinolysis* 5:71-79 (1991); and Schaub, *Prostaglandins* 35:467-474, 1988.

C. Receptor/Ligand Activity

A protein or a therapeutic of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell—cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods: Current Protocols in Immunology, Ed by Coligan, et al., Greene Publishing Associates and Wiley-Interscience (Chapter 7.28, Measurement of Cellular Adhesion under static conditions 7.28.1-7.28.22), Takai et al., *Proc Natl Acad Sci USA* 84:6864-6868, 1987; Bierer et al., *J. Exp. Med.* 168:1145-1156, 1988;

Rosenstein et al., *J. Exp. Med.* 169:149-160 1989; Stoltenborg et al., *J Immunol Methods* 175:59-68, 1994; Stitt et al., *Cell* 80:661-670, 1995.

D. Anti-Inflammatory Activity

SCUBE proteins or therapeutics of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions, including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, e.g. Crohn's disease and ulcerative colitis, or resulting from over production of cytokines such as TNF or IL-1. Molecules of the invention may also be useful to treat anaphylaxis, hypersensitivity to an antigenic substance or material and respiratory inflammatory disorders, e.g. asthma, allergic asthma, and chronic obstructive pulmonary disease. Further therapeutic uses of SCUBE molecules of the invention include autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, and Sjögren's Syndrome.

E. Disorders of Bone Metabolism

Aberrant expression and/or activity of SCUBE molecules, e.g. SCUBE3, can mediate disorders associated with bone metabolism. "Bone metabolism" refers to direct or indirect effects in the formation or degeneration of bone structures, e.g., bone formation, bone resorption, etc., which can ultimately affect the concentrations in serum of calcium and phosphate. This term also includes activities mediated by SCUBE molecules, e.g. SCUBE3, in bone cells, e.g. osteoblasts, that can in turn result in bone formation and degeneration. For example, SCUBE molecules, e.g. SCUBE3, can support different activities of bone resorbing osteoclasts such as the stimulation of differentiation of monocytes and mononuclear phagocytes into osteoclasts. Accordingly, SCUBE molecules, e.g. SCUBE3, that modulate the production of bone cells can influence bone formation and degeneration, and thus can be used to treat bone disorders. Examples of such disorders include, but are not limited to, Paget's disease, osteoporosis, osteodystrophy, osteomalacia, rickets, osteitis fibrosa cystica, renal osteodystrophy, osteosclerosis, anticonvulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

F. Urinary Bladder Disorders

Aberrant expression and/or activity of SCUBE molecules, e.g. SCUBE2 and SCUBE3, can mediate urinary bladder disorders. The activities mediated by SCUBE molecules, e.g. SCUBE2 and SCUBE3, in bladder cells, e.g. epithelial, capillary endothelial cells, and smooth muscle cells, can in turn result in urinary bladder function. Accordingly, SCUBE molecules, e.g. SCUBE2 and SCUBE3, can modulate urinary bladder function, and thus can be used to treat urinary bladder disorders. Examples of bladder disorders include, but are not limited to, urge urinary incontinence (UUI), overactive bladder, cystitis (e.g. tuberculous cystitis, radiation cystitis, ulcerative interstitial cystitis, emphysematous cystitis, malakoplakia lesions, cystitis cystica, and eosinophilic cystitis), diverticula, vesicoureteral reflux, and bladder neoplasms (e.g. transitional cell carcinoma, squamous cell carcinoma and adenocarcinoma).

G. Breast Disorders

Aberrant expression and/or activity of SCUBE molecules, e.g. SCUBE2, can mediate breast disorders. Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's breast disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

II. Specific Embodiments

A. SCUBE Proteins and Variants Thereof

The present invention provides isolated SCUBE proteins, allelic variants of the proteins, and conservative amino acid substitutions of the proteins. As used herein, the "protein" or "polypeptide" refers, in part, to a protein that has the human amino acid sequence depicted in SEQ ID NO: 2, 4, 17, 19, 6 or 8 or fragments thereof with or without the secretory signal region or signal peptide and spacer region. The terms also refer to naturally occurring allelic variants and proteins that have a slightly different amino acid sequence than those specifically recited above. Allelic variants, though possessing a slightly different amino acid sequence than those recited above, will still have the same or similar biological functions associated with these proteins.

As used herein, the SCUBE family of proteins related to the human amino acid sequence of SEQ ID NO: 2, 4, 17, 19, 6 or 8 refers in part, to proteins that have been isolated from organisms in addition to humans. A SCUBE family member can include at least one signal peptide, at least one, two, three, four, five, six, seven, preferably eight, nine or ten EGF-like domains, at least one spacer region and at least one CUB domain. The methods used to identify and isolate other members of the family of proteins related to these proteins are described below.

As used herein, the term "EGF-like domain" includes an amino acid sequence of about 15 to 50 amino acid residues in length and having a bit score for the alignment of the sequence to the EGF-like domain (HMM) of at least 5. (For reference to Pfam and Prosite annotation, see Example 8.) Preferably, an EGF-like domain includes six conserved cysteines involved in disulfide bonding to maintain the structure of the SCUBE EGF-like domain in an extracellular environment. The EGF-like domains typically can be repeated multiple times (nearly tandemly, in a region containing at least one, two, three, four, five, six, seven, preferably eight or nine EGF-like domains) in the N-terminal half of the SCUBE polypeptide. The EGF-like domains of SCUBE polypeptides can mediate binding of SCUBE molecules to polypeptides having a diphtheria toxin catalytic domain (Pfam PF02763), an immunoglobulin domain (Pfam PF00047), such as is found in a variety of proteins, e.g. antibodies, major histocompatibility complex molecules, and receptor tyrosine kinases, or a trypsin domain (Pfam PF00089) such as is found in a variety of serine proteases, e.g. enzymes of the coagulation system such as thrombin and plasminogen activator. Preferably, an EGF-like domain includes at least about 20 to 45 amino acids, more preferably about 25 to 40 amino acid residues, or about 32 to 37 amino acids and has a bit score for the alignment of the sequence to the EGF-like domain (HMM) of at least 5, 9, 14 or greater. An EGF-like domain can include an EGF-like domain signature 2 sequence (PS01186, SEQ ID NO:11) and/or a calcium-binding EGF-like domain signature sequence (PS01187, SEQ ID NO:12). The EGF-like domain (HMM) has been assigned the PFAM Accession Number PF00008 (SEQ ID NO:9).

As used herein, the term "spacer region" includes an amino acid sequence of about 350 to 475 amino acid residues in length. A spacer region can have asparagines-targeted glycosylation sites (N-glycosylation sites, Prosite PS00001). Preferably, a spacer region can mediate secretion and cell-surface association of a SCUBE polypeptide. A spacer region can interact with lectin-containing molecules. Preferably, a spacer region includes at least about 375 to 450 amino acids, more preferably about 390 to 430 amino acid residues. The spacer region of the SCUBE molecules typically can be found between the multiple repeated EGF-like domains and the CUB domain.

As used herein, the term "CUB domain" includes an amino acid sequence of about 90 to 130 amino acid residues in length and having a bit score for the alignment of the sequence to the CUB domain (HMM) of at least 50. A CUB domain can be found in developmentally regulated proteins and can have four conserved cysteines to form disulfide bonds and stabilize this domain in an extracellular environment. Preferably, a CUB domain includes at least about 95 to 125 amino acids, more preferably about 100 to 120 amino acid residues, or about 105 to 115 amino acids and has a bit score for the alignment of the sequence to the CUB domain (HMM) of at least 60, 65, 70 or greater. The CUB domain (HMM) has been assigned the PFAM Accession Number PF00431, SEQ ID NO:10.

The proteins of the present invention are preferably in isolated form. As used herein, a protein is said to be isolated when physical, mechanical or chemical methods are employed to remove the protein from cellular constituents that are normally associated with the protein. In one embodiment, the language "substantially purified" means preparation of SCUBE protein having less than about 30%, 20%, 10% and more preferably 5% (by dry weight), of non-SCUBE protein (also referred to herein as a "contaminating protein"), or of chemical precursors or non-SCUBE chemicals. When the SCUBE protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight. A skilled artisan can readily employ standard purification methods to obtain an isolated protein.

The proteins of the present invention further include insertion, deletion or conservative amino acid substitution variants of SEQ ID NO: 2, 4, 17, 19, 6 or 8. As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein can be altered without adversely affecting a biological activity. Accordingly, the amino acid sequence can be altered, for example to render the peptide more hydrophobic or hydrophilic, without adversely affecting the biological activities of the protein. In another example, a mutation which results in removal or replacement of a cysteine residue in an EGF-like domain or a CUB domain in a SCUBE polypeptide can have an adverse effect on the resulting SCUBE structure, extracellular half-life or activity. In another example, a mutation which results in removal or replacement of an asparagine in an N-glycosylation site in a spacer region of a SCUBE polypeptide can have an adverse effect on the secretion or the cell-surface association of the resulting SCUBE polypeptide.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a SCUBE protein is preferably replaced with another amino acid residue from the same side chain family. Alternatively, in another embodiment, mutations can be introduced randomly along all or part of a SCUBE coding sequence, such as by saturation mutagenesis, and the resultant mutants can be screened for SCUBE biological activity to identify mutants that retain activity. Following mutagenesis of SEQ ID NO:1, 16, 18, 3, 5, or 7, the encoded protein can be expressed recombinantly and the activity of the protein can be determined.

Ordinarily, the allelic variants, the conservative substitution variants, and the members of the protein family, will have an amino acid sequence having at least about 50%, 60%, 65%, 70% or 75% amino acid sequence identity with the sequence set forth in SEQ ID NO: 2, 4, 17 or 19, preferably at least about 80%, more preferably at least about 85%-90%, and most preferably at least about 91-95% sequence identity. A particularly preferred embodiment will have at least about 84% sequence identity to SEQ ID NO: 2, 17 or 19, more preferably at least about 85-90% sequence identity, and most preferably at least about 91-95% or 96 or 99% sequence identity. Another particularly preferred embodiment will have at least about 92% sequence identity to SEQ ID NO: 4, more preferably at least about 93-95% sequence identity, and most preferably at least about 96% or 99% sequence identity.

In another preferred embodiment, polypeptides will have an amino acid sequence having at least about 85% amino acid sequence identity with the sequence set forth in SEQ ID NO: 6 or 8, preferably at least about 90%, more preferably at least about 95%, and most preferably at least about 97%, 98% or 99% sequence identity with the sequence set forth in SEQ ID NO: 6 or 8.

Identity or homology with respect to such sequences is defined herein as the percentage of amino acid residues in the candidate sequence that are identical with the known peptides, after aligning the sequences and introducing gaps, if necessary, to achieve the maximum percent homology or alignment, and not considering any conservative substitutions as part of the sequence identity (see section B for the relevant parameters). Fusion proteins, or N-terminal, C-terminal or internal extensions, deletions, or insertions into the peptide sequence shall not be construed as affecting homology.

Thus, the proteins of the present invention include molecules having the amino acid sequence disclosed in SEQ ID NO: 2, 4, 17, 19, 6 or 8; fragments thereof having a consecutive sequence of at least about 6, 10, 15, 20, 25, 30, 35 or more amino acid residues of these proteins; amino acid sequence variants wherein one or more amino acid residues has been inserted N- or C-terminal to, or within, the disclosed coding sequence; and amino acid sequence variants of the disclosed sequence, or their fragments as defined above, that have been substituted by at least one residue. Such fragments, also referred to as peptides or polypeptides, may contain antigenic regions, functional regions of the protein identified as regions of the amino acid sequence which correspond to known protein domains, as well as regions of pronounced hydrophilicity. For instance, such regions or domains include EGF-like domains, the spacer region, the CUB domain and the like (for SCUBE1, see FIGS. 1 and 2; for SCUBE2, see Example 1 and FIG. 13 and for SCUBE3, see Example 8 and FIGS. 14A and 14B). The regions are all easily identifiable by using commonly available protein sequence analysis software such as MACVECTOR sequence analysis software (available from Accelrys, Inc., San Diego, Calif.).

Contemplated variants further include those containing predetermined mutations by, e.g., homologous recombination, site-directed or PCR mutagenesis, and the corresponding proteins of other animal species, including but not limited to rabbit, mouse, rat, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

In another aspect, the invention provides SCUBE chimeric or fusion proteins. As used herein, a SCUBE "chimeric protein" or "fusion protein" includes a SCUBE polypeptide linked to a non-SCUBE polypeptide. A "non-SCUBE polypeptide" refers to a polypeptide having an amino acid sequence corresponding to a protein which is not substantially homologous to the SCUBE protein, e.g., a protein which is different from the SCUBE protein and which is derived from the same or a different organism. The SCUBE polypeptide of the fusion protein can correspond to all or a portion e.g., a fragment described herein of a SCUBE amino acid sequence. In a preferred embodiment, a SCUBE fusion protein includes at least one (or two) biologically active portion of a SCUBE protein. The non-SCUBE polypeptide can be fused to the N-terminus or C-terminus of the SCUBE polypeptide. The fusion protein can include a moiety which has a high affinity for a ligand. For example, the fusion protein can be a GST-SCUBE fusion protein in which the SCUBE sequences are fused to the C-terminus of the GST sequences. In other examples, the fusion protein can have a FLAG epitope tag, a myc epitope tag or a polyhistidine (nickel affinity binding) tag. Such fusion proteins can facilitate the purification of recombinant SCUBE.

As described below, members of the family of proteins can be used: (1) as a diagnostic or cell marker; (2) to identify agents which modulate at least one activity of the protein; (3) to identify binding partners for the protein, (4) as an antigen to raise polyclonal or monoclonal antibodies, and (5) as a therapeutic agent or target.

B. Nucleic Acid Molecules

The present invention further provides nucleic acid molecules that encode the protein having SEQ ID NO: 2, 4, 17, 19, 6 or 8 and the related proteins herein described, preferably in isolated form. As used herein, "nucleic acid" is defined as RNA or DNA or related molecules that encodes a protein or peptide as defined above, is complementary to a nucleic acid sequence encoding such peptides, hybridizes to such a nucleic acid and remains stably bound to it under appropriate stringency conditions, or encodes a polypeptide sharing at least about 50%, 60%, 65%, 70% or 75% sequence identity, preferably at least about 80%, more preferably at least about 85%, and even more preferably at least about 90% or 95% or more identity with the peptide sequences. The "nucleic acid molecules" of the invention further include nucleic acid molecules that share at least about 50%, 60%, 65%, 70% or 75% sequence identity, preferably at least about 80%, more preferably at least about 85%, and even more preferably at least about 90% or 95% or more identity with the nucleotide sequence of SEQ ID NO: 1, 16, 18, 3, 5 or 7 or the open reading frames defined therein. A particularly preferred embodiment will have at least about 87% sequence identity to SEQ ID NO: 1, 16 or 18, more preferably at least about 88-90% sequence identity, and most preferably at least about 91-95% or 96 or 99% sequence identity. Another particularly preferred embodiment will have at least about 94% sequence identity to SEQ ID NO: 3, more preferably at least about 95-96% sequence identity, and most preferably at least about 97% or 99% sequence identity. Other particularly preferred embodiments will have at least about 85% sequence identity to SEQ ID NO: 5 or 7, more preferably at least about 90% sequence identity, even more preferably at least about 95-96% sequence identity, and most preferably at least about 97%, 98% or 99% sequence identity.

Specifically contemplated are genomic DNA, cDNA, mRNA and antisense molecules, as well as nucleic acids based on alternative backbones or including alternative bases whether derived from natural sources or synthesized. Such nucleic acids, however, are defined further as being novel and unobvious over any prior art nucleic acid including that which encodes, hybridizes under appropriate stringency conditions, or is complementary to nucleic acid encoding a protein according to the present invention.

Homology or identity at the nucleotide or amino acid sequence level is determined by BLAST (Basic Local Alignment Search Tool) analysis using the algorithm employed by the programs blastp, blastn, blastx, tblastn and tblastx (Altschul et al., *Nucleic Acids Res* 25:3389-3402, 1997, and Karlin et al., *Proc Natl Acad Sci USA* 87:2264-2268, 1990, both fully incorporated by reference) which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al., *Nature Genetics* 6:119-129, 1994, which is fully incorporated by reference. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix (Henikoff et al., *Proc Natl Acad Sci USA* 89: 10915-10919, 1992, fully incorporated by reference), recommended for query sequences over 85 in length (nucleotide bases or amino acids).

For blastn, the scoring matrix is set by the ratios of M (i.e., the reward score for a pair of matching residues) to N (i.e., the penalty score for mismatching residues), wherein the default values for M and N are +5 and −4, respectively. Four blastn parameters were adjusted as follows: Q=10 (gap creation penalty); R=10 (gap extension penalty); wink=1 (generates word hits at every wink$^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Stringent conditions" include those that (1) employ low ionic strength and high temperature for washing, for example, 0.015 M NaCl/0.0015 M sodium citrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal. Preferred molecules are those that hybridize under the above conditions to the complement of SEQ ID NO: 1 and which encode a functional protein. Even more preferred hybridizing molecules are those that hybridize under the above conditions to the complement strand of the open reading frame of SEQ ID NO: 1, 16, 18, 3, 5, or 7.

As used herein, a nucleic acid molecule is said to be "isolated" when the nucleic acid molecule is substantially separated from contaminant nucleic acid molecules encoding other polypeptides.

The present invention further provides fragments of the encoding nucleic acid molecule. As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein. For instance, fragments which encode peptides corresponding to predicted antigenic regions may be prepared. If the fragment is to be used as a nucleic acid probe or PCR primer, then the fragment length is chosen so as to obtain a relatively small number of false positives during probing/priming (see the discussion in Section H).

Fragments of the encoding nucleic acid molecules of the present invention (i.e., synthetic oligonucleotides) that are used as probes or specific primers for the polymerase chain reaction (PCR), or to synthesize gene sequences encoding proteins of the invention, can easily be synthesized by chemical techniques, for example, the phosphoramidite method of Matteucci et al., (*J Am Chem Soc* 103:3185-3191, 1981) or using automated synthesis methods. In addition, larger DNA segments can readily be prepared by well-known methods, such as synthesis of a group of oligonucleotides that define various modular segments of the gene, followed by ligation of oligonucleotides to build the complete modified gene.

A nucleic acid fragment can include a sequence corresponding to a domain, region, or functional site described herein. A nucleic acid fragment can also include one or more domain, region, or functional site described herein. Thus, for example, a SCUBE nucleic acid fragment can include a sequence encoding an EGF-like domain, a spacer region or a CUB domain of a SCUBE polypeptide, as described herein The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can readily employ any such label to obtain labeled variants of the nucleic acid molecules of the invention.

Modifications to the primary structure of the nucleic acid molecules by deletion, addition, or alteration of the nucleotide sequence can be made without destroying the activity of the encoded proteins. Such substitutions or other alterations result in proteins having an amino acid sequence falling within the contemplated scope of the present invention.

C. Isolation of Other Related Nucleic Acid Molecules

As described above, the identification and characterization of the nucleic acid molecule having SEQ ID NO: 1, 16, 18, 3, 5, or 7 allows a skilled artisan to isolate nucleic acid molecules that encode other members of the protein family in addition to the sequences herein described.

For instance, a skilled artisan can readily use the amino acid sequence of SEQ ID NO: 2, 4, 17, 19, 6, or 8 to generate antibody probes to screen expression libraries prepared from appropriate cells. Typically, polyclonal antiserum from mammals such as rabbits immunized with the purified protein (as described below) or monoclonal antibodies can be used to probe a mammalian cDNA or genomic expression library, such as lambda gtll library, to obtain the appropriate coding sequence for other members of the protein family. The cloned cDNA sequence can be expressed as a fusion protein, expressed directly using its own control sequences, or expressed by constructions using control sequences appropriate to the particular host used for expression of the enzyme.

Alternatively, a portion of the coding sequence herein described can be synthesized and used as a probe to retrieve DNA encoding a member of the protein family from any mammalian organism. Oligomers containing approximately 18-20 nucleotides (encoding about a 6-7 amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

Nucleic acid molecules encoding other members of the protein family may also be identified in existing genomic or other sequence information using any available computational method, including but not limited to: PSI-BLAST (Altschul, et al., *Nucleic Acids Res* 25:3389-3402, 1997); PHI-BLAST (Zhang, et al., *Nucleic Acids Res* 26:3986-3990, 1998), 3D-PSSM (Kelly et al., *J Mol Biol* 299(2): 499-520, 2000); and other computational analysis methods (Shi et al., *Biochem Biophys Res Commun* 262(1):132-138, 1999 and Matsunami et al., *Nature* 404(6778):601-604, 2000).

D. rDNA Molecules Containing a Nucleic Acid Molecule

The present invention further provides recombinant DNA molecules (rDNAs) that contain a coding sequence. As used herein, a rDNA molecule is a DNA molecule that has been subjected to molecular manipulation in situ. Methods for generating rDNA molecules are well known in the art, for example, see Sambrook et al., *Molecular Cloning—A Laboratory Manual*, 3d Ed., Cold Spring Harbor Laboratory Press, Cold Spring Harbor, N.Y., 2001. In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as *E. coli*. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from BioRad Laboratories, (Richmond, Calif.), pPL and pKK223 available from Pharmacia (Piscataway, N.J.).

Expression vectors compatible with eukaryotic cells, preferably those compatible with vertebrate cells, can also be used to form rDNA molecules that contain a coding sequence. Eukaryotic cell expression vectors, including viral vectors, are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., *J Mol Anal Genet* 1, 327-341, 1982) Alternatively, the selectable marker can be present on a separate plasmid, and the two vectors are introduced by co-transfection of the host cell, and selected by culturing in the appropriate drug for the selectable marker.

E. Host Cells Containing an Exogenously Supplied Coding Nucleic Acid Molecule

The present invention further provides host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells (NIH/3T3) available from the ATCC as CRL 1658, baby hamster kidney cells (BHK), and the like eukaryotic tissue culture cell lines.

Any prokaryotic host can be used to express a rDNA molecule encoding a protein of the invention. The preferred prokaryotic host is *E. coli*.

Transformation of appropriate cell hosts with a rDNA molecule of the present invention is accomplished by well-known methods that typically depend on the type of vector used and host system employed. With regard to transformation of prokaryotic host cells, electroporation and salt treatment methods are typically employed, see, for example, Cohen et al., *Proc Natl Acad Sci USA* 69:2110, 1972; and Sambrook et al. (supra). With regard to transformation of vertebrate cells with vectors containing rDNAs, electroporation, cationic lipid or salt treatment methods are typically employed, see, for example, Graham et al., *Virol* 52:456, 1973; or Wigler et al., *Proc Natl Acad Sci USA* 76:1373-1376, 1979.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *J*

*Mol. Bio.* 98:503, 1975, or Berent et al., *Biotech* 3:208, 1985, or the proteins produced from the cell assayed via an immunological method.

F. Production of Recombinant Proteins Using a rDNA Molecule

The present invention further provides methods for producing a protein of the invention using nucleic acid molecules herein described. In general terms, the production of a recombinant form of a protein typically involves the following steps:

A nucleic acid molecule is first obtained that encodes a protein of the invention, such as but not limited to a nucleic acid molecule comprising, consisting essentially of or consisting of SEQ ID NO: 1, 16, 18, 3, 5, or 7, or the open reading frame defined by nucleotides 21-2984 (2987 with the stop codon) of SEQ ID NO: 1, the open reading frame defined by nucleotides 81-2837 (or 2840 with the stop codon) of SEQ ID NO: 3, the open reading frame defined by nucleotides 449-3190 (or 3193 with the stop codon) of SEQ ID NO:5, or the open reading frame defined by nucleotides 443-3421 (or 3424 with the stop codon) of SEQ ID NO:7. If the encoding sequence is uninterrupted by introns, as are these open reading frames, it is directly suitable for expression in any host.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

G. Methods to Identify Binding Partners

Another embodiment of the present invention provides methods of isolating and identifying binding partners of proteins of the invention. In general, a protein of the invention is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner that bound to the protein of the invention can then be removed and further analyzed. To identify and isolate a binding partner, the entire protein, for instance a protein comprising the entire amino acid sequence of SEQ ID NO: 2, 4, 17, 19, 6, or 8 can be used. Alternatively, a fragment of the protein can be used.

As used herein, a cellular extract refers to a preparation or fraction which is made from a lysed or disrupted cell. The preferred source of cellular extracts will be cells derived from human endothelial tissue or from a human organ that is highly vascularized, such as kidney, liver or lung. Alternatively, cellular extracts may be prepared from normal tissue or available cell lines, particularly endothelial cell lines.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al., *Methods Mol Biol* 69:171-184, 1997, or Sauder et al., *J Gen Virol* 77:991-996, 1996, or identified through the use of epitope tagged proteins or GST fusion proteins.

Alternatively, the nucleic acid molecules of the invention can be used in a yeast two-hybrid system. The yeast two-hybrid system has been used to identify other protein partner pairs and can readily be adapted to employ the nucleic acid molecules herein described.

H. Methods to Identify Agents that Modulate the Expression of a Nucleic Acid Encoding the Gene Associated with Vascular Disease Another embodiment of the present invention provides methods for identifying agents that modulate the expression of a nucleic acid encoding a protein of the invention such as a protein having the amino acid sequence of SEQ ID NO: 2, 4, 17, 19, 6, or 8. Such assays may utilize any available means of monitoring for changes in the expression level of the nucleic acids of the invention. As used herein, an agent is said to modulate the expression of a nucleic acid of the invention if it is capable of up- or down-regulating expression of the nucleic acid in a cell.

In one assay format, cell lines that contain reporter gene fusions between SEQ ID NO:16, SEQ ID NO:18, the open reading frame defined by nucleotides 21-2984 of SEQ ID NO: 1, 81-2837 of SEQ ID NO:3, 449-3190 of SEQ ID NO:5, or the open reading frame defined by nucleotides 443-3421 of SEQ ID NO:7, and/or the 5' and/or 3' regulatory elements and any assayable fusion partner may be prepared. Numerous assayable fusion partners are known and readily available including the firefly luciferase gene and the gene encoding chloramphenicol acetyltransferase (Alam et al., *Anal Biochem* 188:245-254, 1990). Cell lines containing the reporter gene fusions are then exposed to the agent to be tested under appropriate conditions and time. Differential expression of the reporter gene between samples exposed to the agent and control samples identifies agents which modulate the expression of a nucleic acid of the invention.

Additional assay formats may be used to monitor the ability of the agent to modulate the expression of a nucleic acid encoding a protein of the invention, such as the protein having SEQ ID NO: 2, 4, 17, 19, 6, or 8. For instance, mRNA expression may be monitored directly by hybridization to the nucleic acids of the invention. Cell lines are exposed to the agent to be tested under appropriate conditions and time and total RNA or mRNA is isolated by standard procedures such those disclosed in Sambrook et al., *Molecular Cloning—A Laboratory Manual*, 3d Ed., Cold Spring Harbor Laboratory Press, Cold Spring Harbor, N.Y., 2001.

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al., (supra) or Ausubel et al., *Short Protocols in Molecular Biology*, 4th Ed., John Wiley & Sons, Inc., New York, 1999.

Hybridization conditions are modified using known methods, such as those described by Sambrook et al. and Ausubel et al. as required for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a silicon chip or a porous glass wafer. The wafer can then be exposed to total cellular RNA or polyA RNA from a sample under conditions in which the affixed sequences will specifically hybridize. Such solid supports and hybridization methods are widely available, for example, those disclosed by Beattie, (1995) WO 95/11755. By examining for the ability of a given probe to specifically hybridize to an RNA sample from an untreated cell population and from a cell population exposed to the agent, agents which up or down regulate the expression of a nucleic acid encoding the protein having the sequence of SEQ ID NO: 2, 4, 17, 19, 6, or 8 are identified.

Hybridization for qualitative and quantitative analysis of mRNAs may also be carried out by using an RNase Protection Assay (i.e., RPA, see Ma et al. *Methods* 10:273-238, 1996). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising 80% formamide, 40 mM Pipes, pH 6.4, 0.4 M NaCl and 1 mM EDTA. The resulting hybrids are then digested in a buffer comprising 40 µg/ml ribonuclease A and 2 µg/ml ribonuclease. After deactivation and extraction of extraneous proteins, the samples are loaded onto urea/polyacrylamide gels for analysis.

In another assay format, cells or cell lines are first identified which express the gene products of the invention physiologically. Cell and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Further, such cells or cell lines would be transduced or transfected with an expression vehicle (e.g., a plasmid or viral vector) construct comprising an operable non-translated 5'-promoter containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag or other detectable marker. Such a process is well known in the art (see Sambrook et al., supra).

Cells or cell lines transduced or transfected as outlined above are then contacted with agents under appropriate conditions; for example, the agent in a pharmaceutically acceptable excipient is contacted with cells in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells will be disrupted and the polypeptides of the lysate are fractionated such that a polypeptide fraction is pooled and contacted with an antibody to be further processed by immunological assay (e.g., ELISA, immunoprecipitation or Western blot). The pool of proteins isolated from the "agent-contacted" sample will be compared with a control sample where only the excipient is contacted with the cells and an increase or decrease in the immunologically generated signal from the "agent-contacted" sample compared to the control will be used to distinguish the effectiveness of the agent.

I. Methods to Identify Agents that Modulate the Level of or at Least One Activity of SCUBE Proteins and Production of Antibodies Another embodiment of the present invention provides methods for identifying agents that modulate at least one activity of a protein of the invention such as the protein having the amino acid sequence of SEQ ID NO: 2, 4, 17, 19, 6, or 8. Such methods or assays may utilize any means of monitoring or detecting the desired activity.

The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and F(ab')$_2$ fragments which can be generated by treating the antibody with an enzyme such as papain or pepsin, respectively.

A full-length SCUBE protein or, antigenic peptide fragment of SCUBE can be used as an immunogen or can be used to identify anti-SCUBE antibodies made with other immunogens, e.g., cells, membrane preparations, and the like. The antigenic peptide of SCUBE should include at least 8 amino acid residues of the amino acid sequence shown in SEQ ID NO:2, 4, 17, 19, 6, or 8 and encompasses an epitope of a SCUBE polypeptide. Preferably, the antigenic peptide includes at least 10 amino acid residues, more preferably at least 15 amino acid residues, even more preferably at least 20 amino acid residues, and most preferably at least 30 amino acid residues.

Fragments of SCUBE1 which include residues about 55 to 71, from about 485 to 500, and from about 962 to 971 of SEQ ID NO:2 can be used to make, e.g., used as immunogens or used to characterize the specificity of an antibody, antibodies against hydrophilic regions of the SCUBE1 protein (see FIG. 2). Similarly, fragments of SCUBE1 which include residues about 424 to 441 and from about 836 to 847 of SEQ ID NO:2 can be used to make an antibody against a hydrophobic region of the SCUBE protein. A fragment of SCUBE1 which includes residues about 37 to 401, or a subset thereof, e.g. about residues 37 to 120, about residues 121 to 241 or about residues 242 to 401 of SEQ ID NO:2, 17 or 19 can be used to make an antibody against the N-terminal EGF-repeat region of the SCUBE1 protein; a fragment of SCUBE1 which includes residues about 36 to 50 of SEQ ID NO:2, 17 or 19 (SEQ ID NO:20) can be used to make an antibody against the first EGF-like repeat of the SCUBE1 protein; a fragment of SCUBE1 which includes residues about 415 to 789, or a subset thereof, e.g. about residues 415 to 480, about 481 to 640, about 641 to 789 of SEQ ID NO:2 or 17, or about 487 to 503 of SEQ ID NO:2 or 17 (SEQ ID NO:21) can be used to make an antibody against the spacer region of the SCUBE1 protein; or a fragment of SCUBE1 which includes residues about 798 to 907, or a subset thereof, e.g. about residues 798 to 840, about residues 841 to 870 or about residues 871 to 907 of SEQ ID NO:2 can be used to make an antibody against the CUB domain of the SCUBE1 protein.

Figure 13:
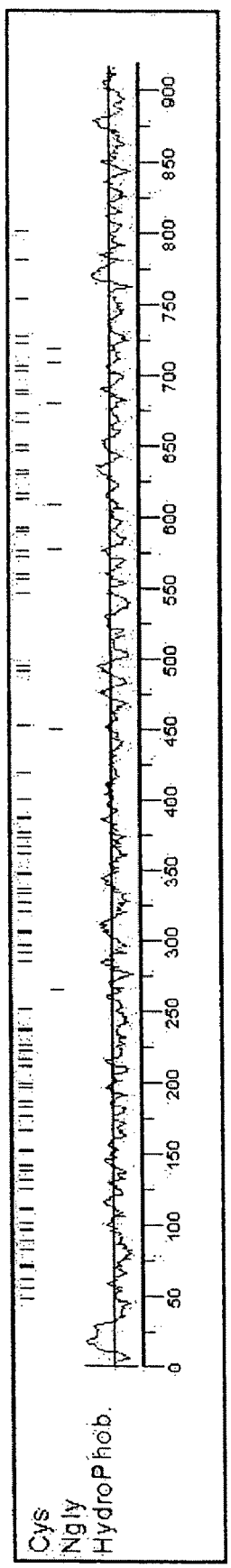
FIG. 13 depicts a hydropathy plot of human SCUBE2. Relatively hydrophobic residues are shown above the dashed horizontal line, and relatively hydrophilic residues are below the dashed horizontal line. The cysteine residues (cys) are indicated by short vertical lines just below the hydropathy trace. The numbers corresponding to the amino acid sequence of human SCUBE2 are indicated. Polypeptides of the invention include fragments which include: all or part of a hydrophobic sequence, e.g., a sequence above the dashed line, e.g., the sequence from about amino acid 300 to 314, from about 756 to 772, and from about 876 to 884 of SEQ ID NO:4; all or part of a hydrophilic sequence, e.g., a sequence below the dashed line, e.g., the sequence from about amino acid 43 to 55, from about 80 to 93, from about 534 to 546, and from about 861 to 872 of SEQ ID NO:4; a sequence which includes a Cys, or a glycosylation site.

Fragments of SCUBE2 which include residues about 43 to 55, from about 80 to 93, from about 534 to 546, and from about 861 to 872 of SEQ ID NO:4 can be used to make, e.g., used as immunogens or used to characterize the specificity of an antibody, antibodies against hydrophilic regions of the SCUBE2 protein (see FIG. 13). Similarly, fragments of SCUBE2 which include residues about 300 to 314, from about 756 to 772, and from about 876 to 884 of SEQ ID NO:4 can be used to make an antibody against a hydrophobic region of the SCUBE2 protein. A fragment of SCUBE2 which includes residues about 49 to 401, or a subset thereof, e.g. about residues 49 to 126, about residues 127 to 252 or about residues 253 to 401 of SEQ ID NO:4 can be used to make an antibody against the N-terminal EGF-repeat region of the SCUBE2 protein; a fragment of SCUBE2 which includes residues about 185 to 200 of SEQ ID NO:4 (SEQ ID NO:22) can be used to make an antibody against the fourth EGF-like repeat of the SCUBE2 protein; a fragment of SCUBE2 which includes residues about 402 to 728, or a subset thereof, e.g. about residues 402 to 480, about 481 to 640, about 641 to 728 of SEQ ID NO:4, or about 471 to 489 of SEQ ID NO:14 (SEQ ID NO:23, which includes residues 403 to 409 of SEQ ID NO:4) can be used to make an antibody against the spacer region of the SCUBE2 protein; or a fragment of SCUBE2 which includes residues about 729 to 838, or a subset thereof, e.g. about residues 729 to 770, about residues 771 to 800 or about residues 801 to 838 of SEQ ID NO:4 can be used to make an antibody against the CUB domain of the SCUBE2 protein.

Figure 14A:
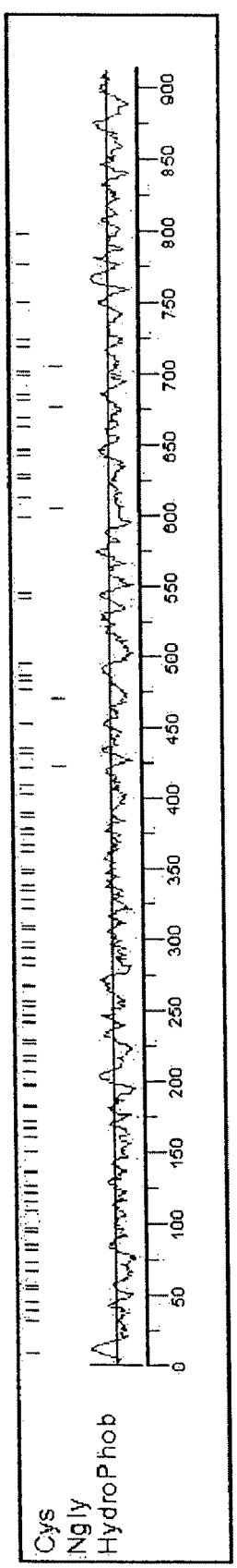
FIGS. 14A and 14B depict hydropathy plots of human SCUBE3.
Figure 14B:
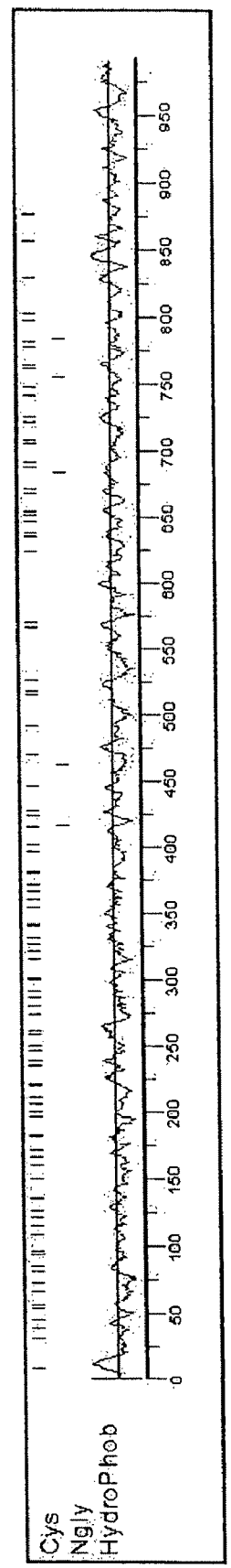

Fragments of SCUBE3 which include residues about 28 to 41, from about 497 to 508, and from about 881 to 897 of SEQ ID NO:6 or about 28 to 41, from about 529 to 540, and from about 960 to 976 of SEQ ID NO:8 can be used to make, e.g., used as immunogens or used to characterize the specificity of an antibody, antibodies against a hydrophilic region of the SCUBE3 protein (see FIGS. 14A and 14B). Similarly, fragments of SCUBE3 which include residues about 201 to 211 and from about 763 to 773 of SEQ ID NO:6 or residues about 254 to 268 and from about 842 to 852 of SEQ ID NO:8 can be used to make an antibody against a hydrophobic region of the SCUBE3 protein. A fragment of SCUBE3 which includes residues about 33 to 404, or a subset thereof, e.g. about residues 33 to 110, about residues 111 to 243 or about residues 244 to 404 of SEQ ID NO:6 or about 33 to 397, or a subset thereof, e.g. about residues 33 to 110, about residues 111 to 236 or about residues 237 to 397 of SEQ ID NO:8 can be used to make an antibody against the N-terminal EGF-repeat region of the SCUBE3 protein; a fragment of SCUBE3 which includes residues about 405 to 724, or a subset thereof, e.g. about residues 405 to 480, about 481 to 640, or about 641 to 724 of SEQ ID NO:6 or about 398 to 803, or a subset thereof, e.g. about residues about residues 398 to 500, about 501 to 640, or about 641 to 803 of SEQ ID NO:8 can be used to make an antibody against the spacer region of the SCUBE3 protein; or a fragment of SCUBE3 which includes residues about 725 to 834, or a subset thereof, e.g. about residues 725 to 770, about residues 771 to 800 or about residues 801 to 834 of SEQ ID NO:6 or about 804 to 913, or a subset thereof, e.g. about residues 804 to 850, about residues 851 to 880 or about residues 881 to 913 of SEQ ID NO:8 can be used to make an antibody against the CUB domain of the SCUBE3 protein.

In one format, the relative amounts of a protein of the invention between a cell population that has been exposed to the agent to be tested compared to an unexposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

Antibody probes are prepared by immunizing suitable mammalian hosts in appropriate immunization protocols using the peptides, polypeptides or proteins of the invention if they are of sufficient length, or, if desired, or if required to enhance immunogenicity, conjugated to suitable carriers. Methods for preparing immunogenic conjugates with carriers such as bovine serum albumin (BSA), keyhole limpet hemocyanin (KLH), or other carrier proteins are well known in the art. In some circumstances, direct conjugation using, for example, carbodiimide reagents may be effective; in other instances linking reagents such as those supplied by Pierce Chemical Co. (Rockford, Ill.), may be desirable to provide accessibility to the hapten. The hapten peptides can be extended at either the amino or carboxy terminus with a cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein (*Nature* 256:495-497, 1975) or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in ascites fluid.

For therapeutic purposes, the antibody can be a polyclonal, monoclonal, recombinant, e.g., a chimeric or humanized, fully human, non-human, e.g., murine, or single chain antibody. Chimeric, humanized, but most preferably, completely human antibodies are desirable for applications which include repeated administration, e.g., therapeutic treatment of human patients, and some diagnostic applications. In a preferred embodiment it has effector function and can fix complement. The antibody can be coupled to a toxin or imaging agent.

The desired monoclonal antibodies are then recovered from the culture supernatant or from the ascites supernatant. Fragments of the monoclonal antibodies or the polyclonal antisera which contain the immunologically significant portion can be used as antagonists, as well as the intact antibodies. Use of immunologically reactive antibody fragments, such as the Fab, Fab', or F(ab')$_2$ fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin, such as humanized antibodies. The antibodies may be used in any of the methods described herein, may be used as diagnostic agents or may be used as therapeutic agents.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559).

A humanized or complementarity determining region (CDR)-grafted antibody will have at least one or two, but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a SCUBE or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, (1987) *From Genes to Clones* (Verlagsgesellschaft, Weinheim, Germany). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison (1985) *Science* 229:1202-1207, by Oi et al. (1986) *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a SCUBE polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. (1986) *Nature* 321:552-525; Verhoeyan et al. (1988) *Science* 239:1534; Beidler et al. (1988) *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65-93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899-903).

The anti-SCUBE antibody can be a single chain antibody. A single-chain antibody (scFV) can be engineered as described in, for example, Colcher et al. (1999) *Ann. N Y Acad. Sci.* 880:263-80; and Reiter (1996) *Clin. Cancer Res.* 2:245-52. The single chain antibody can be dimerized or multimerized to generate multivalent antibodies having specificities for different epitopes of the same target SCUBE protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the therapeutic moiety is not to be construed as limited to classical chemical therapeutic agents. For example, the therapeutic moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-SCUBE antibody (e.g., monoclonal antibody) can be used to isolate SCUBE by standard techniques, such as affinity chromatography or immunoprecipitation. Moreover, an anti-SCUBE antibody can be used to detect SCUBE protein (e.g., in a cellular lysate or cell supernatant) in order to evaluate the abundance and pattern of expression of the protein. Anti-SCUBE antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies which bind only a native SCUBE protein, only denatured or otherwise non-native SCUBE protein, or which bind both, are within the invention. Antibodies with linear or conformational epitopes are within the invention. Conformational epitopes sometimes can be identified by identifying antibodies which bind to native but not denatured SCUBE protein.

Agents that are assayed in the method which measures the relative amounts of a protein of the invention between a cell population that has been exposed to the agent and a control cell population can be randomly selected or rationally selected or designed. As used herein, an agent is said to be randomly selected when the agent is chosen randomly without considering the specific sequences involved in the association of a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agents action. Agents can be rationally selected or rationally designed by utilizing the peptide sequences that make up these sites. For example, a rationally selected peptide agent can be a peptide whose amino acid sequence is identical to or a derivative of any functional consensus site.

The agents of the present invention can be, as examples, peptides, small molecules, vitamin derivatives, as well as carbohydrates. Dominant negative proteins, DNAs encoding these proteins, antibodies to these proteins, peptide fragments of these proteins or mimics of these proteins may be introduced into cells to affect function. "Mimic" used herein refers to the modification of a region or several regions of a peptide molecule to provide a structure chemically different from the parent peptide but topographically and functionally similar to the parent peptide (see Grant G A. in: *Molecular Biology and Biotechnology*, Myers, ed., pp. 659-664, VCH Publishers, New York, 1995). A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

J. Uses for Agents that Modulate at Least One Activity of SCUBE Proteins.

As provided in the Examples, the proteins and nucleic acids of the invention, such as the protein having the amino acid sequence of SEQ ID NO: 2, 4, 17, 19, 6, or 8, are differentially expressed in normal vascular endothelial tissue compared to other normal tissues and in normal endothelial tissue compared to endothelial tissue in vascular and other disease states. Agents that modulate or up-or-down-regulate the expression of the protein, or agents, such as agonists or antagonists of at least one activity of the protein, may be used to modulate biological and pathologic processes associated with the proteins function and activity, e.g. binding to a binding partner. As described above, the agents of the present invention can be, as examples, antibodies, peptides, small molecules, vitamin derivatives, as well as carbohydrates.

As used herein, a subject can be any mammal, so long as the mammal is in need of modulation of a pathological or biological process mediated by a protein of the invention. The term mammal is defined as an individual belonging to the class Mammalia. The invention is particularly useful in the treatment of human subjects.

As used herein, an "effective amount" is an amount of a substance, compound or agent which is effective to inhibit, reduce, ameliorate, modulate or control at least one symptom or effect of a disease, condition or another administered substance, compound or agent either in vivo, ex vivo, or in vitro.

Pathological processes refer to a category of biological processes which produce a deleterious effect. For example, expression of a protein of the invention may be associated with vascular disease. As used herein, an agent is said to modulate a pathological process when the agent reduces the degree or severity of the process. For instance, vascular disease may be prevented or disease progression modulated by the administration of agents which up- or down-regulate or modulate in some way the expression or at least one activity of a protein of the invention.

The agents of the present invention can be provided alone, or in combination with other agents that modulate a particular pathological process. For example, an agent of the present invention can be administered in combination with other known drugs. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or site specific routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents which modulate expression or at least one activity of a protein of the invention. While individual needs vary, determination of optimal ranges of effective amounts of each component is within the skill of the art. Typical dosages comprise 0.1 to 100 μg/kg body wt. The preferred dosages comprise 0.1 to 10 μg/kg body wt. The most preferred dosages comprise 0.1 to 1 μg/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice such as antihistamines. The compounds of this invention can be utilized in vivo, ordinarily in mammals, such as humans, sheep, goats, horses, cattle, pigs, dogs, cats, rats and mice, or in vitro.

K. Transgenic Animals

Transgenic animals containing mutant, knock-out, knock-in or modified genes corresponding to the cDNA sequence of SEQ ID NO: 1, 16, 18, 3, 5, or 7, or the open reading frame encoding the polypeptide sequence of SEQ ID NO: 2, 4, 17, 19, 6, or 8, or fragments thereof having a consecutive sequence of at least about 10, 15, 20, 25, 30, 35, 40, 45, 50 or more amino acid residues, are also included in the invention. Transgenic animals are genetically modified animals into which recombinant, exogenous or cloned genetic material has been experimentally transferred. Such genetic material is often referred to as a "transgene." The nucleic acid sequence of the transgene, in this case a form of SEQ ID NO: 1, 16, 18, 3, 5, or 7 may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

In some embodiments, transgenic animals in which all or a portion of a gene comprising SEQ ID NO: 1, 16, 18, 3, 5, or 7 is deleted may be constructed. In those cases where the gene corresponding to SEQ ID NO: 1, 16, 18, 3, 5, or 7 contains one or more introns, the entire gene—all exons, introns and the regulatory sequences—may be deleted. Alternatively, less than the entire gene may be deleted. For example, a single exon and/or intron may be deleted, so as to create an animal expressing a modified version of a protein of the invention.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. Nos. 4,736,866; 5,602,307; Mullins et al., *Hypertension* 22:630-633, 1993; Brenin et al., *Surg Oncol* 6:99-110, 1997; Tuan, *Recombinant Gene Expression Protocols (Methods in Molecular Biology, Vol. 62)*, Humana Press, Totowa, N.J., 1997).

A number of recombinant or transgenic mice have been produced, including those which express an activated oncogene sequence (U.S. Pat. No. 4,736,866); express simian SV40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess a bovine growth hormone gene (Clutter et al., *Genetics* 143:1753-1760, 1996); or, are capable of generating a fully human antibody response (McCarthy, *Lancet* 349:405, 1997).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al., *Mol Reprod Dev* 46:515-526, 1997; Houdebine, *Reprod Nutr Dev* 35:609-617, 1995; Petters, *Reprod Fertil Dev* 6:643-645, 1994; Schnieke et al., *Science* 278:2130-2133, 1997; and Amoah, *J Animal Science* 75:578-585, 1997).

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. Nos. 5,489,743 and 5,602,307.

L. Diagnostic Methods and Agents

The genes and proteins of the invention may be used to detect SCUBE expressing cells in vivo or ex vivo in a cell suspension or a tissue sample, for example. The genes and proteins of the invention may further be used to diagnose or monitor diseases or conditions with vascular involvement in a subject or sample, or to track disease progression. Such diseases or conditions include, but are not limited to cardiovascular diseases, such as angiogenesis, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis and renal artery stenosis; scleroderma, obesity, inflammatory diseases, such as those following transplantation, systemic lupus erythematosus, autoimmune disease, asthma, emphysema, allergy, diabetes, interstitial nephritis, glomerulonephritis, polycystic kidney disease, and IgA nephropathy; renal tubular acidosis, hypercalceimia, Lesch-Nyhan syndrome, diabetes, cancer metastasis, and other diseases, disorders and conditions of the like.

The use of molecular biological tools has become routine in forensic technology. For example, nucleic acid probes may be used to determine the expression of a nucleic acid molecule comprising all or at least part of the sequences of SEQ ID NO: 1, 16, 18, 3, 5, or 7 in forensic/pathology specimens. Further, nucleic acid assays may be carried out by any means of conducting a transcriptional profiling analysis. In addition to nucleic acid analysis, forensic methods of the invention may target the proteins of the invention, particularly a protein comprising SEQ ID NO: 2, 4, 17, 19, 6, or 8, to determine up or down regulation of the genes (Shiverick et al., *Biochim Biophys Acta* 393:124-133, 1975).

Methods of the invention may involve treatment of tissues with collagenases or other proteases to make the tissue amenable to cell lysis (Semenov et al., *Biull Eksp Biol Med* 104:113-116, 1987). Further, it is possible to obtain biopsy samples from different regions of blood vessels or of the kidney, liver, lungs or other highly vascularized organs for analysis.

Assays to detect nucleic acid or protein molecules of the invention may be in any available format. Typical assays for nucleic acid molecules include hybridization or PCR based formats. Typical assays for the detection of proteins, polypeptides or peptides of the invention include the use of antibody probes in any available format such as in situ binding assays, etc. See Harlow & Lane, *Antibodies—A Laboratory Manual*, Cold Spring Harbor Laboratory Press, Cold Spring Harbor, N.Y., 1988. In preferred embodiments, assays are carried out with appropriate controls.

The above methods may also be used in other diagnostic protocols, including protocols and methods to detect disease states in other tissues or organs, for example the tissues in which gene expression is detected.

M. Detection Assays

Portions or fragments of the cDNA sequences identified herein, their complements and the corresponding complete gene sequences can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample.

The SCUBE sequences of the present invention can be used to identify individuals from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the SCUBE sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The SCUBE sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO: 1, 16, 18, 3, 5, or 7, as described above, can comfortably provide positive individual identification with a panel of perhaps 10 to 1,000 primers that each yield a noncoding amplified sequence of 100 bases. If predicted coding sequences are used, a more appropriate number of primers for positive individual identification would be 500-2,000.

N. Use of SCUBE Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, that can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1, 3, 5, or 7 are particularly appropriate for this use as greater numbers of polymorphisms occur in the noncoding regions, making it easier to differentiate individuals using this technique. Examples of polynucleotide reagents include the SCUBE sequences or portions thereof, e.g., fragments derived from the noncoding regions of SEQ ID NO: 1, 3, 5, or 7 having a length of at least 20 bases, preferably at least 30 bases.

The SCUBE sequences described herein can further be used to provide polynucleotide reagents, e.g., labeled or label-able probes that can be used, for example, in an in situ hybridization technique, to identify a specific tissue, e.g., liver, etc. This can be very useful in cases where a forensic pathologist is presented with a tissue of unknown origin. Panels of such SCUBE probes can be used to identify tissue by species and/or by organ type.

In a similar fashion, these reagents, e.g., SCUBE primers or probes can be used to screen tissue culture for contamination (i.e. screen for the presence of a mixture of different types of cells in a culture).

O. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining a SCUBE protein and/or nucleic acid expression as well as SCUBE protein activity, in the context of a biological sample (e.g., blood, serum, cells, tissue) to thereby determine whether an individual is afflicted with a disease or disorder, or is at risk of developing a disorder, associated with aberrant SCUBE expression or activity. The invention also provides for prognostic (or predictive) assays for determining whether an individual is at risk of developing a disorder associated with a SCUBE protein, nucleic acid expression or activity. For example, mutations in a SCUBE gene can be assayed in a biological sample. Such assays can be used for prognostic or predictive purpose to thereby prophylactically treat an individual prior to the onset of a disorder characterized by or associated with SCUBE protein or nucleic acid expression or activity.

Another aspect of the invention provides methods for determining SCUBE protein or nucleic acid expression or SCUBE protein activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of a SCUBE protein in clinical trials.

P. Diagnostic Assays

A SCUBE polypeptide may be used to identify an interacting polypeptide in a sample or tissue. The method comprises contacting the sample or tissue with a SCUBE protein, allowing formation of a complex between the SCUBE polypeptide and the interacting polypeptide, and detecting the complex, if present.

The proteins of the invention may be used to stimulate production of antibodies specifically binding the proteins. Such antibodies may be used in immunodiagnostic procedures to detect the occurrence of the protein in a sample. The proteins of the invention may be used to stimulate cell growth and cell proliferation in conditions in which such growth would be favorable. An example would be to counteract toxic side effects of chemotherapeutic agents on, for example, vascular endothelium or other endothelial linings of the body, such as those of the brain, spinal cord or eye, for example. They may also be used to stimulate new cell growth in vascular diseases. Alternatively, antagonistic treatments may be administered in which an antibody specifically binding a SCUBE protein of the invention would abrogate the specific growth-inducing effects of the proteins. Such antibodies may be useful, for example, in the treatment of proliferative disorders including various tumors and benign hyperplasias.

Polynucleotides or oligonucleotides corresponding to any one portion of the SCUBE nucleic acid of SEQ ID NO: 1, 16, 18, 3, 5, or 7 may be used to detect DNA containing a corresponding ORF gene, or to detect the expression of a corresponding SCUBE gene. For example, a SCUBE nucleic acid expressed in a particular cell or tissue can be used to identify the presence of that particular cell type.

An exemplary method for detecting the presence or absence of a SCUBE in a biological sample involves obtaining a biological sample from a test subject and contacting the biological sample with a compound or an agent capable of detecting a SCUBE protein or nucleic acid (e.g., mRNA, genomic DNA) that encodes a SCUBE protein such that the presence of a SCUBE molecule is detected in the biological sample. An agent for detecting SCUBE mRNA or genomic DNA is a labeled nucleic acid probe capable of hybridizing to a SCUBE mRNA or genomic DNA. The nucleic acid probe can be, for example, a full-length SCUBE nucleic acid, such as the nucleic acid of SEQ ID NO: 1, 16, 18, 3, 5, or 7, or a portion thereof, such as an oligonucleotide of at least about 15, 30, 50, 100, 250 or 500 nucleotides in length and sufficient to specifically hybridize under stringent conditions to a SCUBE mRNA or genomic DNA, as described above. Other suitable probes for use in the diagnostic assays of the invention are described herein.

An agent for detecting a SCUBE protein is an antibody capable of binding to a SCUBE protein, preferably an antibody with a detectable label. Antibodies can be polyclonal, or more preferably, monoclonal. An intact antibody, or a fragment thereof (e.g., Fab or $F(ab')_2$) can be used. The term labeled, with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term biological sample is intended to include tissues, cells and biological fluids isolated from a subject, as well as tissues, cells and fluids present within a subject. That is, the detection method of the invention can be used to detect a SCUBE mRNA, protein, or genomic DNA in a biological sample in vitro as well as in vivo. For example, in vitro techniques for detection of a SCUBE mRNA include Northern hybridizations and in situ hybridizations, as described above. In vitro techniques for detection of a SCUBE protein include enzyme linked immunosorbent assays (ELISAs), Western blots, immunoprecipitations and immunofluorescence, i.a., the Western blotting and immunoprecipitation methods described above. In vitro techniques for detection of SCUBE genomic DNA include Southern hybridizations. Furthermore, in vivo techniques for detection of a SCUBE protein include introducing into a subject a labeled anti-SCUBE protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a SCUBE protein, mRNA, or genomic DNA, such that the presence of a SCUBE protein, mRNA or genomic DNA is detected in the biological sample, and comparing the presence of a SCUBE protein, mRNA or genomic DNA in the control sample with the presence of a SCUBE protein, mRNA or genomic DNA in the test sample.

The invention also encompasses kits for detecting the presence of a SCUBE molecule in a biological sample. For example, the kit can comprise: a labeled compound or agent capable of detecting a SCUBE protein or mRNA in a biological sample; means for determining the amount of a SCUBE molecule in the sample; and means for comparing the amount of a SCUBE molecule in the sample with a standard. The compound or agent can be packaged in a suitable container. The kit can further comprise instructions for using the kit to detect a SCUBE protein or nucleic acid.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Cloning of SCUBE1 and SCUBE2

The SCUBE1 gene was found to reside on human chromosome 22q13 and is comprised of multiple exons. Cloning and sequencing of the SCUBE1 gene was accomplished by screening a mixed tissue human cDNA library. A pair of primers flanking the ORF of SCUBE1 were used in standard PCR amplification techniques. The resultant PCR product was cloned into pcDNA3.1 and sequenced to confirm that a full-length clone of SCUBE1 had been obtained.

The SCUBE1 nucleic acid sequence is disclosed herein as SEQ ID NO: 1. SCUBE1 is 2992 nucleotides in length and has an open reading frame encoding a protein of 988 amino acids (SEQ ID NO: 2). The ORF spans nucleotides 21-2987 (21-2984 without the TAA stop codon) of SEQ ID NO: 1. A signal peptide is found at amino acids 1-22 of SEQ ID NO: 2 (FIG. 1), and 10 EGF-like domains are found at amino acids 37-72; 78-115; 121-156; 166-202; 206-241; 245-280; 286-321; 327-360; 366-401; and 737-773. A CUB domain is located at amino acids 798-907. Deletion mutants of SCUBE1, D1 and D2, were constructed in a pFLAG-CMV vector (Sigma-Aldrich, St. Louis, Mo., see FIG. 1 for approximate C-terminal boundaries), which supplied the signal sequence for secretion of the mutant polypeptide. The deletion 1 construct (SCUBE1-D1, SEQ ID NO:16) encodes amino acids 26-789 of SEQ ID NO:2 (SEQ ID NO:17, deleting the CUB domain) and the deletion 2 construct (SCUBE1-D2, SEQ ID NO:18) encodes amino acids 26-411 of SEQ ID NO:2 (SEQ ID NO:19, deleting the spacer, the 10th EGF-like domain and the CUB domain).

Human SCUBE1 shows sequence similarity to the mouse SCUBE1 gene (GenBank Accession No. NM_022723, GenPept Accession No. NP_073560, SEQ ID NO:13), approximately 84% identity at the protein level and 87% identity at the nucleic acid level. The mouse protein (961 amino acids in length) is not homologous to the human after 911 amino acids. The human and mouse proteins, therefore, have different C-termini, the significance of which may be that different molecules function as agonists, antagonists and biochemical signals in each animal.

The top portion of FIG. 2 displays the results of a hydrophobicity analysis of the amino acid sequence of SEQ ID NO: 2 (SCUBE1). The protein appears to be largely hydrophilic, particularly in the EGF-like and CUB regions.

The SCUBE2 gene, which has some homology to SCUBE1 and which is located on chromosome 11p15, was discovered by screening commercially available clones (e.g., from OriGene Technologies, Inc., Rockville, Md.) using sequence information from human SCUBE1 and using standard methods such as those described above and in Sambrook et al., supra. The SCUBE2 nucleic acid sequence (SEQ ID NO:3) is 3497 nucleotides in length and contains and open reading frame from nucleotides 81-2837, followed by a TGA stop codon. The encoded protein, 919 amino acids in length includes the secretion signal sequence, 9 EGF-like domains and a CUB domain. FIG. 13 displays the results of a hydrophobicity analysis of the amino acid sequence of SEQ ID NO: 4 (SCUBE2).

In greater detail, the SCUBE2 amino acid sequence is disclosed herein as SEQ ID NO: 4. A signal peptide is found at amino acids 1-37 of SEQ ID NO: 4, and 8 EGF-like domains (Pfam PF00008, SEQ ID NO:9) are found at amino acids 49-84, 90-126, 132-167, 177-213, 217-252, 286-321, 327-362, and 368-401 of SEQ ID NO:4. The spacer region is between amino acids 402-728 of SEQ ID NO:4 and the CUB domain (Pfam PF00431, SEQ ID NO:10) is between amino acids 729-838 of SEQ ID NO:4. SCUBE2 has some Prosite signature sequences: 7 EGF-like domain signature 2 sequences (Prosite PS01186, SEQ ID NO:11) located at about amino acids 71 to 84, 111 to 126, 152 to 167, 198 to 213, 306 to 321, 347 to 362, and 387 to 401 of SEQ ID NO:4; 5 calcium-binding EGF-like domain pattern signatures (Prosite PS01187, SEQ ID NO:12) located at about amino acids 45 to 71, 86 to 111, 128 to 152, 323 to 347, and 364 to 387 of SEQ ID NO:4; and 7 N-glycosylation sites (Prosite PS00001, see FIG. 13) located mostly in the spacer region at about amino acids 266 to 269, 451 to 454, 579 to 582, 610 to 613, 681 to 681, 710 to 713, and 720 to 723 of SEQ ID NO:4. (For reference to Pfam and Prosite annotation, see Example 8.)

Human SCUBE2 shows sequence similarity to a human genome sequencing clone (GenBank Accession No. NM_020974, GenPept Accession No. NP_066025, SEQ ID NO:14), approximately 94% identity at the nucleic acid level and approximately 92% identity compared to the protein predicted from the genomic clone. An alignment of SCUBE2 with the NM_020974 protein suggests that they are splice variants, with NM_020974 having an insert of about 80 amino acids at about amino acid residue 403 of SEQ ID NO:4 (from about 404 to 483 of SEQ ID NO:14).

Example 2

SCUBE mRNA Expression in Vascular Endothelium

SCUBE cDNA, or portions or fragments thereof, can be used to detect the presence of SCUBE mRNA in human tissues, as well as to probe for SCUBE-related gene products in other species.

Differential expression of SCUBE in human tissues was determined using by Northern blotting and by RT-PCR.

Figure 5:
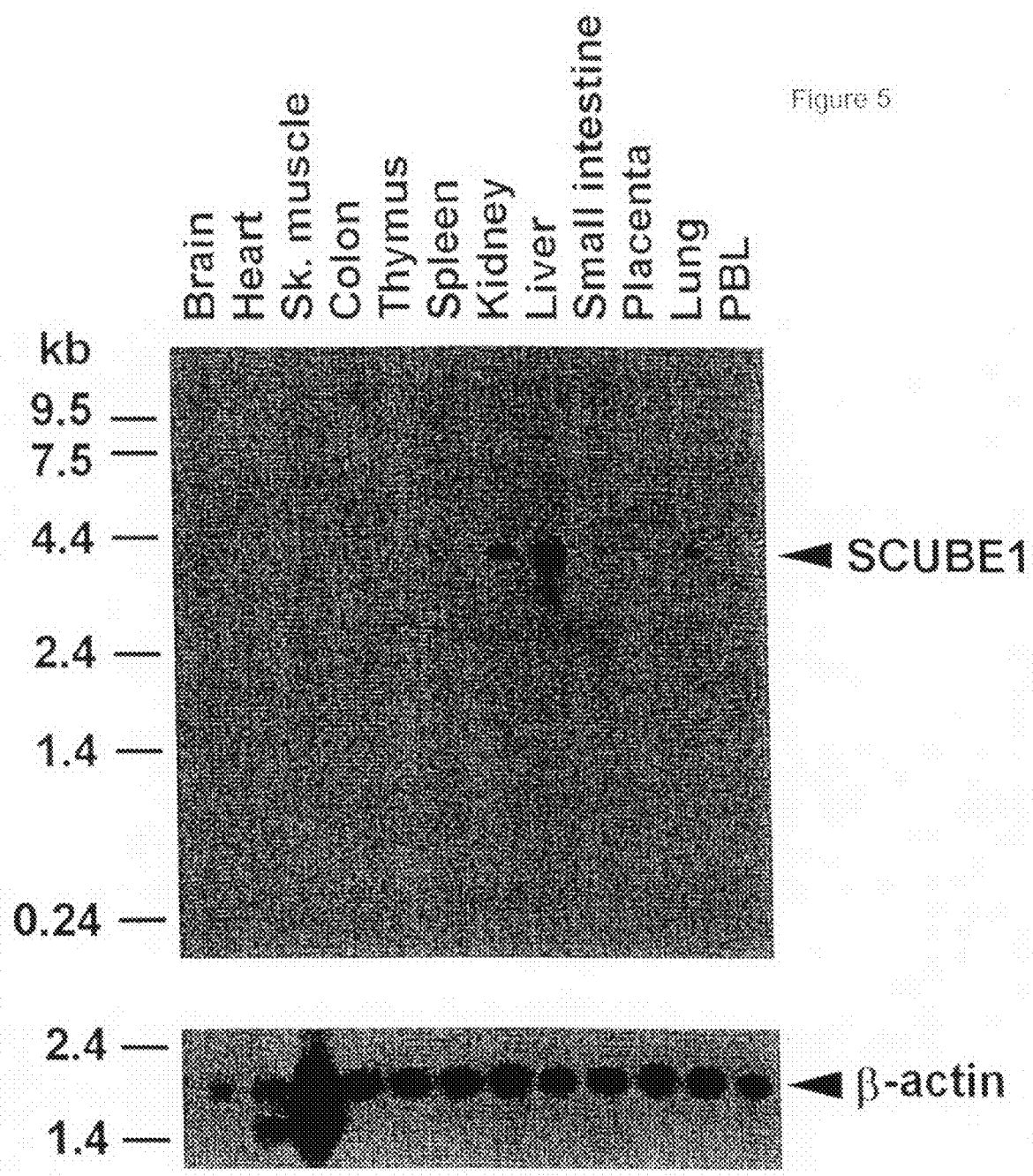
FIG. 5, upper panel, shows a Northern blot analysis of poly(A)+ mRNA from various human tissues for SCUBE1. mRNA samples were hybridized to a SCUBE1 cDNA radiolabeled probe, which identified an mRNA species of ~4.0 kb. The lower panel shows the same blot in which mRNA samples were probed with β-actin as a control.
Figure 9:
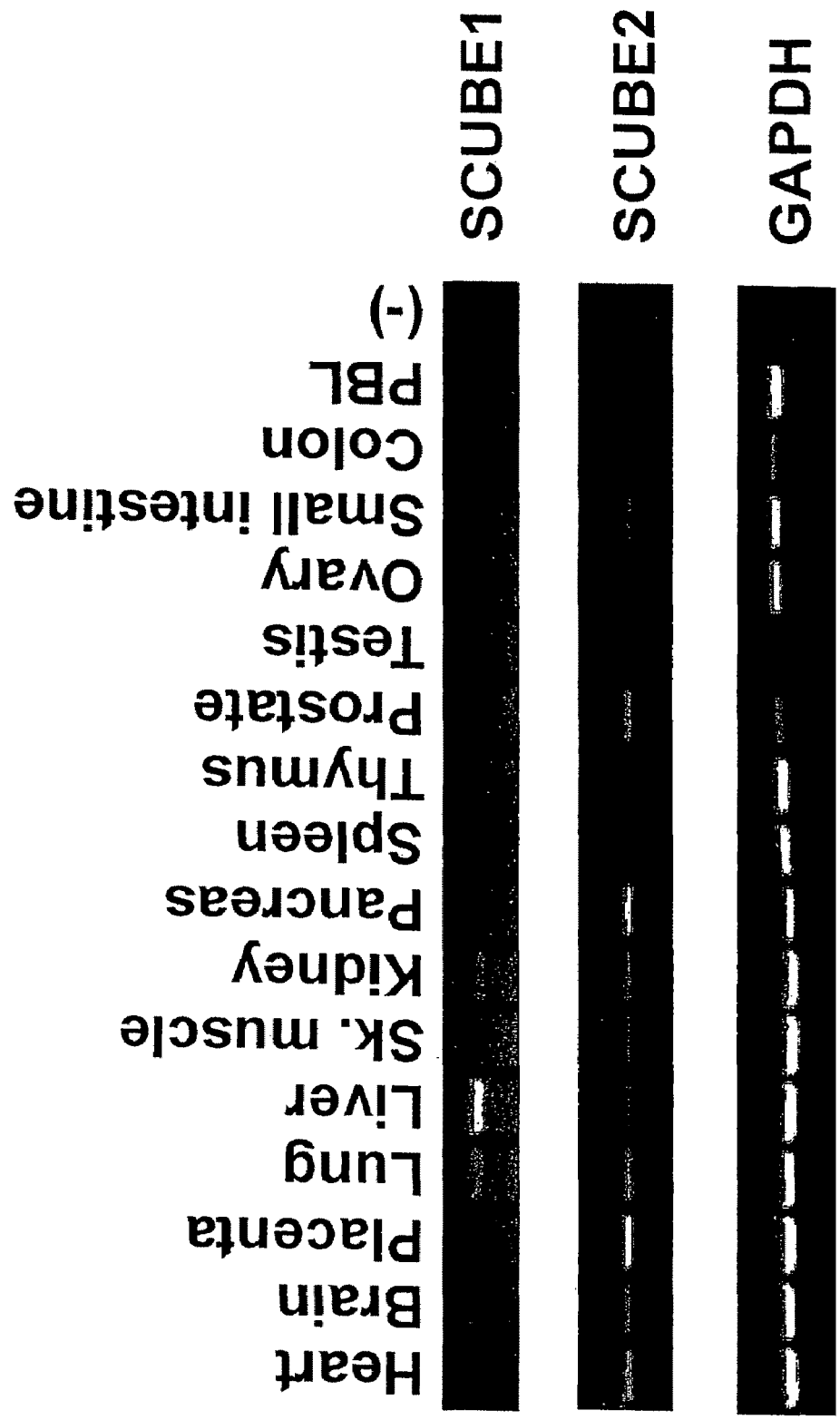
FIG. 9 shows the tissue distribution of the SCUBE gene family as determined by RT-PCR analyses. Human tissue cDNAs were amplified with primers specific for SCUBE1 and SCUBE2. Amplification of GAPDH was performed as a positive control.

The tissue distribution of RNA encoding the protein of SEQ ID NO: 2 was analyzed by Northern blot (FIG. 5), as well as by RT-PCR expression analysis (FIG. 9). For Northern blotting, RNA was isolated from the following human tissues using standard protocols: human brain, heart, skeletal muscle, colon, thymus, spleen, kidney, liver, small intestine, placenta, lung and peripheral blood lymphocytes. Northern blots were prepared using a probe derived from SEQ ID NO: 1, with hybridization conditions as described by Sambrook et al. Expression of SCUBE1 is strong in the liver, kidney, lung, and small intestine.

RT-PCR expression analysis was also performed on the samples listed above, as well as on samples prepared from pancreas, prostate, testis and ovary tissue, using primers derived from SEQ ID NO: 1 or 3 and using AmpliTaq PCR® amplification kits (Perkin Elmer). Again, SCUBE1 is strongly expressed in the liver, kidney and lung, while SCUBE2 has a broader tissue distribution. It is expressed at relatively higher levels in the lung, placenta, pancreas, prostate and heart, and at lower levels in the liver, kidney, small intestine, brain and skeletal muscle.

SCUBE1 cDNA was used as a probe for the detection of SCUBE1 mRNA expression in tissue sections. Human umbilical vein and artery samples and several tissue samples from *Cynomolgus macaque* monkeys (brain, lung and kidney samples) were probed using standard in situ hybridization techniques. Both samples display highly specific expression of SCUBE1 in the vascular endothelium (see FIGS. 11a-11f). Further, the results show clearly that SCUBE1 cDNA can be used to probe or generate probes for related genes in other species. In contrast, FIGS. 12a-12f show that the mouse SCUBE1 gene has a broad range of expression in fetal mouse tissues. It is expressed in embryonic cardiac muscle, cardiac blood vessels, lung, thoracic wall, small intestine and brain, although no expression was found in adult tissues—heart, brain, spleen, lung, liver, skeletal muscle, kidney or testis (Grimmond et al., *Genomics* 70:74-81, 2000).

Example 3

SCUBE1 is a Secreted Protein

As predicted by the signal sequence and EGF-like motifs, the SCUBE1 protein is secreted (see FIG. 3). HEK-293 cells were transfected with the expression vector encoding Myc-tagged human SCUBE1 at the C-terminus (SCUBE1.Myc) and the endogenous signal peptide. Forty-eight hours after transfection, conditioned medium was collected and cells were detached with PBS. Extracellular matrix on the culture dish was extracted with Laemmli sample buffer. Samples from conditioned culture medium (Medium), cell lysates (Cell) and the extracellular matrix (Matrix) were separated by 4-20% SDS-polyacrylamide gel electrophoresis and transferred to PVDF membranes. Recombinant SCUBE1 proteins were detected in the culture medium and in the cell lysate by Western blotting with anti-Myc antibody (FIG. 3a).

HEK-293 cells were also transfected with the expression vector encoding both Flag- and Myc-tagged SCUBE1 at the N- and C-termini (Flag.SCUBE1.Myc). Two days after transfection, samples from conditioned culture medium (Medium), cell lysates (Cell) and the extracellular matrix (Matrix) were separated by 4-20% SDS-polyacrylamide gel electrophoresis and transferred to PVDF membranes. Recombinant SCUBE1 proteins were detected by Western blotting with anti-Flag M2 or anti-Myc antibody. Again, the blots show that SCUBE1 is secreted into the culture medium and that the secreted protein is the same size as the protein that remains associated with the cells, i.e., the whole protein is secreted, rather than a cleaved product (FIG. 3b).

Conditioned culture medium from cells transfected with Flag.SCUBE1.Myc was also immunoprecipitated with anti-Flag M2 antibody, and the precipitate then was immunoblotted with indicated antisera (FIG. 3c). This experiment confirms that secreted SCUBE1 is not a proteolytic product.

Figure 4:
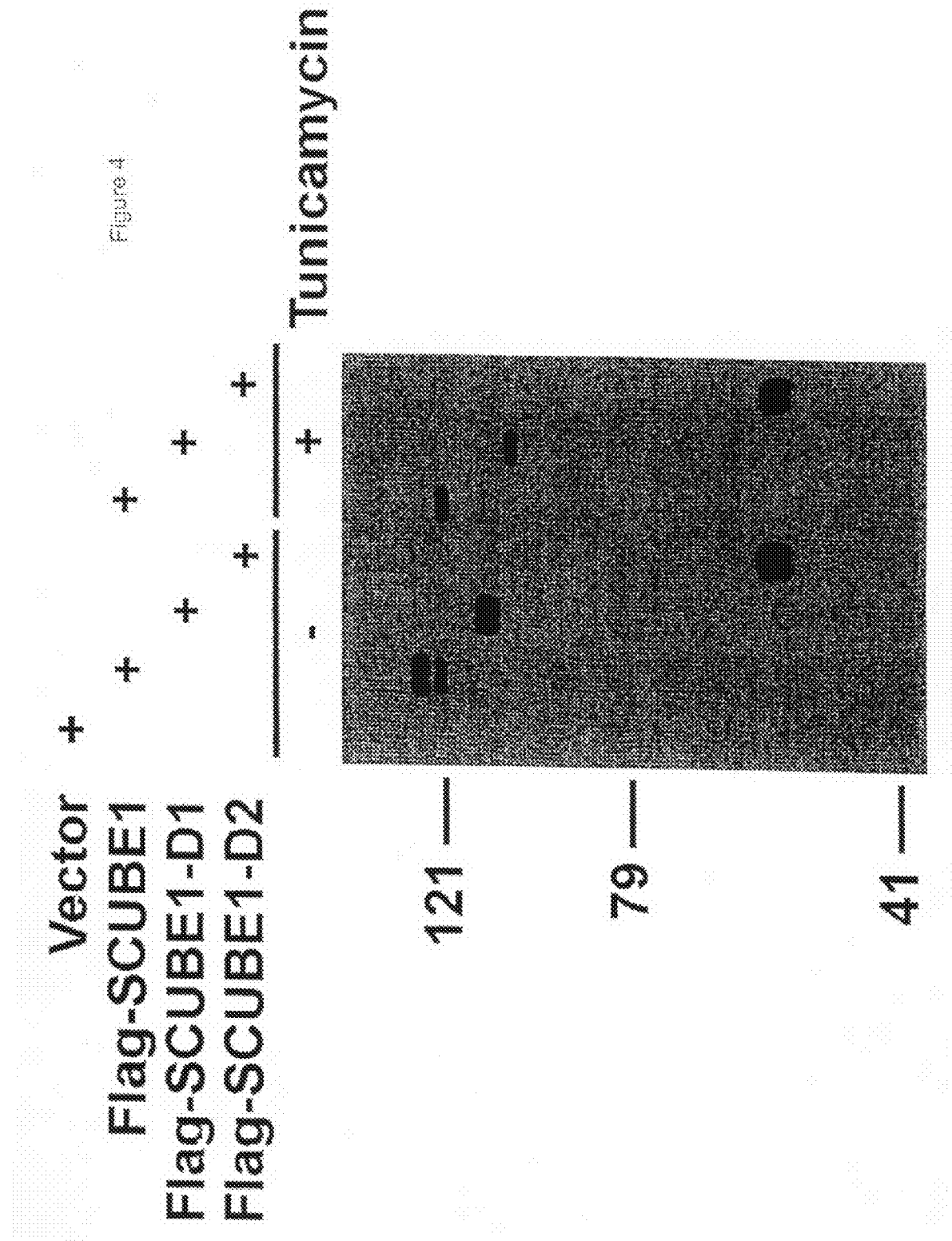
FIG. 4 shows that human SCUBE1 is a glycosylated protein. When Flag-tagged full-length or deletion versions (D1 and D2) of human SCUBE1 were cultured in the absence (−) or in the presence (+) of tunicamycin, a glycosylation inhibitor, Western blot analysis of cell lysates reveals that smaller molecules are produced in the presence of tunicamycin.

SCUBE1 is also a glycosylated protein (FIG. 4). HEK-293 cells were transfected with the expression vector encoding Flag-tagged full-length or deletion versions (D1 and D2) of human SCUBE1. Transfected cells were cultured in the absence (−) or in the presence (+) of tunicamycin, a potent inhibitor of glycosylation of asparagine residues, for twenty-four hours. Cell lysates from each culture were analyzed by Western blotting with anti-Flag M2 antibody. For each construct tested, glycosylation of the expressed protein was inhibited by tunicamycin, producing a smaller glycoprotein molecule, as shown by each pair of samples in the Western blot.

Figure 6:
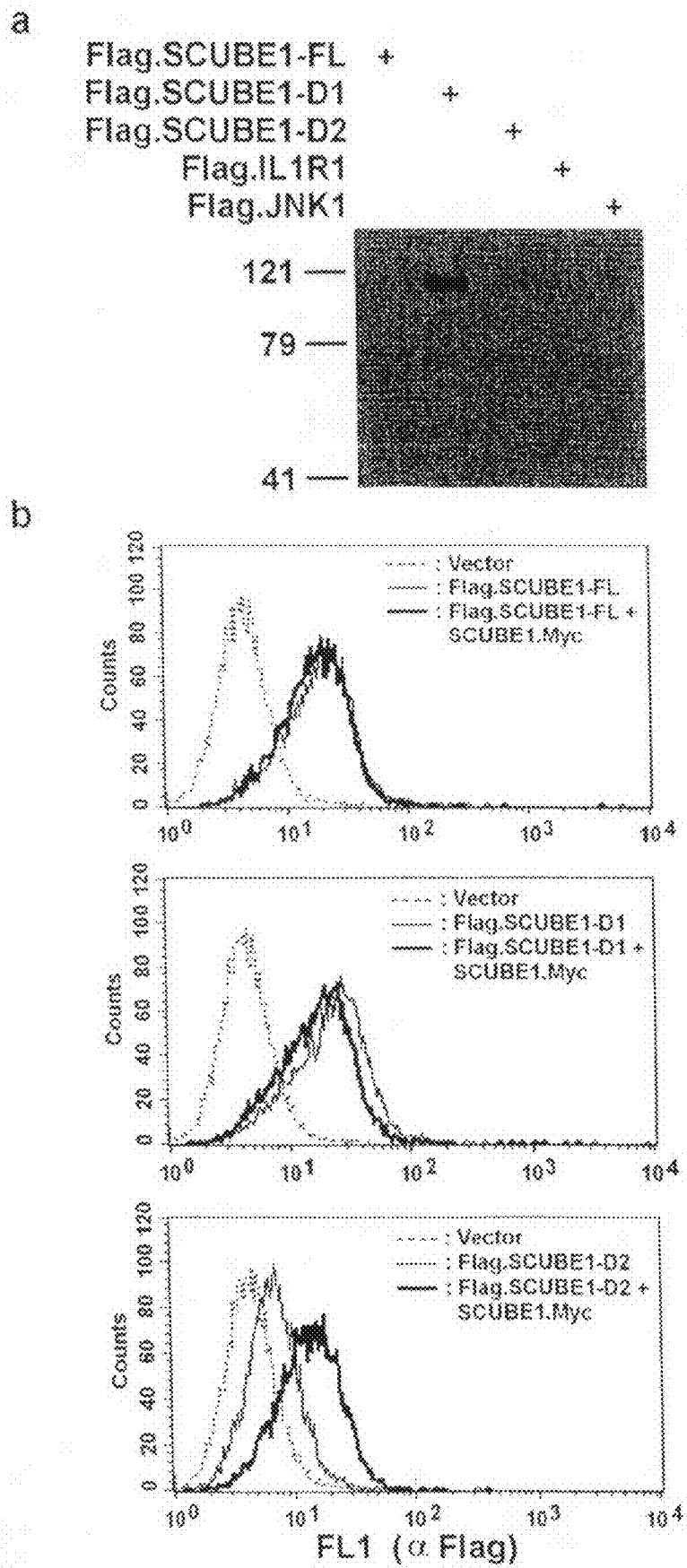
FIG. 6 illustrates that a spacer region is critical for the secretion and surface expression of SCUBE1. a) Vector constructs containing full-length SCUBE1, SCUBE1-D1 and SCUBE1-D2 were analyzed by Western blotting and labeling with anti-Flag M2 antibody, showing that the proteins lacking the spacer region were not secreted (SCUBE1-D2 and controls). b) The expression constructs Flag-SCUBE1-FL (top), -D1 (middle), or -D2 (bottom) were singly or co-transfected with SCUBE1.Myc plasmid into cells and the cell surface analyzed by flow cytometry and labeling with anti-Flag M2 antibody. Again, only proteins containing the spacer region (SCUBE1-FL and SCUBE1-D1) were expressed on the cell surface.

A spacer region is critical for the secretion and surface expression of SCUBE1 (FIG. 6). As shown in FIG. 6a, HEK-293 cells were transfected with the expression plasmids encoding Flag-tagged full-length SCUBE1, Flag-tagged SCUBE1-D1, Flag-tagged SCUBE1-D2, Flag-tagged IL-1R1 or Flag-tagged JNK1. Two days after transfection, conditioned culture medium was concentrated and separated on SDS-PAGE and Western blotted with anti-Flag M2 antibody. Only the constructs containing the spacer sequence could encode proteins that were secreted into the cell medium, i.e., full-length and D1 SCUBE. FIG. 6b shows that the spacer region is essential for cell-surface expression of recombinant SCUBE1. The expression constructs Flag-SCUBE1-FL (top), -D1 (middle), or -D2 (bottom) were singly or co-transfected with SCUBE1.Myc plasmid in HEK-293 cells. Twenty-four hours after transfection, cells were detached, stained with anti-Flag M2 antibody and analyzed by flow cytometry. Cell number in the flow channel was plotted as a function of fluorescence intensity, using fluorescently labeled SCUBE1 proteins as a cell surface marker. The graphs show that cells containing Flag-SCUBE1-FL or Flag-SCUBE1-FL and SCUBE1.Myc have the same surface properties when Flag is detected; Flag-SCUBE1-FL is externalized to the same degree in the two preparations. Cell surface properties are almost the same when the same constructs with SCUBE-D1 are transfected instead of SCUBE-FL (almost as much Flag-SCUBE-D1 protein is on the cell surface in co-transfected cells as in cells transfected with one vector). When these constructs containing SCUBE-D2 are used, however, two Flag-containing peaks are detected, indicating that the Flag-SCUBE1-D2 proteins remain internalized in the cells, while protein complexes composed of Flag-SCUBE1-D2 linked to SCUBE1.Myc are found on the cell surface, externalization enabled by the spacer region in the SCUBE1.Myc portion.

Figure 7:
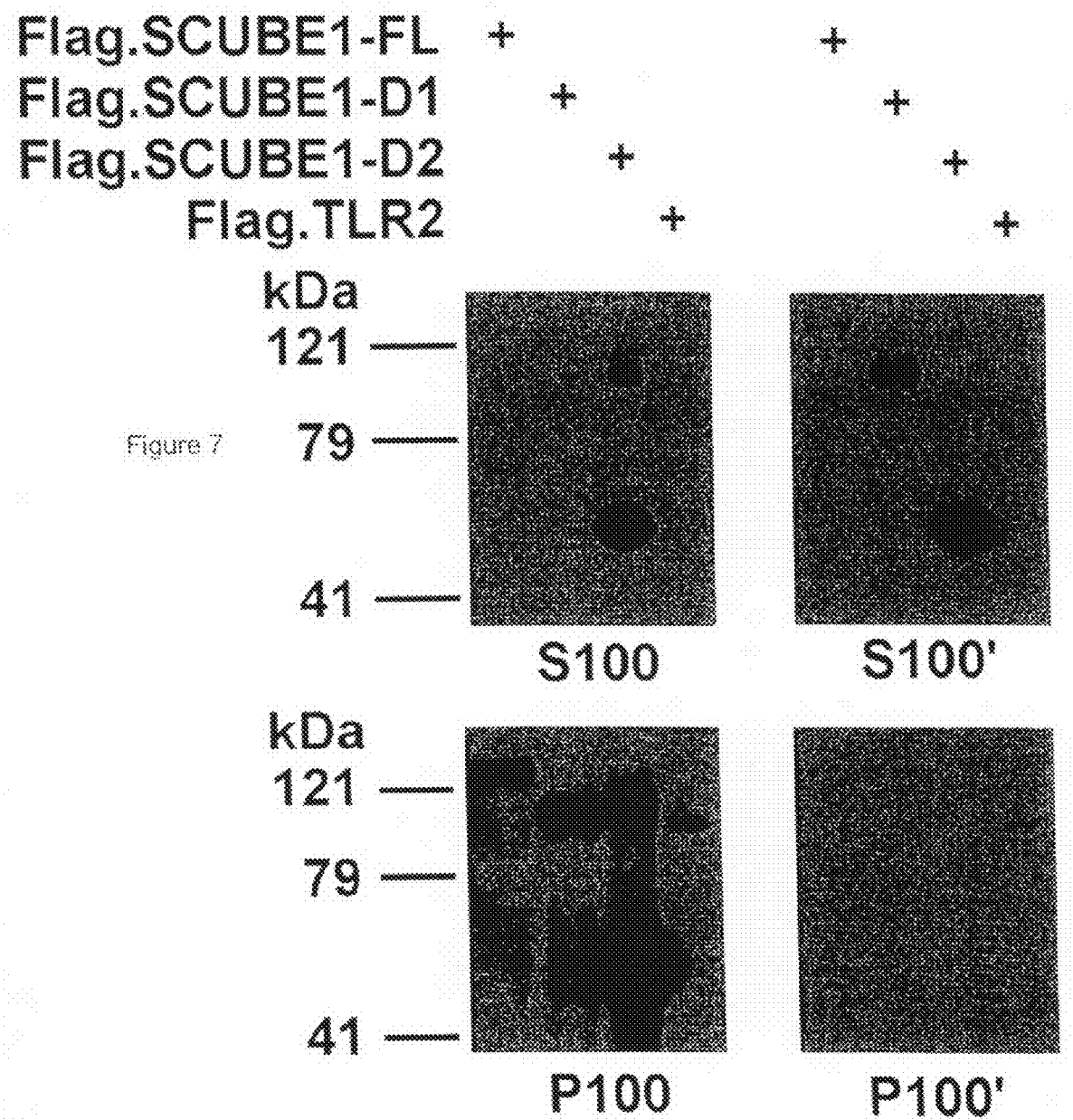
FIG. 7 shows the membrane association of human SCUBE1 protein. Samples of supernatant from homogenized cells transfected with several SCUBE1 constructs show the presence of the protein encoded by the SCUBE1-D2 construct, while proteins encoded by the longer constructs remained in the cell pellets. When the cell membranes were disrupted by sonication and centrifuged, full-length SCUBE1 and SCUBE1-D1 proteins could be detected in the soluble membrane fraction.

FIG. 7 shows the membrane association of human SCUBE1 protein. HEK-293 cells were transfected with expression plasmids encoding Flag-tagged full-length SCUBE1, SCUBE1-D1, SCUBE1-D2 and TLR2 (control) proteins, and, two days after transfection, cells were collected and homogenized. Samples of supernatant (S10) were centrifuged at 100,000×g for 30 min to give soluble fractions (S100) and pellets (P100 membrane fraction). Pellets were resuspended in original volumes of homogenization buffer with 0.1 M $Na_2CO_3$ (pH 12), sonicated briefly, and then incubated on ice for 30 min. Samples were centrifuged again at 100,000×g for 30 min. to give washed fractions S100' and pellets P100'. Each fraction was subjected to SDS-PAGE and immunoblot analysis using anti-Flag M2 antibody. The results show that only the protein encoded by the D2 construct is present in appreciable amounts in the first soluble fraction, while the full-length and D1 construct proteins remain associated with the membrane. Upon disruption by sonication, however, they are released from the membrane and can be detected in the soluble membrane fraction. The ability of SCUBE1 to form homo-oligomers in transfected HEK-293 cells is shown in FIG. 8. FIG. 8a shows the homomeric interaction of SCUBE1 proteins. Flag-SCUBE1 and SCUBE1.Myc were singly or co-transfected in 293T cells. As a control, SCUBE1.Myc was expressed together with Flag-tagged IL-1β receptor (Flag.IL-1R1). Immunoprecipitation (IP) and Western blot (WB) were performed using antisera as indicated. The bands indicate the presence of protein complexes that can be precipitated by one antibody and detected by another. FIG. 8b shows that EGF-like repeats are sufficient for SCUBE1 homotypic associations. The spacer and CUB sequences are not required. SCUBE1.Myc was expressed together with Flag.SCUBE1-FL, -D1, or -D2 by transient transfection. Detergent lysates were immunoprecipitated with anti-Myc antibody and then immunoblotted with anti-Flag M2 antibody to determine the associated proteins. Cell lysates were also immunoblotted to examine the protein expression levels. In each case, a protein complex that could be precipitated with anti-Myc antibody was detected with anti-Flag M2 antibody.

Example 4

Down-regulation of SCUBE Expression by Cellular Signaling Factors (IL-1β, TNF-α) or by Toxins (LPS)

Figure 10A:
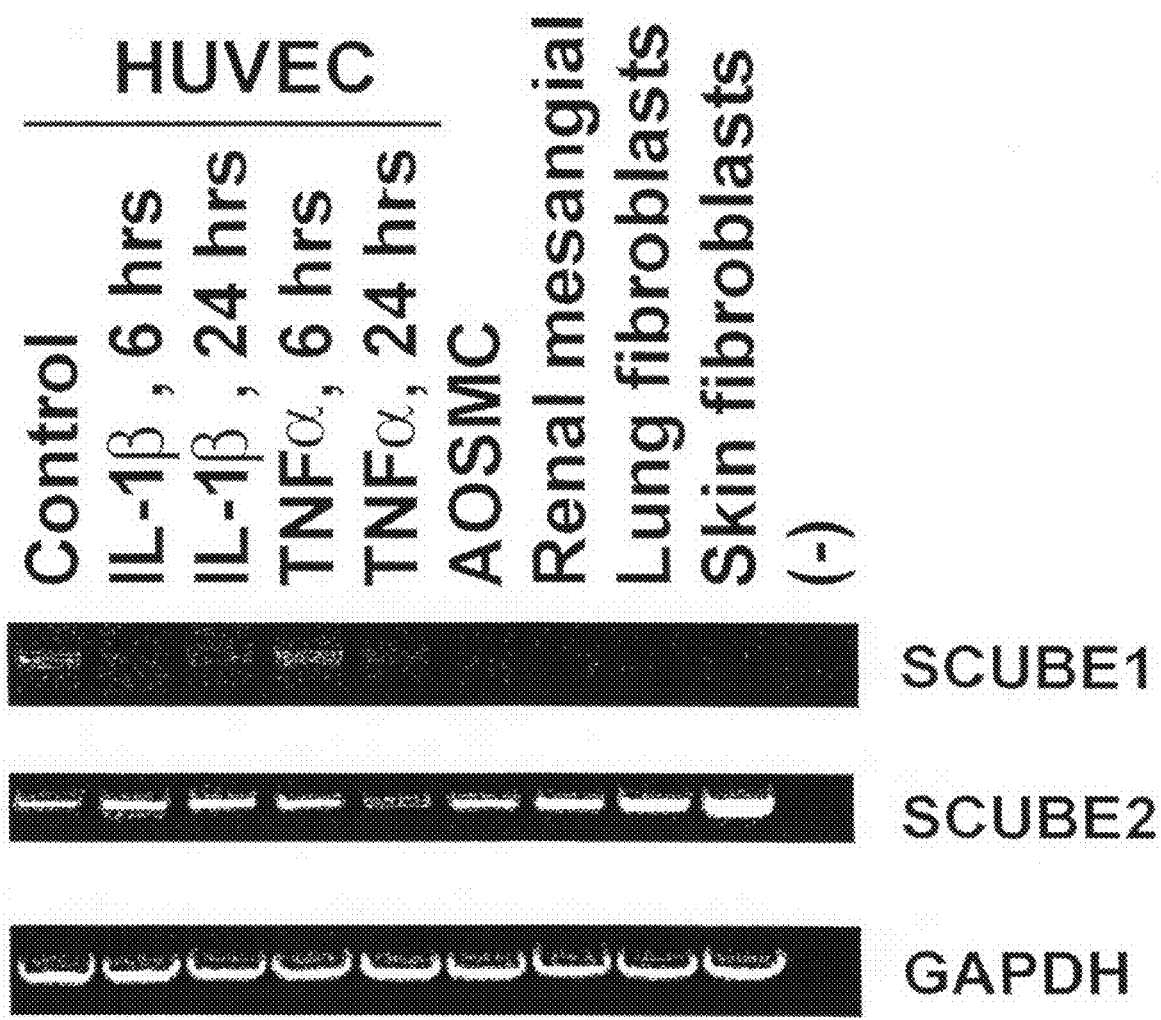
FIGS. 10a and 10b show the down-regulation of SCUBE1 and SCUBE2 expression in various cell lines and in mouse kidney tissue following exposure to pro-inflammatory cytokines (IL-1β or TNF-α) or to lipopolysaccharides (LPS).
Figure 10B:
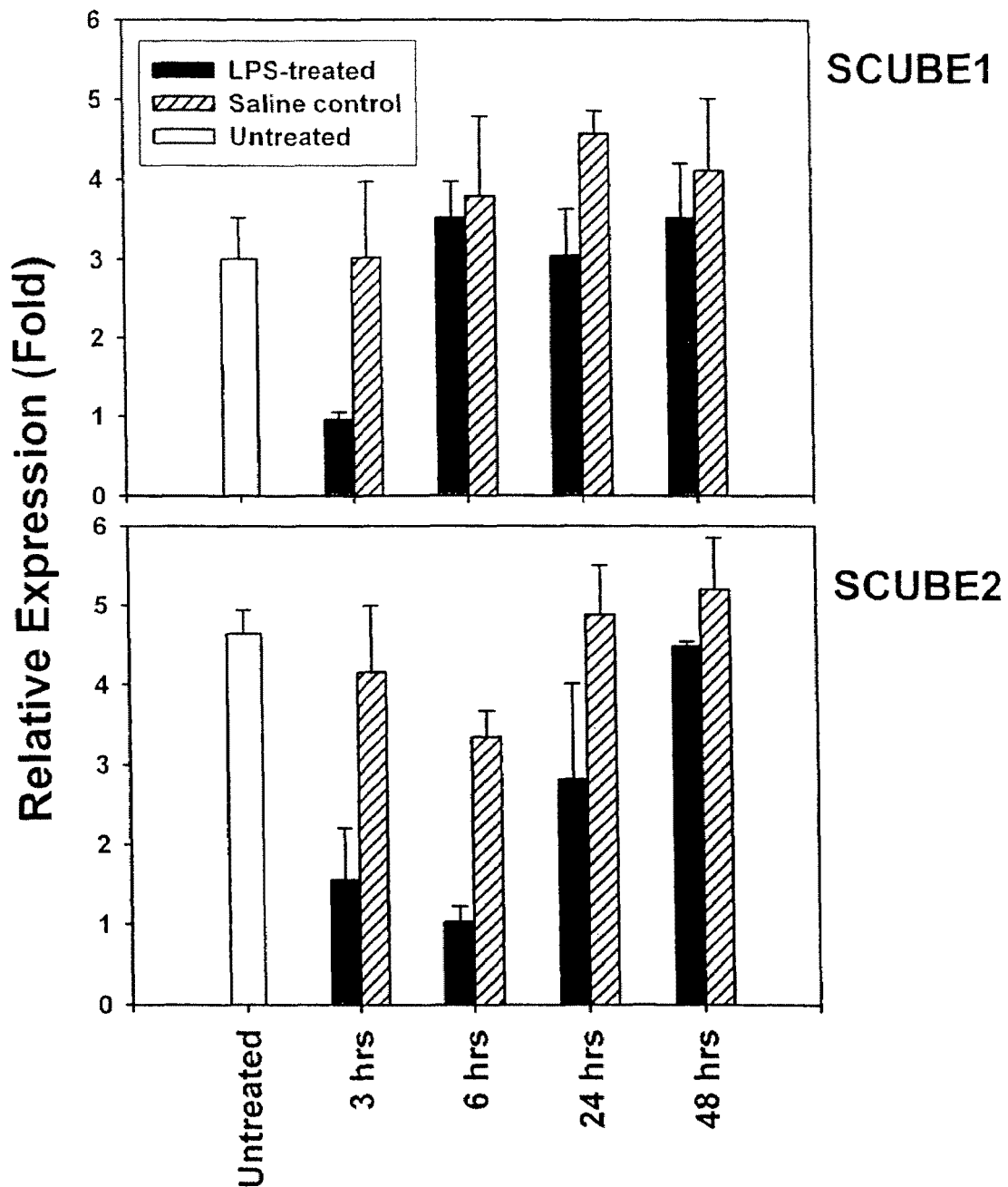
Figure 11:
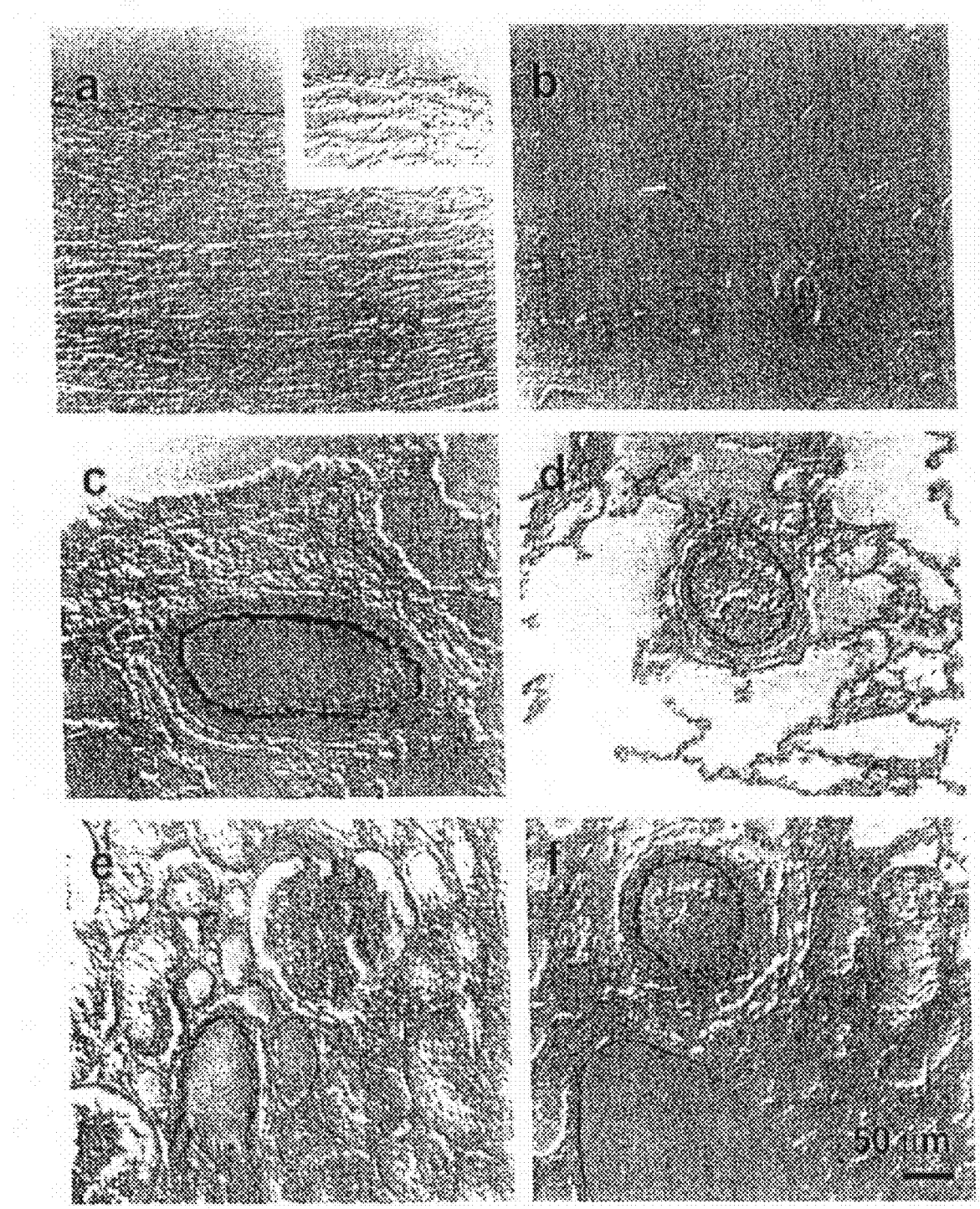
FIGS. 11a-11f illustrate endothelial expression of SCUBE1 in human umbilical vessels and in monkey tissues. In situ hybridization was used to confirm the endothelial expression in a) human artery and vein, as well as in several monkey tissues including b) brain, c, d) lung and e, f) kidney.
Figure 12:
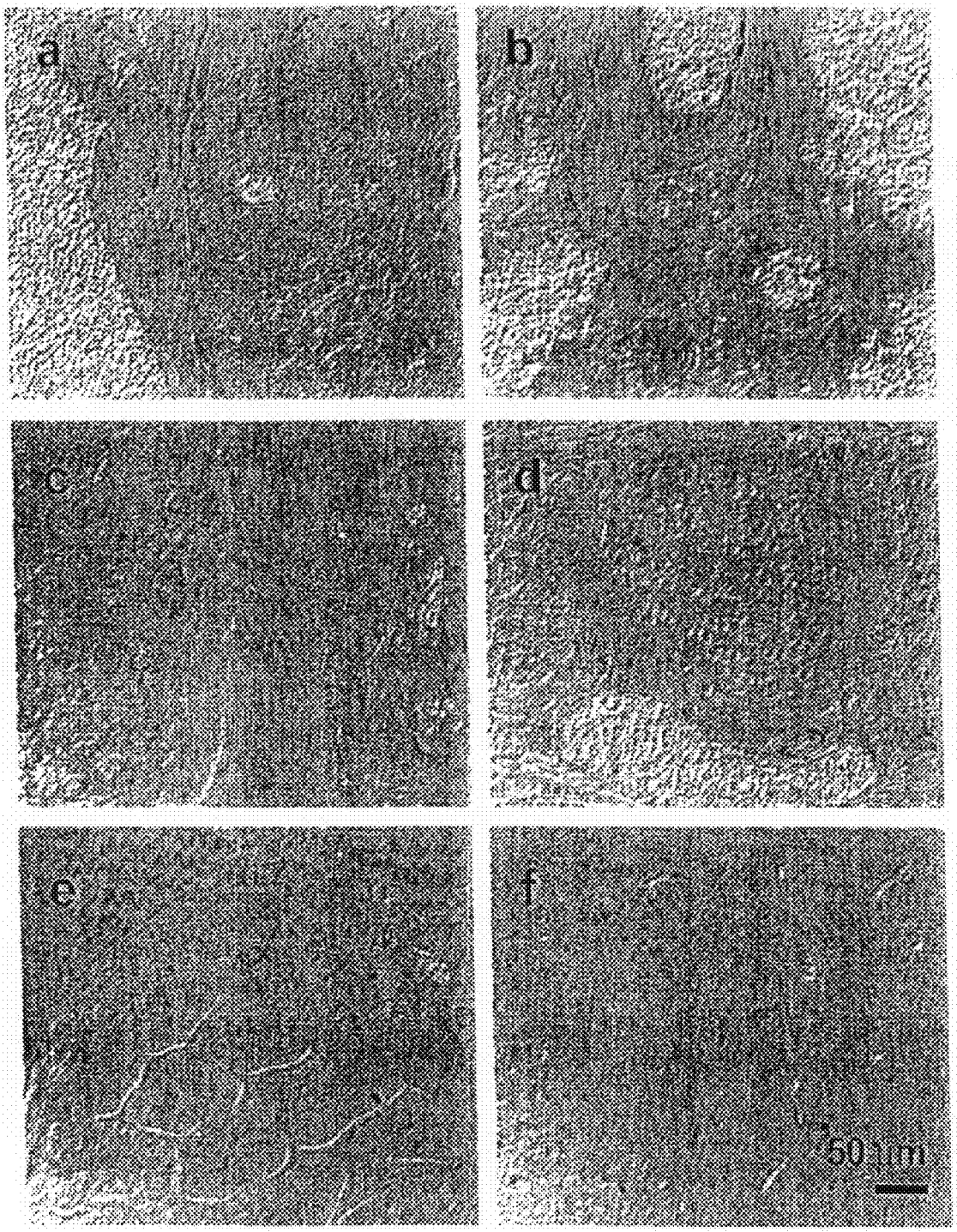
FIGS. 12a-12f show the expression of mouse SCUBE1 in various mouse embryonic tissues: a) heart; b) vena cava and aorta; c) lung; d) thoracic wall; e) small intestine; f) cerebrum.

SCUBE1 and SCUBE2 messages were down-regulated following treatment with pro-inflammatory cytokines or lipopolysaccharides (LPS) in vitro and in vivo (see FIG. 10). As shown in a), pro-inflammatory cytokines decreased expression of the SCUBE gene family in vitro. Several human primary cell lines and HUVEC treated with IL-1β or TNF-α for 6 and 24 hrs were analyzed by RT-PCR. b) shows the inhibition of SCUBE gene expression in the kidney after intraperitoneal injection of LPS. C57/B16 mice were sacrificed at the indicated times after i.p. injection of either LPS at 5 mg/kg or PBS vehicle. Kidneys were collected and submitted for TaqMan analyses. Down-regulation of SCUBE1 was strongest 3 hours after exposure to LPS, while down-regulation of SCUBE2 was most marked 3 and 6 hours after exposure to LPS, both returning to normal levels in 48 hours.

Example 5

Interaction of SCUBE1 with Growth Factors

SCUBE1 was co-transfected into HEK-293 cells using the methods of Example 3, above, along with an expression vector containing the gene for PDGF-C or PDGF-D (platelet-derived growth factor C or D). Analysis of proteins in cell lysates antibody preparations showed the presence of protein complexes containing SCUBE1 and PDGF-C or SCUBE1 and PDGF-D. These results indicate that the binding of SCUBE may serve to modulate growth factor activity. These findings also suggest that SCUBE proteins can be used as therapeutic compounds to regulate the activity of growth factors, such as PDGF-C or PDGF-D.

Example 6

Antibodies to SCUBE1 and SCUBE2

Monoclonal Antibodies to SCUBE1. A GST-fusion protein with the CUB domain of human SCUBE1 as antigen was generated for monoclonal antibody production. After immunization and fusion, three clones showed specificity for human SCUBE1 by immunoprecipitation (IP), fluorescent antibody cell sorting (FACS) analyses and/or western blot (WB). The results of characterizing the antibodies are shown in Table 1.

TABLE 1

Characterization of SCUBE1 Monoclonal Antibody Clones

| Clone # | Isotype | IP | FACS | WB |
|---------|---------|----|----|----|
| 33 | IgG3 | + | + | + |
| 701 | IgG1 | + | + | + |
| 712 | IgG1 | + | | + |

Polyclonal Antibodies to SCUBE1 and SCUBE2. Polyclonal antibodies to peptides from SCUBE1 and SCUBE2 were elicited in chickens. The peptides used as immunogens are listed in Table 2:

TABLE 2

SCUBE1 and SCUBE2 Peptides For Raising Chicken Antibodies

| Peptide Sequence | SEQ ID NO: | Region of Protein | Location in Protein |
|---|---|---|---|
| ECSEGTDDCHIDAIC | SEQ ID NO:20 | first EGF-like domain of SCUBE1 | from about amino acid residues 36 through 50 of SEQ ID NO:2 |
| KARFKIRDAKCHLRPHS | SEQ ID NO:21 | spacer region of SCUBE1 | from about amino acid residues 487 through 503 of SEQ ID NO:2 |
| SHICKEAPRGSVACEC | SEQ ID NO:22 | fourth EGF-like domain of SCUBE2 | from about amino acid residues 185 through 200 of SEQ ID NO:4 |
| FLRCHSGIHLSSDVTTIRT | SEQ ID NO:23 | spacer region of SCUBE2 in splice region of overlap with NM_020974 | from about amino acid residues 471 through 489 of SEQ ID NO:14 (partial overlap in residues 403 to 409 of SEQ ID NO:4) |

The chicken antibodies were prepared from these sequences by Washington Biotechnology, Inc. (Baltimore, Md.). Briefly, peptides were synthesized and linked to keyhole limpet hemocyanin for immunization of chickens. The immunized chickens then produced Y'EGGS (immune eggs), from which the yolks yielded IgY antibodies, with specific antibodies present at about 5% of total IgY. Purification of specific SCUBE antibodies yielded solutions with about >90% specific IgY antibodies. The antibodies demonstrated specificity for SCUBE1 or SCUBE2 on western blots of recombinantly expressed SCUBE1 or SCUBE2 or of lysates of human umbilical cord endothelial cells. In addition, use of the antibodies in immunohistochemistry confirmed that both SCUBE1 and SCUBE2 proteins are expressed in endothelial cells in vivo.

Example 7

SCUBE1 is Found in Thrombi

Monkey tissues were collected from exsanguinated animals in which thrombi were allowed to form in the bleeding process. Tissues were prepared for immunochemistry and examined after reaction with SCUBE1 monoclonal antibodies from clones 33 and 701. Both antibody clones yielded the same result. SCUBE1 was detected in thrombi in many tissues, including in kidney and spleen.

Example 8

Isolation of SCUBE3

SCUBE3 (gene MG44547) was first identified as 47971-031 (SCUBE3.1) in a search for polynucleotides homologous to sequences in various receptor classes. The 47971-031 nucleic acid sequences of the present invention were classified by means of one or more HMM motifs and/or TBLASTN set. The HMM motif included a consensus sequence for a receptor protein domain. The TBLASTN set included a set of protein sequence probes corresponding to amino acid sequence motifs that are conserved in various receptor classes/families. The novel sequences were derived from usually random cDNA library sequencing. The HMM/TBLASTN motifs were used to "hunt" for specific receptor classes among the novel sequences. The 47971 nucleic acid sequence was identified in the hunt using tumor necrosis factor receptor (TNFR)/nerve growth factor receptor (NGFR) motifs from the cysteine-rich regions of those molecules. A number of proteins, some of which are known to be receptors for growth factors, were found to contain a cysteine-rich domain of about 110 to 160 amino acids in their N-terminal part, that can be subdivided into four (or in some cases, three) modules of about 40 residues containing 6 conserved cysteines. The HMM Probes for TNF Receptor/NGF Receptor domain were Pfam identifier: PF00020 and Prosite identifier: PDOC00561. (For general information regarding PFAM identifiers and PF prefix domain identification numbers, refer to Sonnhammer et al. (1997) *Protein* 28:405-420 and the Pfam database, release 2.1, and the Pfam website maintained in several locations, e.g. by the Sanger Institute (pfam.sanger.ac.uk), Washington University (pfam.wustl.edu), the Karolinska Institute (pfam.cgr.kr.se) or Institut dela National Recherche Agronomique (pfamjouy.inra.fr); for general information regarding Prosite identification numbers, refer to Sonnhammer et al. (1997) *Protein* 28:405-420 and the ExPASy (Expert Protein Analysis System) proteomics server of the Swiss Institute of Bioinformatics (SIB), Geneva, Switzerland.)

The 47971-031 (SCUBE3.1) nucleic acid sequence (SEQ ID NO:5) is 3193 nucleotides in length and contains and open reading frame from nucleotides 449-3190, followed by a TAG stop codon. The encoded protein, 914 amino acids in length includes the secretion signal sequence, 9 EGF-like domains and a CUB domain. FIG. 14A displays the results of a hydrophobicity analysis of the amino acid sequence of SEQ ID NO: 6 (SCUBE3.1).

The second example of isolation of the SCUBE3 (gene MG44547) sequence yielded the Fbh47971FL clone (SCUBE3.2). This process began from searching for sequences with homology to the 47971-031 sequences. Clones containing 47971 sequences were walked to produce a full length clone which was inserted into a pFLAGCMV1 vector with a FLAG epitope tag (Sigma Pharmaceuticals, St. Louis, Mo.) or a pSecTag vector with a myc epitope tag (Invitrogen Corp., Carlsbad, Calif.). This clone, named Fbh47971FL has 99% identity to the nucleic acid and protein sequences found in GenBank Accession No. AF452494, GenPept Accession No. AAN76808 (SEQ ID NO:15).

The Fbh47971FL (SCUBE3.2) nucleic acid sequence (SEQ ID NO:7) is 3947 nucleotides in length and contains and open reading frame from nucleotides 443-3421, followed by a TAG stop codon. The encoded protein, 993 amino acids in length includes the secretion signal sequence, 9 EGF-like domains and a CUB domain. FIG. 14B displays the results of a hydrophobicity analysis of the amino acid sequence of SEQ ID NO: 8 (SCUBE3.2).

47971 (gene MG44547) (SCUBE3) is located on human chromosome 6p21.

In greater detail, the SCUBE3 amino acid sequences are disclosed herein as SEQ ID NO: 6 (SCUBE3.1) and SEQ ID NO:8 (SCUBE3.2). A signal peptide is found at amino acids 1-21 of SEQ ID NO: 6 and 8, and 9 EGF-like domains (Pfam PF00008, SEQ ID NO:9) are found at amino acids 33 to 68, 74 to 110, 116 to 151, 161 to 197, 208 to 243, 247 to 282, 288 to 323, 329 to 362, and 368 to 404 of SEQ ID NO:6; and at amino acids 33 to 68, 74 to 110, 116 to 151, 161 to 197, 201 to 236, 240 to 275, 281 to 316, 322 to 355, and 361 to 397 of SEQ ID NO:8. The spacer region is found at about amino acids 405-724 of SEQ ID NO:6 and 398 to 803 of SEQ ID NO:8 and the CUB domain (Pfam PF00431, SEQ ID NO:10) is found at about amino acids 725 to 834 of SEQ ID NO:6 and 804 to 913 of SEQ ID NO:8. SCUBE3 polypeptides have some Prosite signature sequences: 7 EGF-like domain signature 2 sequences (Prosite PS01186, SEQ ID NO:11) located at about amino acids 55 to 68, 95 to 110, 136 to 151, 182 to 197, 267 to 282, 308 to 323, and 348 to 362 of SEQ ID NO:6 and at about amino acids 55 to 68, 95 to 110, 136 to 151, 182 to 197, 260 to 275, 301 to 316, and 341 to 355 of SEQ ID NO:8; 6 calcium-binding EGF-like domain pattern signatures (Prosite PS01187, SEQ ID NO:12) located at about amino acids 29 to 55, 70 to 95, 112 to 136, 284 to 308, 325 to 348, and 364 to 388 of SEQ ID NO:6 and 29 to 55, 70 to 95, 112 to 136, 277 to 301, 318 to 341, and 357 to 381 of SEQ ID NO:8; and 5 N-glycosylation sites (Prosite PS00001, see FIG. 13) located in the spacer region at about amino acids 424 to 427, 471 to 474, 606 to 609, 677 to 680, and 706 to 709 of SEQ ID NO:6 and at about amino acids 417 to 420, 464 to 467, 685 to 688, 756 to 759 and 785 to 788 of SEQ ID NO:8. (For reference to Pfam and Prosite annotation, see Example 8.)

Example 9

Expression Analysis of SCUBE2 and SCUBE3

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using $\beta$-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human SCUBE expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human SCUBE2 and SCUBE3 genes. Each human SCUBE probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human SCUBE gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human SCUBE3 gene is normalized by subtracting the Ct value of the β-2 microglobulin gene to obtain a $_\Delta Ct$ value using the following formula: $_\Delta Ct = Ct_{human\ SCUBE} - Ct_{\beta\text{-2 microglobulin}}$. Expression is then calibrated against a cDNA sample showing a comparatively low level of expression of the human SCUBE3 gene. The $_\Delta Ct$ value for the calibrator sample is then subtracted from $_\Delta Ct$ for each tissue sample according to the following formula: $_{\Delta\Delta}Ct = _\Delta Ct_{sample} - _\Delta Ct_{calibrator}$. Relative expression is then calculated using the arithmetic formula given by $2^{-\Delta\Delta Ct}$. Expression of the target human SCUBE gene in each of the tissues tested is then graphically represented as discussed in more detail below.

In addition to the SCUBE2 expression found in Example 2, the analysis found some regulated expression of SCUBE2 in some disease conditions. For example, these results indicate that SCUBE2 has high levels of expression in urge urinary incontinence (UUI) bladder and lower levels of expression in normal bladder. SCUBE2 also has high levels of expression in breast tumor and low levels of expression in normal breast.

The results indicate that SCUBE3 has high levels of expression in osteoblasts and normal fetal kidney, medium levels of expression in normal artery, normal vein, fetal heart, normal adult heart, normal ventricle, umbilical cord, and diseased aorta and medium to low levels in ischemic ventricle. In contrast, SCUBE3 expression is low in idiopathic artery, ischemic artery, and coronary diseased artery, to indicate regulated expression of SCUBE3 in some disease processes. Another example of regulated SCUBE3 expression is the medium level of SCUBE3 expression in urge urinary incontinence (UUI) bladder and only a trace level of expression in normal bladder.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. An isolated antibody or antigen-binding fragment thereof that binds to a polypeptide which has at least 92% amino acid sequence identity with SEQ ID NO: 4.

2. A kit comprising the antibody or antigen-binding fragment thereof of claim 1 and instructions for use.

3. A method of diagnosing a disease state in a subject, comprising determining the level of expression of a polypeptide which has at least 92% amino acid sequence identity with SEQ ID NO: 4 by measuring the binding of the antibody or antigen-binding fragment thereof of claim 1 to the polypeptide.

4. The method of claim 3, wherein the disease state is selected from the group consisting of atherosclerosis, ischemia, a coagulation disorder, thrombosis, a breast disorder and a urinary bladder disorder.

5. The antibody or antigen-binding fragment thereof of claim 1, wherein the polypeptide bound by the antibody or antigen-binding fragment thereof comprises an amino acid sequence which is at least 95% identical to the amino acid sequence of SEQ ID NO: 4.

6. The antibody or antigen-binding fragment thereof of claim 1, wherein the polypeptide bound by the antibody or antigen-binding fragment thereof consists of the amino acid sequence of SEQ ID NO: 4.

7. The antibody or antigen-binding fragment thereof of claim 1, wherein the antigen-binding fragment thereof is selected from the group consisting of an scFV fragment, a dcFV fragment, an Fab fragment, an Fab' fragment and an F(ab')$_2$ fragment.

8. The antibody or antigen-binding fragment thereof of claim 1, wherein the antigen-binding fragment thereof is selected from the group consisting of polyclonal, monoclonal, recombinant, chimeric, humanized, and fully human.

9. The antibody or antigen-binding fragment thereof of claim 1, wherein the antibody or antigen-binding fragment thereof is conjugated to a therapeutic moiety.

10. The antibody or antigen-binding fragment thereof of claim 1, wherein the antibody or antigen-binding fragment thereof is conjugated to a detectable substance.

11. An antibody or antigen-binding fragment thereof that binds to a peptide comprising a sequence selected from the group consisting of:
  a) SEQ ID NO: 22;
  b) SEQ ID NO: 23; and
  c) amino acids 402 to 480 of SEQ ID NO: 4.

* * * * *